(12) United States Patent
Yang et al.

(10) Patent No.: US 10,336,710 B2
(45) Date of Patent: Jul. 2, 2019

(54) BENZIMIDAZOLE DERIVATIVES, PREPARATION METHOD THEREFOR, AND APPLICATIONS THEREOF

(71) Applicant: BEIJING PHARMACEUTICAL GROUP CO., LTD., Beijing (CN)

(72) Inventors: Yan Yang, Beijing (CN); Wenfeng Wang, Beijing (CN); Zhankun Hu, Beijing (CN); Xiangyu Sun, Beijing (CN); Huijun Yin, Beijing (CN); Xuewei Tian, Beijing (CN)

( * ) Notice: Subject to any disclaimer, the term of this patent is extended or adjusted under 35 U.S.C. 154(b) by 0 days.

(21) Appl. No.: 16/015,227

(22) Filed: Jun. 22, 2018

(65) Prior Publication Data

US 2018/0297959 A1    Oct. 18, 2018

Related U.S. Application Data

(63) Continuation-in-part of application No. PCT/CN2016/110330, filed on Dec. 16, 2016.

(30) Foreign Application Priority Data

Dec. 22, 2015  (CN) .......................... 2015 1 0968215

(51) Int. Cl.
| | | |
|---|---|---|
| *C07D 235/28* | (2006.01) | |
| *A61K 31/4184* | (2006.01) | |
| *C07D 405/12* | (2006.01) | |
| *A61K 45/06* | (2006.01) | |

(52) U.S. Cl.
CPC ........ *C07D 235/28* (2013.01); *A61K 31/4184* (2013.01); *A61K 45/06* (2013.01); *C07D 405/12* (2013.01)

(58) Field of Classification Search
CPC .................................................... C07D 235/28
See application file for complete search history.

(56) References Cited

U.S. PATENT DOCUMENTS

| | | | | |
|---|---|---|---|---|
| 4,520,196 A | * | 5/1985 | Wei ...................... | C07D 235/28 544/251 |
| 5,152,929 A | * | 10/1992 | Bentley ................ | C07D 235/28 252/391 |

OTHER PUBLICATIONS

Chemical Abstracts Registry No. 1937325-33-1, indexed in the Registry file on STN CAS Online Jun. 23, 2016. (Year: 2016).*
Chemical Abstracts Registry No. 571952-91-5, indexed in the Registry file on STN CAS Online Aug. 24, 2003. (Year: 2003).*

* cited by examiner

*Primary Examiner* — Laura L Stockton
(74) *Attorney, Agent, or Firm* — Law Offices of Albert Wai-Kit Chan, PLLC

(57) ABSTRACT

The present invention belongs to the pharmaceutical field, and relates to a preparation method for a series of benzimidazole derivatives, their pharmaceutical salts and pharmaceutically acceptable prodrugs, a pharmaceutical composition containing the derivatives, and the uses of the derivatives and pharmaceutical composition in the preparation of antigout drugs and in the treatment of related diseases.

12 Claims, 1 Drawing Sheet

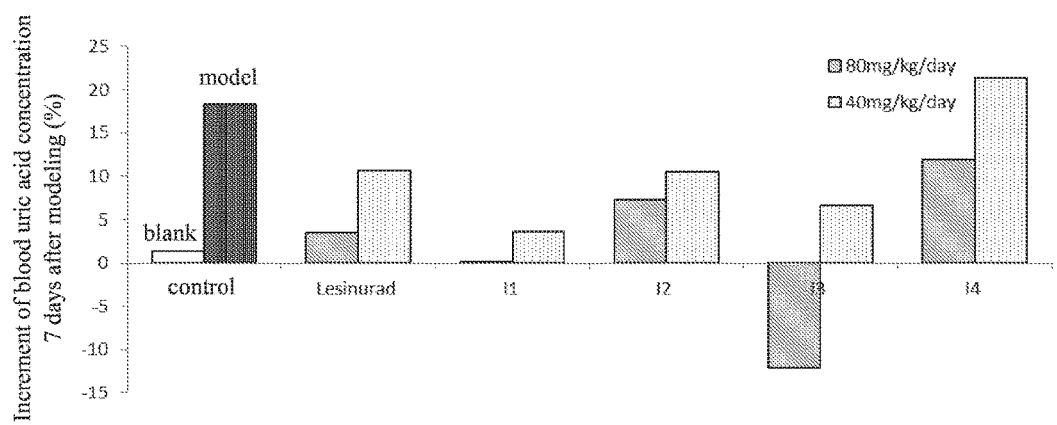

BENZIMIDAZOLE DERIVATIVES, PREPARATION METHOD THEREFOR, AND APPLICATIONS THEREOF

FIELD OF THE INVENTION

The present invention belongs to the pharmaceutical field, and relates to a preparation method for a series of benzimidazole derivatives, their pharmaceutically acceptable salts and pharmaceutically acceptable prodrugs, a pharmaceutical composition comprising the derivatives, and the uses of said derivatives and pharmaceutical composition in the preparation of antigout drugs and in the treatment of related diseases.

BACKGROUND OF THE INVENTION

Gout arises from purine metabolism disorder in the body and building up of excess uric acid in blood, causing precipitation of urate in joints, kidneys and connective tissues, leading to gouty arthritis, gouty neuphropathy, urolithiasis, etc., medically referred to as gout. The disease is characterized by the presence of birefringent sodium monohydrate crystals in synovial fluid and tophi. Its clinical features include hyperuricemia and urate crystals, characteristic acute arthritis, tophi and interstitial nephritis resulted from deposition, joint deformity and dysfunction in severe cases, usually accompanied by uric acid urolithiasis, which is mostly found in obese middle-aged and elderly males and postmenopausal females.

Medicaments for treatment of gout are divided into 3 classes according to their functional characteristics:

The first class would be antigout drugs including indomethacin and colchicine tablets.

Indomethacin has a mild uricosuric effect that relieves pain arising from gout attacks. It is often used in bone joint diseases caused by gout. This drug, which are not suitable for long-term use, must be swallowed whole, and individuals with gastric ulcer, epilepsy and mental disorders are prohibited from this drug.

Colchicine tablets have relatively larger toxic adverse effects, and its use is currently limited to acute gout attack. Some patients experience reactions such as vomiting and diarrhea after administering this drug and the optimal dose of colchicine against gout requires further study.

The second class would be uricosuric drugs. Probenecid belongs to this class of drugs. Its main function is to suppress urate reabsorption by renal tubules so as to increase urate excretion and decrease urate concentration in blood to prevent formation of urate crystals and improve joint function. This drug also promotes dissolution of existing urate crystals. The drug has no anti-inflammatory and analgesic effects, and is generally administered for treating chronic gout or during gout recovery.

The third class would be inhibitors of uric acid synthesis.

Allopurinol belongs to this class of drugs. Its main function is to prevent hypoxanthine and xanthine in the body from metabolizing into uric acid by inhibiting xanthine oxidase so as to reduce uric acid formation. It can be administered to treat primary, secondary and chronic gouts. This drug cannot control acute inflammation during gout attacks, and can only be administered approximately two weeks after the acute phase of gout resolved.

Uric acid is a result of xanthine oxidation. Uric acid metabolic disorders include, but are not limited to diseases related to abnormality of uric acid metabolism such as polycythemia, myeloid metaplasia, gout, recurrent gout attacks, gouty arthritis, hyperuricemia, hypertension, cardiovascular diseases, coronary heart diseases, Lesch-Nyhan syndrome, Kelley-Seegmiller syndrome, renal diseases, nephrolithiasis, renal failure, joint inflammatory disorders, arthritis, urolithiasis, lead poisoning and sarcoidosis.

Lesinurad is an orally administered effective URAT1 inhibitor. Results from phase-1 and 2 clinical trials show that, when used in combination with xanthine oxidase inhibitors, Lesinurad can effectively modulate uric acid levels, and has higher levels of safety. Its structural formula is shown below:

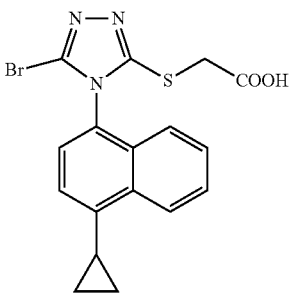 [SMILES: O=C(O)CSc1nnc(Br)n1-c1ccc(C2CC2)c2ccccc12]

Lesinurad has problems such as low pharmacodynamic activity, large dosage and high nephrotoxicity and development of URAT1 inhibitors with higher therapeutic efficacy is needed. The present invention provides an antigout drug having improved therapeutic effect based on the discovery of a series of benzimidazole and their derivatives exhibiting good URAT1 inhibitory effects which outperform Lesinurad during in vitro screening and pharmacological studies.

SUMMARY OF THE INVENTION

The first object of the present invention to provide benzimidazole derivatives, their pharmaceutically acceptable salts, solvates, hydrates, optical isomers or pharmaceutically acceptable prodrugs as represented by Formula (I):

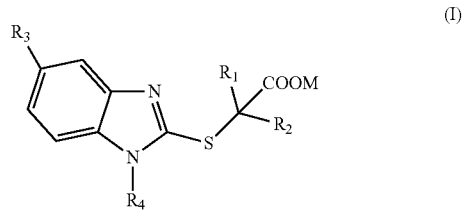

wherein:

$R_1$ and $R_2$ are selected from the group consisting of hydrogen, alkyl, phenyl, and substituted phenyl, wherein the substituent in said substituted phenyl is selected from the group consisting of halogen, cyano, alkyl, alkoxy, ester, N-acyl derivatives, N-acyloxy derivatives and amino acid conjugates;

$R_3$ is selected from the group consisting of hydrogen, halogen, cyano, linear or branched $C_{1-6}$ alkyl and linear or branched $C_{1-6}$ alkoxy;

$R_4$ is selected from the group consisting of alkyl, phenyl, substituted phenyl, naphthyl and substituted naphthyl, wherein the substituent in said substituted phenyl and substituted naphthyl is selected from the group consisting of halogen, cyano, alkyl, alkoxy, ester, N-acyl derivatives, N-acyloxy derivatives and amino acid conjugates;

M is selected from the group consisting of hydrogen, $C_{1-6}$ alkyl, amino, ester and pharmaceutically acceptable cations.

Preferably, the benzimidazole derivatives of this invention, its pharmaceutically acceptable salts, solvates, hydrates, optical isomers and pharmaceutically acceptable prodrugs are selected from the group consisting of:

2-methyl-2-[[5-methoxy-1-(4-cyanonaphth-1-yl)-1H-benzo[d]imidazol-2-yl]thio]propanoic acid (I1);
2-methyl-2-[[1-(4-cyanonaphth-1-yl)-1H-benzo[d]imidazol-2-yl]thio]propanoic acid (I2);
2-methyl-2-[[5-bromo-1-(4-cyanonaphth-1-yl)-1H-benzo[d]imidazol-2-yl]thio]propanoic acid (I3);
2-methyl-2-[[1-(4-cyanophenyl)-1H-benzo[d]imidazol-2-yl]thio]propanoic acid (I4);
2-methyl-2-[[1-(4-cyclopropylnaphth-1-yl)-1H-benzo[d]imidazol-2-yl]thio]propanoic acid (I5);
2-(4-chlorophenyl)-2-[[1-(4-cyclopropylnaphth-1-yl)-1H-benzo[d]imidazol-2-yl]thio]acetic acid (I6);
2-methyl-2-[[1-(4-nitro-2-fluorophenyl)-1H-benzo[d]imidazol-2-yl]thio]propanoic acid (I7);
2-methyl-2-[(1-phenyl-1H-benzo[d]imidazol-2-yl)thio]propanoic acid (I8);
2-methyl-2-[(1-methyl-1H-benzo[d]imidazol-2-yl)thio]propanoic acid (I9);
2-methyl-2-[[1-(4-acetamino-2-fluorophenyl)-1H-benzo[d]imidazol-2-yl)thio]propanoic acid (I10);
2-methyl-2-[[1-(4-bromo-2-fluorophenyl)-1H-benzo[d]imidazol-2-yl]thio]propanoic acid (I11);
2-methyl-2-[[1-(4-chloro-2-fluorophenyl)-1H-benzo[d]imidazol-2-yl]thio]propanoic acid (I12);
2-methyl-2-[[1-(2-fluorophenyl)-1H-benzo[d]imidazol-2-yl]thio]propanoic acid (I13):
Sodium 2-methyl-2-[[5-methoxy-1-(4-cyclopropylnaphth-1-yl)-1H-benzo[d]imidazol-2-yl]thio]propanoate (I14);
Sodium 2-methyl-2-[[1-(4-acetamino-2-fluorophenyl)-1H-benzo[d]imidazol-2-yl]thio]propanoate (I15);
Sodium 2-methyl-2-[[1-(4-bromo-2-fluorophenyl)-1H-benzo[d]imidazol-2-yl]thio]propanoate (I16);
Sodium 2-methyl-2-[[1-(4-nitro-2-fluorophenyl)-1H-benzo[d]imidazol-2-yl]thio]propanoate (I17);
Sodium 2-methyl-2-[[1-(4-cyanophenyl)-1H-benzo[d]imidazol-2-yl]thio]propanoate (I18);
Sodium 2-methyl-2-[[1-(4-cyanonaphth-1-yl)-1H-benzo[d]imidazol-2-yl]thio]propanoate (I19);
Sodium 2-methyl-2-[[1-(4-cyclopropylnaphth-1-yl)-1H-benzo[d]imidazol-2-yl]thio]propanoate (I20); Sodium 2-methyl-2-[(1-methyl-1H-benzo[d]imidazol-2-yl)thio]propanoate (I21);
Sodium 2-methyl-2-[[1-(2-fluorophenyl)-1H-benzo[d]imidazol-2-yl]thio]propanoate (I22);
Sodium 2-methyl-2-[[1-(4-chloro-2-fluorophenyl)-1H-benzo[d]imidazol-2-yl]thio]propanoate (I23);
Sodium 2-methyl-2-[[5-bromo-1-(4-cyanonaphth-1-yl)-1H-benzo[d]imidazol-2-yl]thio]propanoate (I24);
Sodium 2-methyl-2-[(1-phenyl-1H-benzo[d]imidazol-2-yl)thio]propanoate (I25);
Sodium 2-(4-chlorophenyl)-2-[[1-(4-cyclopropylnaphth-1-yl)-1H-benzo[d]imidazol-2-yl]thio]acetate (I26);
Potassium 2-methyl-2-[[5-methoxy-1-(4-cyanonaphth-1-yl)-1H-benzo[d]imidazol-2-yl]thio]propanoate (I27);
Potassium 2-methyl-2-[[1-(4-acetamino-2-fluorophenyl)-1H-benzo[d]imidazol-2-yl]thio]propanoate (I28);
Potassium 2-methyl-2-[[1-(4-bromo-2-fluorophenyl)-1H-benzo[d]imidazol-2-yl]thio]propanoate (I29);
Potassium 2-methyl-2-[[1-(4-nitro-2-fluorophenyl)-1H-benzo[d]imidazol-2-yl]thio]propanoate (I30);
Potassium 2-methyl-2-[[1-(4-cyanophenyl)-1H-benzo[d]imidazol-2-yl]thio]propanoate (I31);
Potassium 2-methyl-2-[[1-(4-cyano-1-naphth-1-yl)-1H-benzo[d]imidazol-2-yl]thio]propanoate (I32);
Potassium 2-methyl-2-[[1-(4-cyclopropylnaphth-1-yl)-1H-benzo[d]imidazol-2-yl]thio]propanoate (I33);
Potassium 2-methyl-2-[(1-methyl-1H-benzo[d]imidazol-2-yl)thio]propanoate (I34);
Potassium 2-methyl-2-[[1-(2-fluorophenyl)-1H-benzo[d]imidazol-2-yl]thio]propanoate (I35);
Potassium 2-methyl-2-[[1-(4-chloro-2-fluorophenyl)-1H-benzo[d]imidazol-2-yl]thio]propanoate (I36);
Potassium 2-methyl-2-[[5-bromo-1-(4-cyanonaphth-1-yl)-1H-benzo[d]imidazol-2-yl]thio]propanoate (I37);
Potassium 2-methyl-2-[(1-phenyl-1H-benzo[d]imidazol-2-yl)thio]propanoate (I38);
Potassium 2-(4-chlorophenyl)-2-[[1-(4-cyclopropylnaphth-1-yl)-1H-benzo[d]imidazol-2-yl]thio]acetate (I39);
Methyl 2-methyl-2-[[5-methoxy-1-(4-cyanonaphth-1-yl)-1H-benzo[d]imidazol-2-yl]thio]propanoate (I40);
Methyl 2-methyl-2-[[1-(4-acetamino-2-fluorophenyl)-1H-benzo[d]imidazol-2-yl]thio]propanoate (I41);
Methyl 2-methyl-2-[[1-(4-bromo-2-fluorophenyl)-1H-benzo[d]imidazol-2-yl]thio]propanoate (I42);
Methyl 2-methyl-2-[[1-(4-nitro-2-fluorophenyl)-1H-benzo[d]imidazol-2-yl]thio]propanoate (I43);
Methyl 2-methyl-2-[[1-(4-cyanophenyl)-1H-benzo[d]imidazol-2-yl]thio]propanoate (I44);
Methyl 2-methyl-2-[[1-(4-cyanonaphth-1-yl)-1H-benzo[d]imidazol-2-yl]thio]propanoate (I45);
Methyl 2-methyl-2-[[1-(4-cyclopropylnaphth-1-yl)-1H-benzo[d]imidazol-2-yl]thio]propanoate (I46);
Methyl 2-methyl-2-[(1-methyl-1H-benzo[d]imidazol-2-yl)thio]propanoate (I47);
Methyl 2-methyl-2-[[1-(2-fluorophenyl)-1H-benzo[d]imidazol-2-yl]thio]propanoate (I48);
Methyl 2-methyl-2-[[1-(4-chloro-2-fluorophenyl)-1H-benzo[d]imidazol-2-yl]thio]propanoate (I49);
Methyl 2-methyl-2-[[5-bromo-1-(4-cyanonaphth-1-yl)-1H-benzo[d]imidazol-2-yl]thio]propanoate (I50);
Methyl 2-methyl-2-[(1-phenyl-1H-benzo[d]imidazol-2-yl)thio]propanoate (I51);
Methyl 2-(4-chlorophenyl)-2-[[1-(4-cyclopropylnaphth-1-yl)-1H-benzo[d]imidazol-2-yl]thio]acetate (I52);
Ethyl 2-methyl-2-[[5-methoxy-1-(4-cyanonaphth-1-yl)-1H-benzo[d]imidazol-2-yl]thio]propanoate (I53);
Ethyl 2-methyl-2-[[1-(4-acetamino-2-fluorophenyl)-1H-benzo[d]imidazol-2-yl]thio]propanoate (I54);
Ethyl 2-methyl-2-[[1-(4-bromo-2-fluorophenyl)-1H-benzo[d]imidazol-2-yl]thio]propanoate (I55);
Ethyl 2-methyl-2-[[1-(4-nitro-2-fluorophenyl)-1H-benzo[d]imidazol-2-yl]thio]propanoate (I56);
Ethyl 2-methyl-2-[[1-(4-cyanophenyl)-1H-benzo[d]imidazol-2-yl]thio]propanoate (I57);
Ethyl 2-methyl-2-[[1-(4-cyanonaphth-1-yl)-1H-benzo[d]imidazol-2-yl]thio]propanoate (I58);
Ethyl 2-methyl-2-[[1-(4-cyclopropylnaphth-1-yl)-1H-benzo[d]imidazol-2-yl]thio]propanoate (I59);
Ethyl 2-methyl-2-[(1-methyl-1H-benzo[d]imidazol-2-yl)thio]propanoate (I60);
Ethyl 2-methyl-2-[[1-(2-fluorophenyl)-1H-benzo[d]imidazol-2-yl]thio]propanoate (I61);
Ethyl 2-methyl-2-[[1-(4-chloro-2-fluorophenyl)-1H-benzo[d]imidazol-2-yl]thio]propanoate (I62);

Ethyl 2-methyl-2-[[5-bromo-1-(4-cyanonaphth-1-yl)-1H-benzo[d]imidazol-2-yl]thio]propanoate (I63);
Ethyl 2-methyl-2-[(1-phenyl-1H-benzo[d]imidazol-2-yl)thio]propanoate (I64);
Ethyl 2-(4-chlorophenyl)-2-[[1-(4-cyclopropylnaphth-1-yl)-1H-benzo[d]imidazol-2-yl]thio]acetate (I65);
(5-methyl-2-oxo-1,3-dioxol-4-yl)methyl 2-methyl-2-[[5-methoxy-1-(4-cyanonaphth-1-yl)-1H-benzo[d]imidazol-2-yl]thio]propanoate (I66);
(5-methyl-2-oxo-1,3-dioxol-4-yl)methyl 2-methyl-2-[[1-(4-acetamino-2-fluorophenyl)-1H-benzo[d]imidazol-2-yl]thio]propanoate (I67);
(5-methyl-2-oxo-1,3-dioxol-4-yl)methyl 2-methyl-2-[[1-(4-bromo-2-fluorophenyl)-1H-benzo[d]imidazol-2-yl]thio]propanoate (I68);
(5-methyl-2-oxo-1,3-dioxol-4-yl)methyl 2-methyl-2-[[1-(4-nitro-2-fluorophenyl)-1H-benzo[d]imidazol-2-yl]thio]propanoate (I69);
(5-methyl-2-oxo-1,3-dioxol-4-yl)methyl 2-methyl-2-[[1-(4-cyanophenyl)-1H-benzo[d]imidazol-2-yl]thio]propanoate (I70);
(5-methyl-2-oxo-1,3-dioxol-4-yl)methyl 2-methyl-2-[[1-(4-cyanonaphth-1-yl)-1H-benzo[d]imidazol-2-yl]thio]propanoate (I71);
(5-methyl-2-oxo-1,3-dioxol-4-yl)methyl 2-methyl-2-[[1-(4-cyclopropylnaphth-1-yl)-1H-benzo[d]imidazol-2-yl]thio]propanoate (I72);
(5-methyl-2-oxo-1,3-dioxol-4-yl)methyl 2-methyl-2-[(1-methyl-1H-benzo[d]imidazol-2-yl)thio]propanoate (I73);
(5-methyl-2-oxo-1,3-dioxol-4-yl)methyl 2-methyl-2-[[1-(2-fluorophenyl)-1H-benzo[d]imidazol-2-yl]thio]propanoate (I74);
(5-methyl-2-oxo-1,3-dioxol-4-yl)methyl 2-methyl-2-[[1-(4-chloro-2-fluorophenyl)-1H-benzo[d]imidazol-2-yl]thio]propanoate (I75);
(5-methyl-2-oxo-1,3-dioxol-4-yl)methyl 2-methyl-2-[[5-bromo-1-(4-cyanonaphth-1-yl)-1H-benzo[d]imidazol-2-yl]thio]propanoate (I76);
(5-methyl-2-oxo-1,3-dioxol-4-yl)methyl 2-methyl-2-[(1-phenyl-1H-benzo[d]imidazol-2-yl)thio]propanoate (I77); and
(5-methyl-2-oxo-1,3-dioxol-4-yl)methyl 2-(4-chlorophenyl)-2-[[1-(4-cyclopropylnaphth-1-yl)-1H-benzo[d]imidazol-2-yl]thio]acetate (I78).

The corresponding structural formulae for the benzimidazole derivatives of this invention, its pharmaceutically acceptable salts, solvates, hydrates, optical isomers and pharmaceutically acceptable prodrugs are as follows:

| No. | Structure |
|---|---|
| I1 | (5-methoxybenzimidazole with N-(4-cyanonaphth-1-yl), S-C(CH3)2COOH) |
| I2 | (benzimidazole with N-(4-cyanonaphth-1-yl), S-C(CH3)2COOH) |
| I3 | (5-bromobenzimidazole with N-(4-cyanonaphth-1-yl), S-C(CH3)2COOH) |
| I4 | (benzimidazole with N-(4-cyanophenyl), S-C(CH3)2COOH) |
| I5 | (benzimidazole with N-(4-cyclopropylnaphth-1-yl), S-C(CH3)2COOH) |

| No. | Structure |
|---|---|
| I6 | 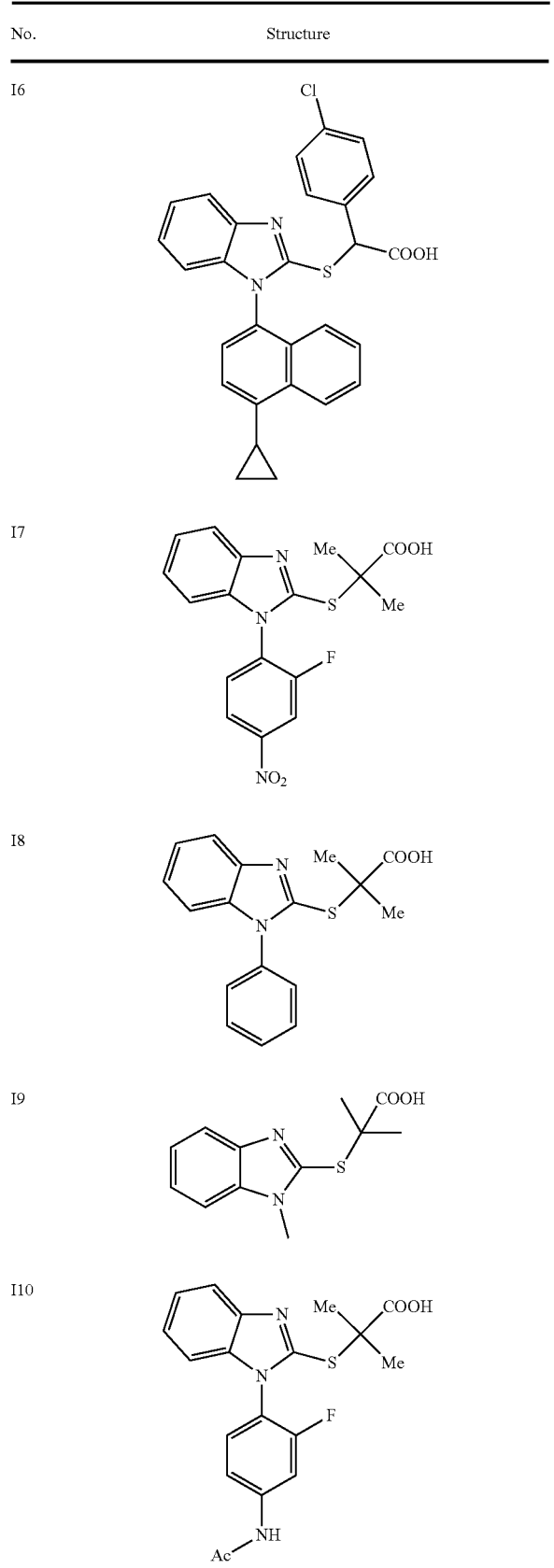 |
| I7 | |
| I8 | |
| I9 | |
| I10 | |
| No. | Structure |
|---|---|
| I11 | 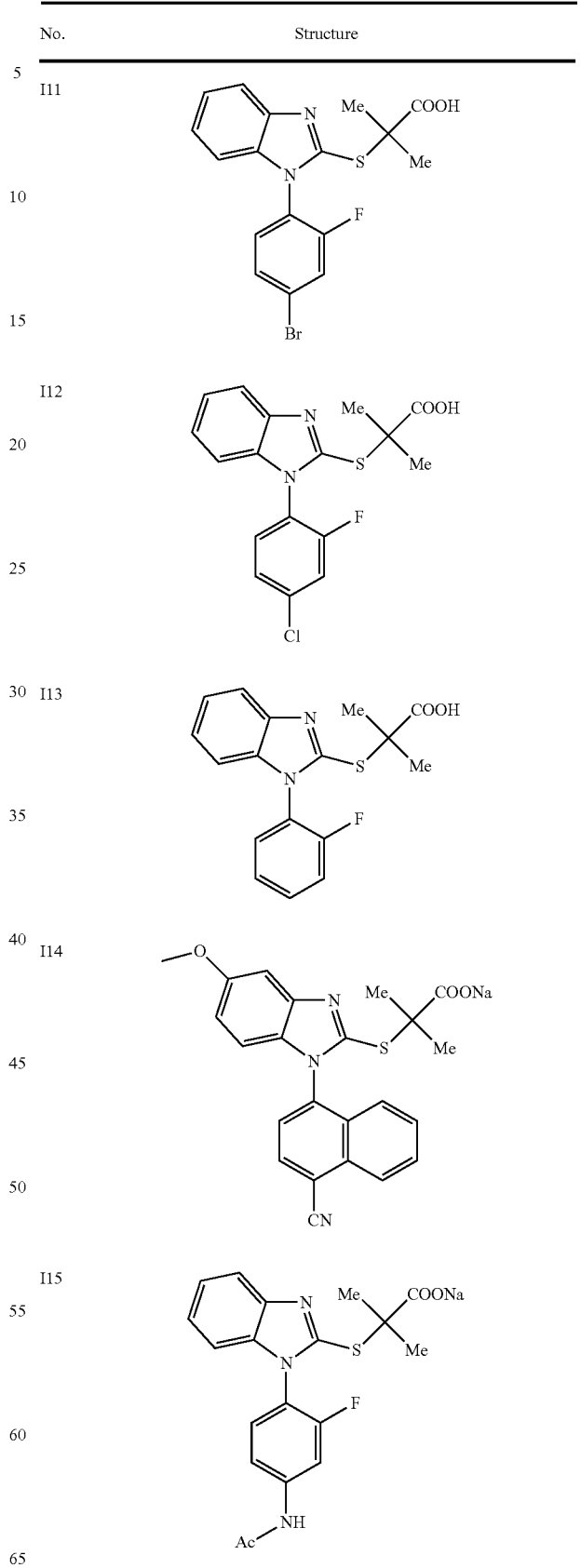 |
| I12 | |
| I13 | |
| I14 | |
| I15 | |

| No. | Structure |
|---|---|
| I16 | 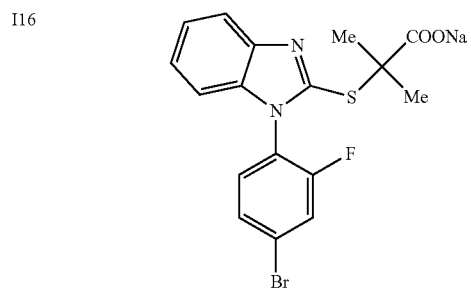 |
| I17 | 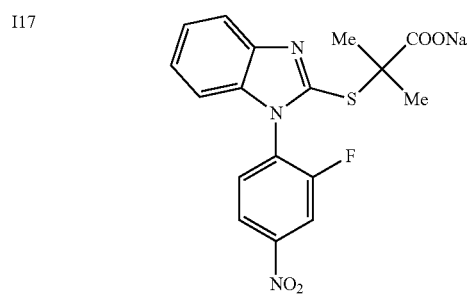 |
| I18 | 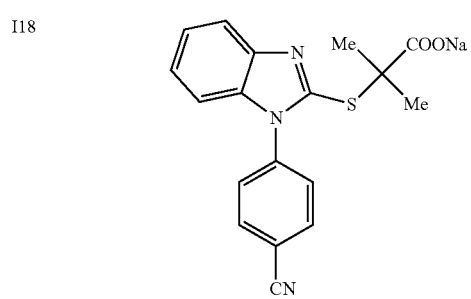 |
| I19 | 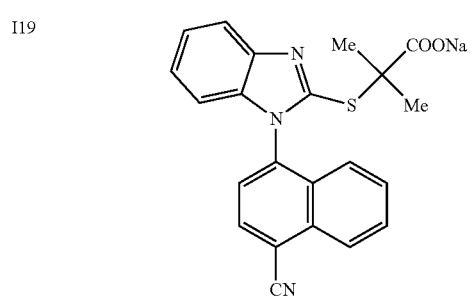 |
| I20 | 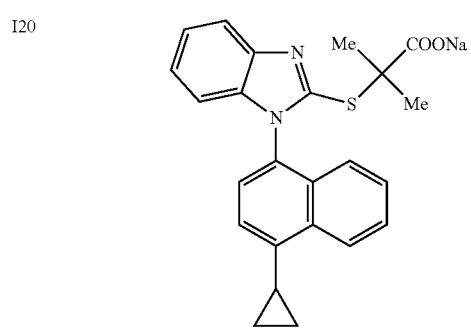 |
| No. | Structure |
|---|---|
| I21 | 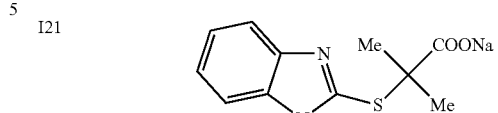 |
| I22 | 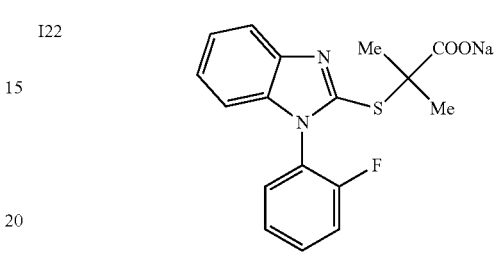 |
| I23 | 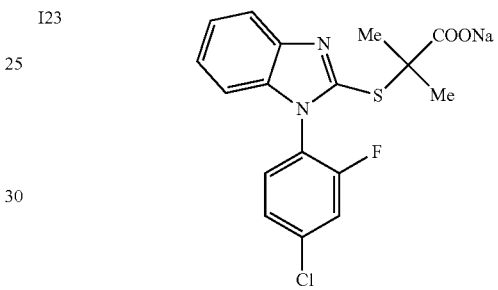 |
| I24 | 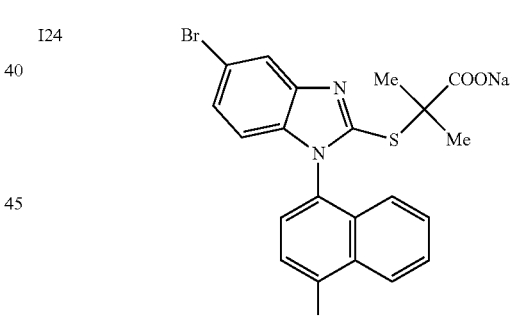 |
| I25 | 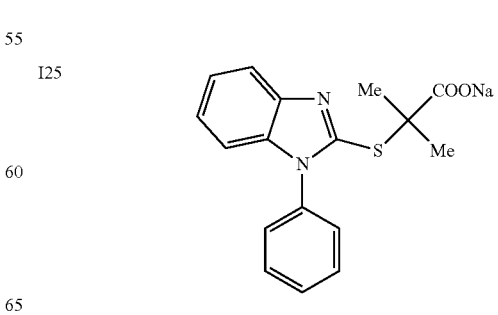 |

| No. | Structure |
|---|---|
| I26 | 4-chlorophenyl-benzimidazole-S-CH(COONa), N-(4-cyclopropylnaphthalen-1-yl) |
| I27 | 5-methoxy-benzimidazole-2-S-C(Me)(Me)-COOK, N-(4-cyanonaphthalen-1-yl) |
| I28 | benzimidazole-2-S-C(Me)(Me)-COOK, N-(3-fluoro-4-acetamidophenyl) |
| I29 | benzimidazole-2-S-C(Me)(Me)-COOK, N-(4-bromo-2-fluorophenyl) |
| I30 | benzimidazole-2-S-C(Me)(Me)-COOK, N-(2-fluoro-4-nitrophenyl) |
| I31 | benzimidazole-2-S-C(Me)(Me)-COOK, N-(4-cyanophenyl) |
| I32 | benzimidazole-2-S-C(Me)(Me)-COOK, N-(4-cyanonaphthalen-1-yl) |
| I33 | benzimidazole-2-S-C(Me)(Me)-COOK, N-(4-cyclopropylnaphthalen-1-yl) |
| I34 | benzimidazole-2-S-C(Me)(Me)-COOK, N-methyl |
| I35 | benzimidazole-2-S-C(Me)(Me)-COOK, N-(2-fluorophenyl) |

| No. | Structure |
|---|---|
| I36 | 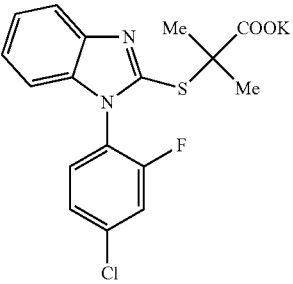 |
| I37 | 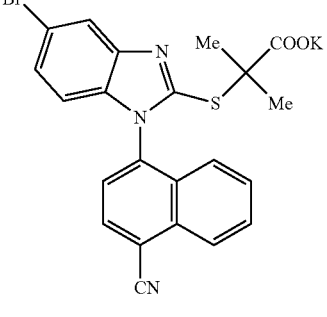 |
| I38 | 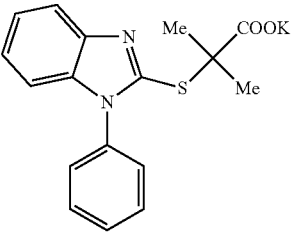 |
| I39 | 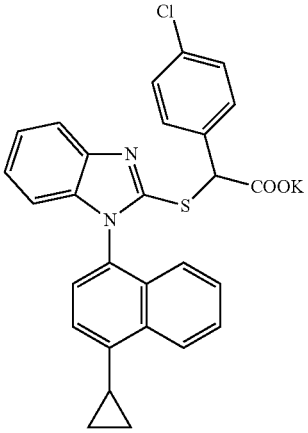 |
| I40 | 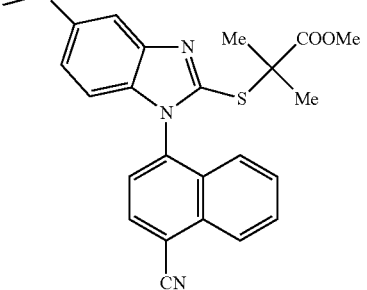 |
| I41 | 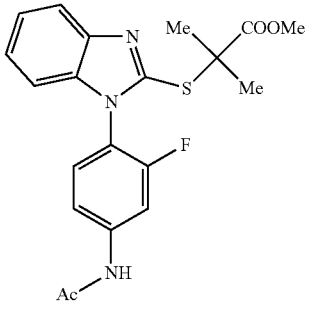 [SMILES: COC(=O)C(C)(C)Sc1nc2ccccc2n1-c1ccc(NC(C)=O)cc1F] |
| I42 | 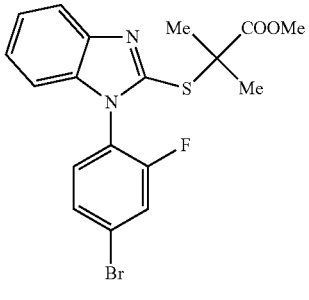 [SMILES: COC(=O)C(C)(C)Sc1nc2ccccc2n1-c1ccc(Br)cc1F] |
| I43 | 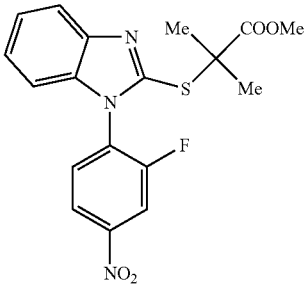 [SMILES: COC(=O)C(C)(C)Sc1nc2ccccc2n1-c1ccc([N+](=O)[O-])cc1F] |
| I44 | 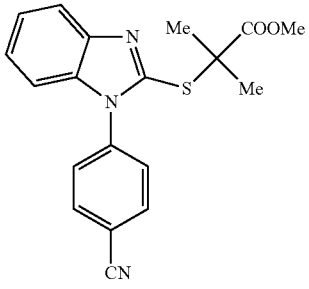 [SMILES: COC(=O)C(C)(C)Sc1nc2ccccc2n1-c1ccc(C#N)cc1] |

| No. | Structure |
|---|---|
| I45 | 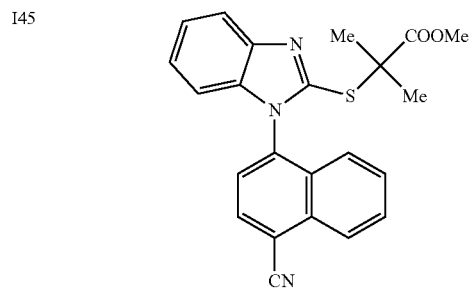 |
| I46 | 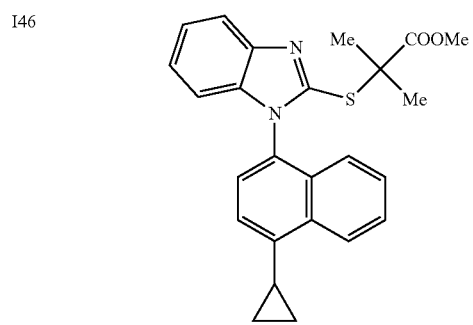 |
| I47 | 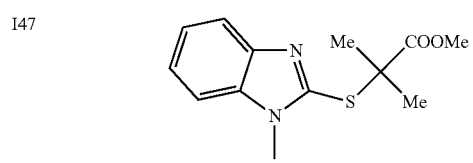 |
| I48 | 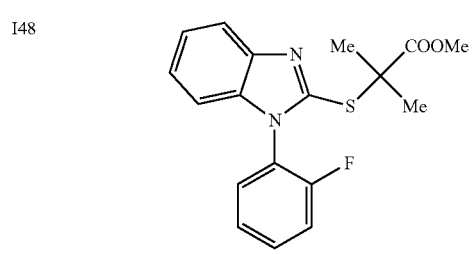 |
| I49 | 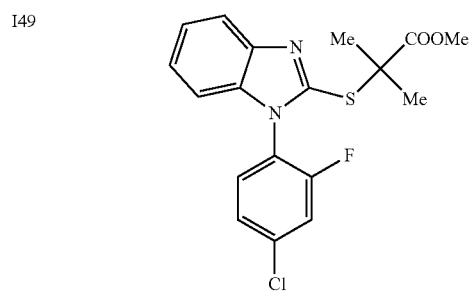 |
| No. | Structure |
|---|---|
| I50 | 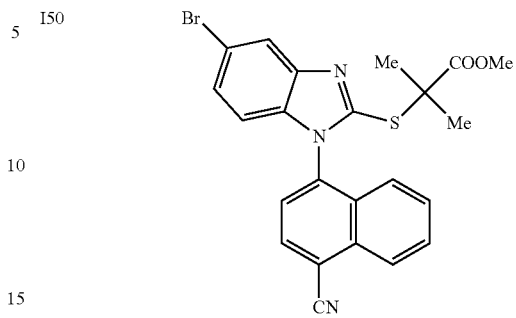 |
| I51 | 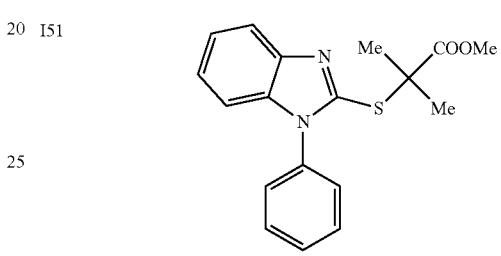 |
| I52 | 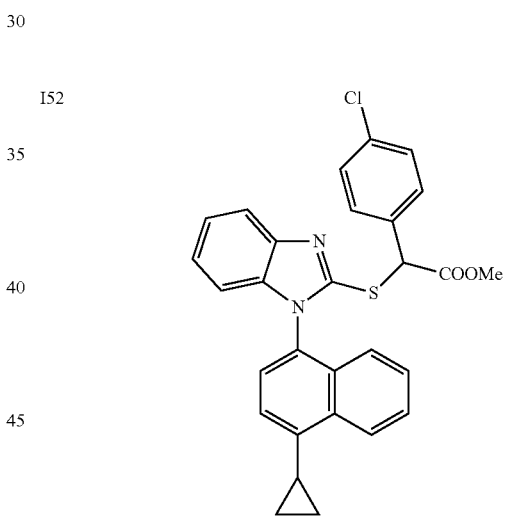 |
| I53 | 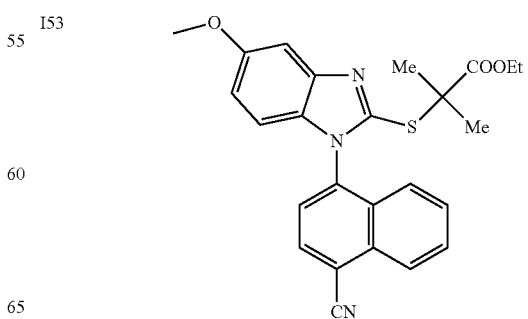 |

| No. | Structure |
|---|---|
| I54 | 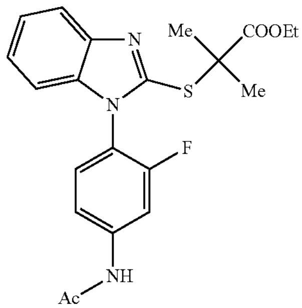 [SMILES: CCOC(=O)C(C)(C)Sc1nc2ccccc2n1-c1ccc(NC(C)=O)cc1F] |
| I55 | 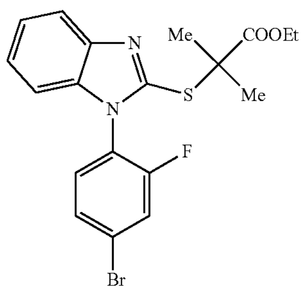 [SMILES: CCOC(=O)C(C)(C)Sc1nc2ccccc2n1-c1ccc(Br)cc1F] |
| I56 | 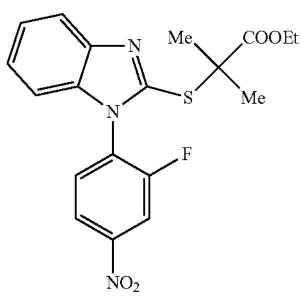 [SMILES: CCOC(=O)C(C)(C)Sc1nc2ccccc2n1-c1ccc([N+](=O)[O-])cc1F] |
| I57 | 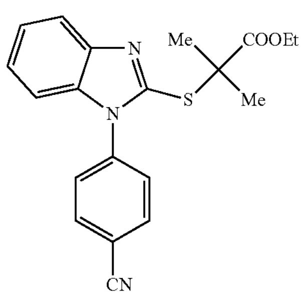 [SMILES: CCOC(=O)C(C)(C)Sc1nc2ccccc2n1-c1ccc(C#N)cc1] |
| I58 | 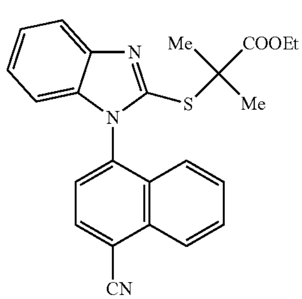 [SMILES: CCOC(=O)C(C)(C)Sc1nc2ccccc2n1-c1ccc(C#N)c2ccccc12] |
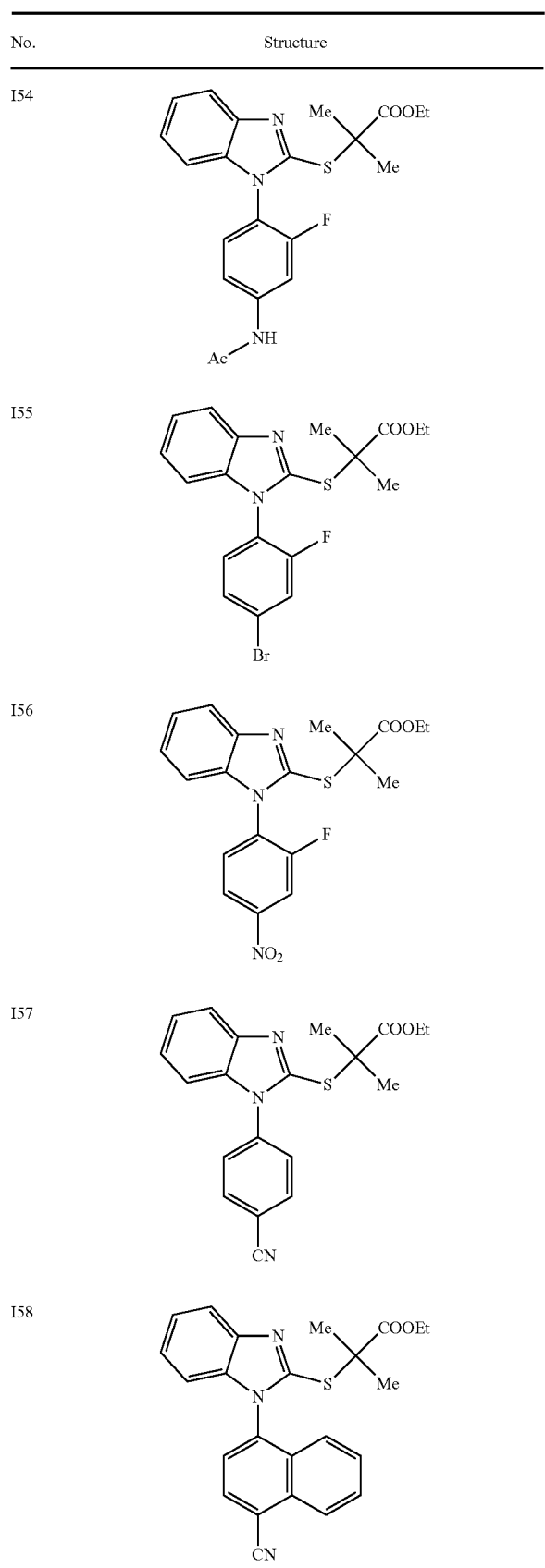
| No. | Structure |
|---|---|
| I59 | 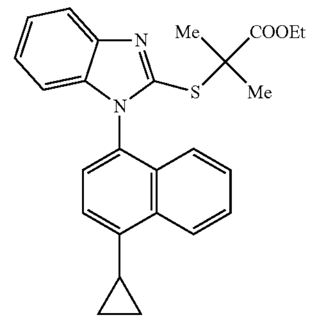 [SMILES: CCOC(=O)C(C)(C)Sc1nc2ccccc2n1-c1ccc(C2CC2)c2ccccc12] |
| I60 | 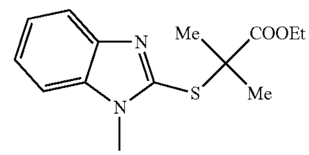 [SMILES: CCOC(=O)C(C)(C)Sc1nc2ccccc2n1C] |
| I61 | 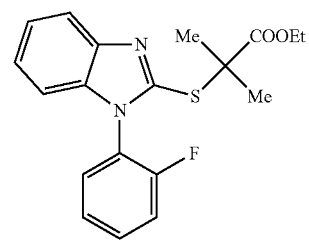 [SMILES: CCOC(=O)C(C)(C)Sc1nc2ccccc2n1-c1ccccc1F] |
| I62 | 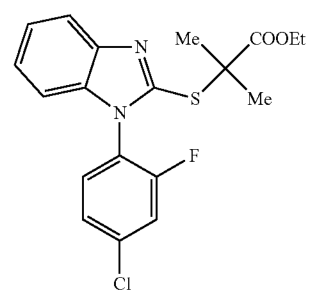 [SMILES: CCOC(=O)C(C)(C)Sc1nc2ccccc2n1-c1ccc(Cl)cc1F] |
| I63 | 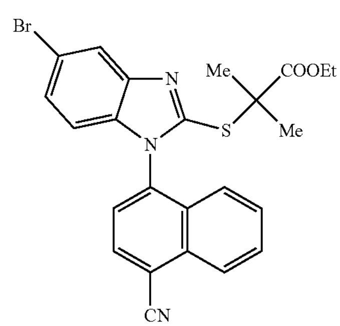 [SMILES: CCOC(=O)C(C)(C)Sc1nc2cc(Br)ccc2n1-c1ccc(C#N)c2ccccc12] |
| I64 | 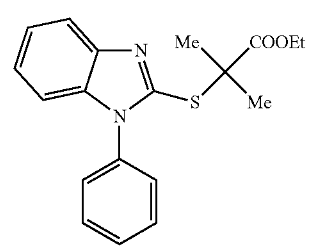 [SMILES: CCOC(=O)C(C)(C)Sc1nc2ccccc2n1-c1ccccc1] |
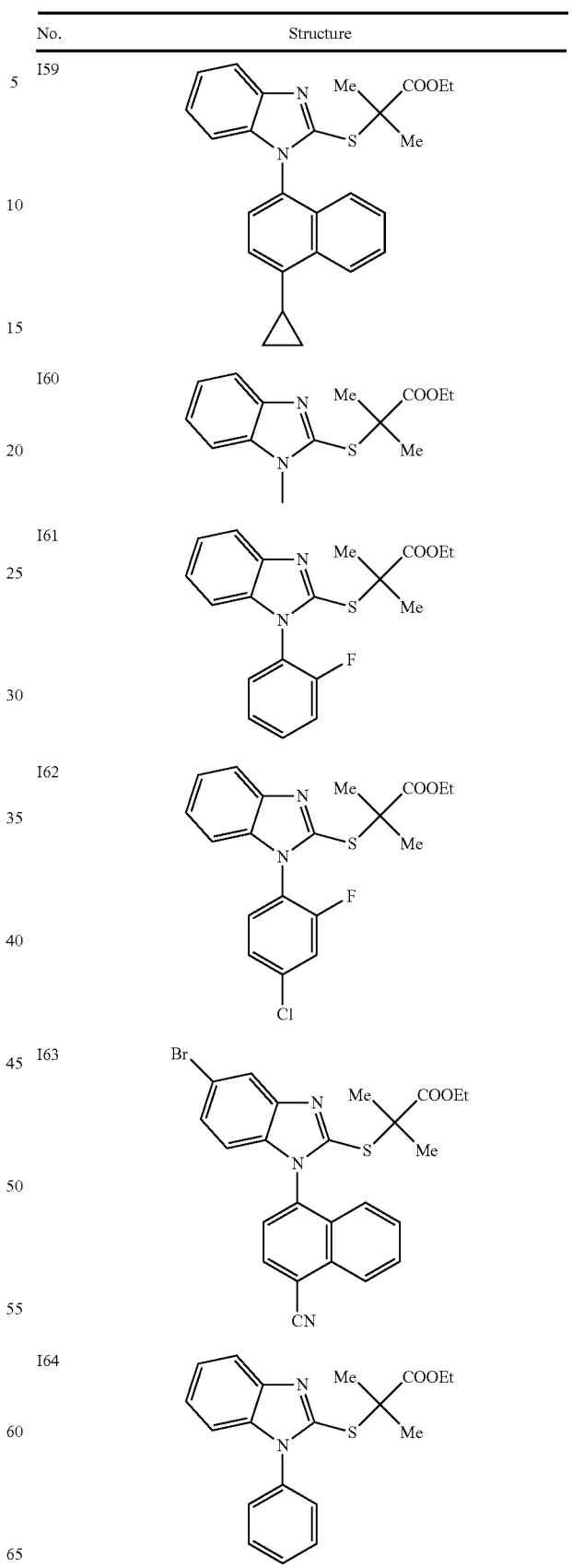

| No. | Structure |
|-----|-----------|
| I65 | |
| I66 | |
| I67 | |
| I68 | |
| I69 | 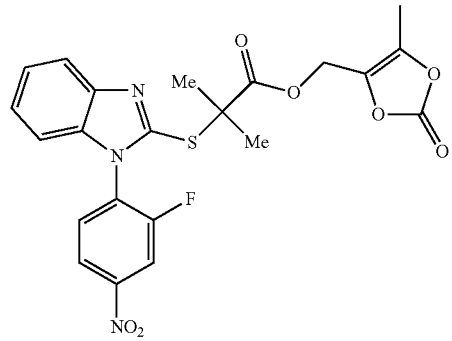 [SMILES: Cc1oc(=O)oc1COC(=O)C(C)(C)Sc1nc2ccccc2n1-c1ccc([N+](=O)[O-])cc1F] |
| I70 | 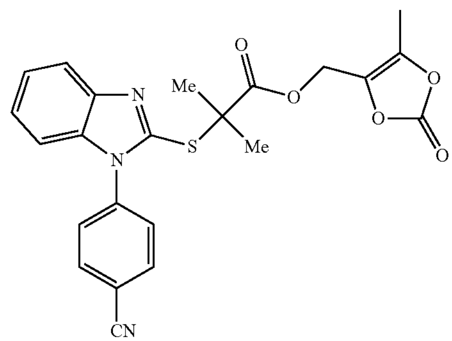 [SMILES: Cc1oc(=O)oc1COC(=O)C(C)(C)Sc1nc2ccccc2n1-c1ccc(C#N)cc1] |
| I71 | 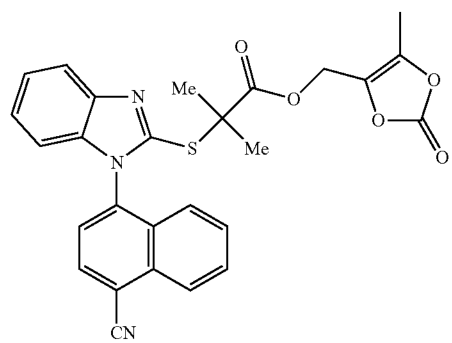 [SMILES: Cc1oc(=O)oc1COC(=O)C(C)(C)Sc1nc2ccccc2n1-c1ccc(C#N)c2ccccc12] |
| I72 | 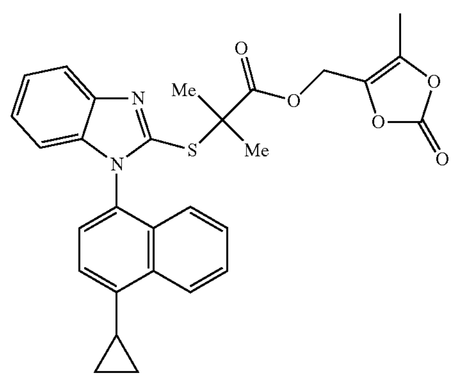 [SMILES: Cc1oc(=O)oc1COC(=O)C(C)(C)Sc1nc2ccccc2n1-c1ccc(C2CC2)c2ccccc12] |
| I73 | 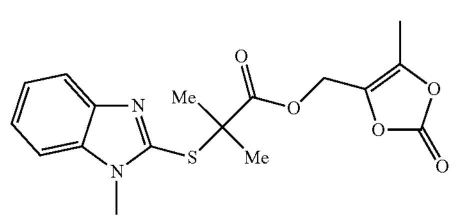 [SMILES: Cc1oc(=O)oc1COC(=O)C(C)(C)Sc1nc2ccccc2n1C] |

| No. | Structure |
|---|---|
| I74 | 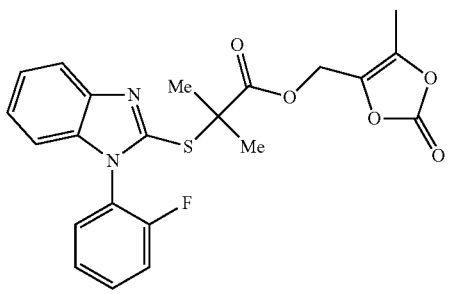 [SMILES: Cc1oc(=O)oc1COC(=O)C(C)(C)Sc1nc2ccccc2n1-c1ccccc1F] |
| I75 | 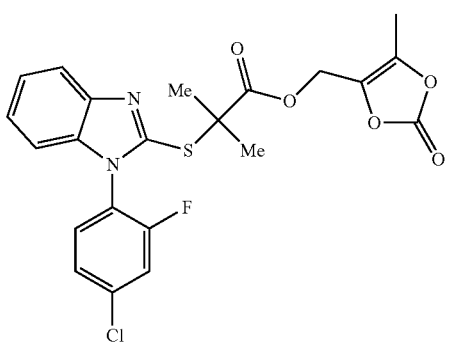 [SMILES: Cc1oc(=O)oc1COC(=O)C(C)(C)Sc1nc2ccccc2n1-c1ccc(Cl)cc1F] |
| I76 | 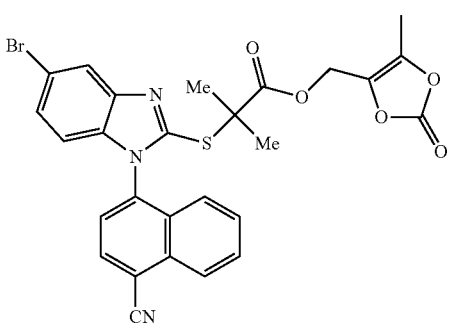 [SMILES: Cc1oc(=O)oc1COC(=O)C(C)(C)Sc1nc2cc(Br)ccc2n1-c1ccc(C#N)c2ccccc12] |
| I77 | 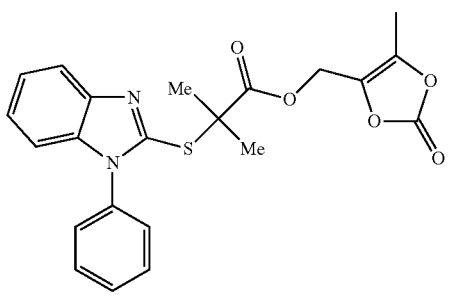 [SMILES: Cc1oc(=O)oc1COC(=O)C(C)(C)Sc1nc2ccccc2n1-c1ccccc1] |

| No. | Structure |
|---|---|
| I78 | 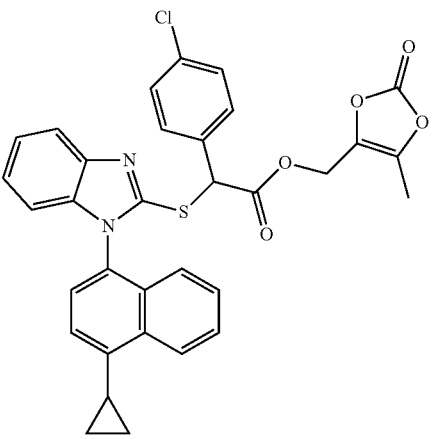 [SMILES: Cc1oc(=O)oc1COC(=O)C(Sc1nc2ccccc2n1-c1ccc(C2CC2)c2ccccc12)c1ccc(Cl)cc1] |

The pharmaceutically acceptable salts of the benzimidazole derivatives of this invention include, but are not limited to, salts of Na, K, Li, Mg, Ca and Zn.

The pharmaceutically acceptable prodrugs of the benzimidazole derivatives of this invention include, but are not limited to, esters, carbonates, thiocarbonates, N-acyl derivatives, N-acyloxy derivatives, amino acid conjugates and etc.

The second object of the present invention to provide methods to prepare the benzimidazole derivatives represented by Formula (I) or their pharmaceutically acceptable salts.

The preparation methods in the present invention comprise the following steps:

(1) Reacting a compound of Formula (II) with a compound of Formula (III) in the presence of a base to form a compound of Formula (IV):

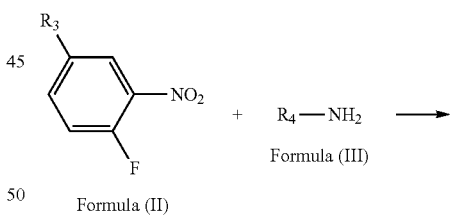

Formula (II)    Formula (III)

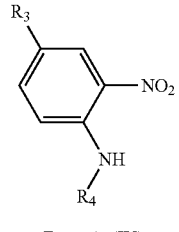

Formula (IV)

(2) Reacting said compound of Formula (IV) with a reducing agent to form a compound of Formula (V):

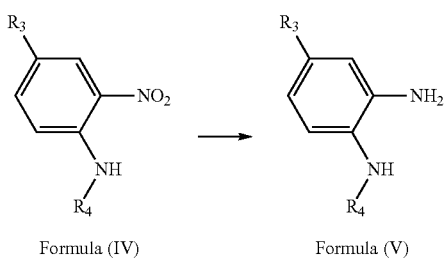

Formula (IV) → Formula (V)

(3) Reacting said compound of Formula (V) with thiophosgene to form a compound of Formula (VI):

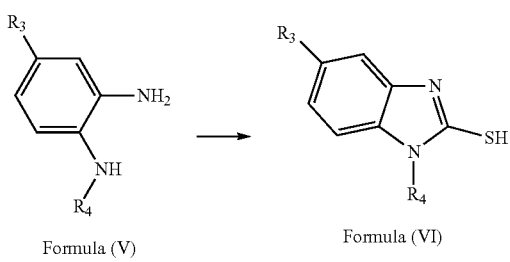

Formula (V) → Formula (VI)

(4) Reacting said compound of Formula (VI) with a compound of Formula (VII) under basic condition to form a compound of Formula (VIII):

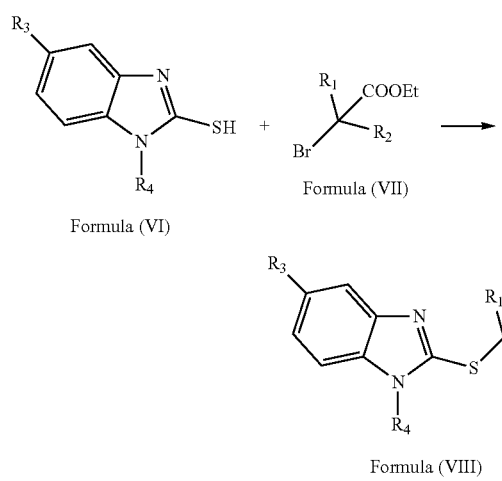

Formula (VI) + Formula (VII) → Formula (VIII)

(5) Hydrolyzing said compound of Formula (VIII) under basic condition to form a compound of Formula (IX):

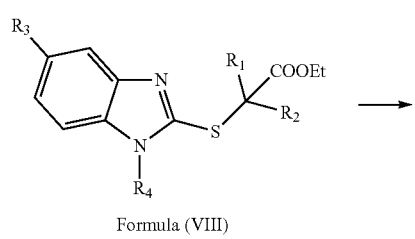

Formula (VIII) →

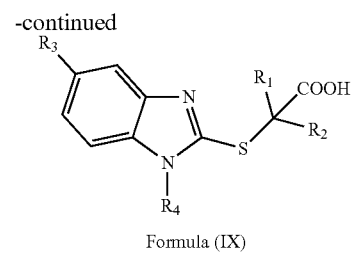

Formula (IX)

(6) Reacting said compound of Formula (IX) with a base to form a compound of Formula (X):

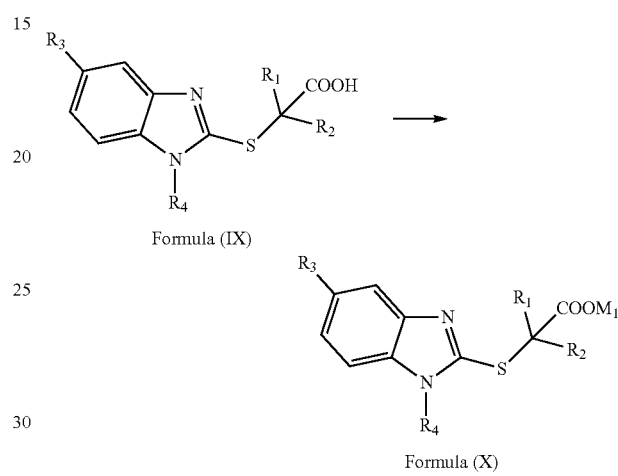

Formula (IX) → Formula (X)

wherein $M_1$ is a pharmaceutically acceptable cation;

(7) Acylating said compound of Formula (IX) using oxalyl chloride, followed by reacting with an alcohol or amine to form a compound of Formula (XI):

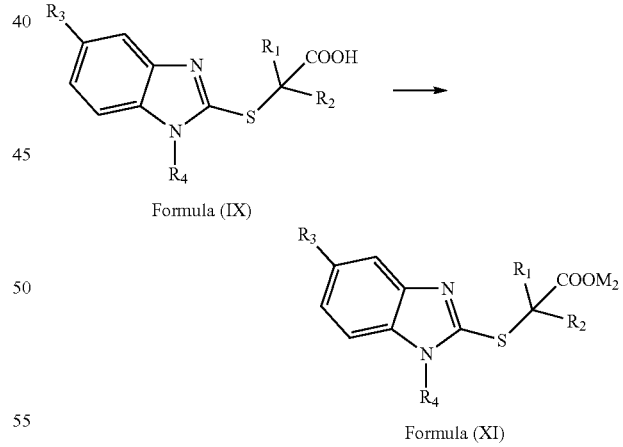

Formula (IX) → Formula (XI)

wherein $M_2$ is $C_{1-3}$ alkyl, amino or ester group.

The third object of the present invention is to provide a pharmaceutical composition comprising at least one of the benzimidazole derivatives represented by Formula (I) or its pharmaceutically acceptable salts.

One or more pharmaceutically acceptable carriers or excipients can be introduced into the pharmaceutical composition of the present invention according to the needs.

In the pharmaceutical composition of this invention, the benzimidazole derivatives represented by Formula (I) or its pharmaceutically acceptable salts can make up 0.1-99.9% by mass with the remaining being the pharmaceutically acceptable carriers.

The pharmaceutical composition of the present invention can be prepared into any pharmaceutically acceptable form including tablets, sugarcoated tablets, film coated tablets, enteric coated tablets, capsules, hard capsules, soft capsules, oral liquids, buccal tablets, granules, electuaries, pills, powder, ointments, pellets, suspensions, dust powder, solutions, injectables, suppositories, soft ointments, plasters, creams, sprays, drops and patches. Orally administered forms are preferred for the present invention, including capsules, buccal tablets, oral liquids, enteric coated tablets, pills, powder, pellets, ointments, etc.

The present invention is administered orally, parenterally or topically with oral and injection preferred. Suitable oral administration forms can be tablets, capsules, granules or other pharmaceutical liquid forms such as solutions, emulsions, suspensions, etc. The preferable oral form is tablets, which can be further prepared as film coated tablets, enteric coated tablets, sustained release or controlled release forms.

When in an orally administered form, the pharmaceutical composition of this invention may comprise conventional excipients such as binders, fillers, thinners, tableting agents, lubricants, disintegrants, coloring agents, flavoring agents and wetting agents. Tablets can be coated when necessary.

Suitable fillers comprise cellulose, mannitol, lactose, and other similar fillers. Suitable disintegrants comprise starch, polyvinylpyrrolidone and starch derivatives such as sodium starch glycolate. Suitable lubricants comprise magnesium stearate. Suitable pharmaceutically acceptable wetting agents comprise sodium lauryl sulfate.

Orally administered compositions in solid form can be prepared by conventional methods comprising mixing, filling, tableting, etc. Repeated mixing can distribute the active substances throughout those compositions that use large amounts of fillers.

The orally administered liquid forms can be in the form of aqueous or oily suspensions, solutions, emulsions, syrups or elixirs, or can be a dried product to be reconstituted with water or other suitable carriers before administration. The liquid forms can contain conventional additives, such as suspending agents like sorbitol, syrup, methyl cellulose, gelatin, hydroxyethyl cellulose, carboxymethyl cellulose, aluminum stearate gel, or hydrogenated edible fat; emulsifiers like lecithin, sorbitan monooleate or acacia; non-aqueous carriers (which may include edible oils) like almond oil, fractionated coconut oil; oil esters such as esters of glycerol, propylene glycol or ethanol; preservatives such as methyl p-hydroxybenzoate, propyl p-hydroxybenzoate or sorbic acid, and if necessary, may contain conventional flavoring or coloring agents.

Injections are prepared in liquid form with each unit comprising the active substances of this invention and a sterile carrier. The compound can be suspended or dissolved depending on the carrier and concentration. Solutions are usually prepared by dissolving the active substance in a carrier, filtering and sterilizing it before filling it into a suitable vial or ampoule, and the vial or ampoule is subsequently sealed. Excipients such as a local anesthetic, preservatives and buffers can also be dissolved in such carrier. To increase its stability, this composition can be frozen after filling into a vial and vacuum dried.

Suitable pharmaceutically acceptable carrier can be selectively added to the pharmaceutical composition of the present invention when preparing the drug. The pharmaceutically acceptable carrier is selected from the group consisting of mannitol, sorbitol, sodium metabisulfite, sodium bisulfite, and sodium thiosulphate, cysteine hydrochloride, thioglycolic acid, methionine, vitamin C, disodium EDTA, sodium calcium EDTA, monovalent alkali metal carbonates, acetates, phosphates or aqueous solutions thereof, hydrochloric acid, acetic acid, sulfuric acid, phosphoric acid, amino acids, sodium chloride, potassium chloride, sodium lactate, xylitol, maltose, glucose, fructose, dextran, glycine, starch, sucrose, lactose, mannitol, silicon derivatives, cellulose and their derivatives, alginates, gelatin, polyvinylpyrrolidone, glycerol, Tween 80, agar, calcium carbonate, calcium bicarbonate, surfactants, polyethylene glycol, cyclodextrins, β-cyclodextrin, phospholipids, Kaolin, talc, calcium stearate, magnesium stearate, etc.

The compounds of the present invention or their pharmaceutically acceptable salts can be administered alone or in the form of a pharmaceutical composition. The pharmaceutical composition of the present invention can be formulated into various suitable forms according to the route of administration. The use of one or more physiologically acceptable carriers, including excipients and auxiliaries, facilitates processing of the active compounds into forms that can be pharmaceutically used. The route of administration determines the suitable form to be used and be prepared according to common knowledge in the art.

The fourth object of the present invention is to provide uses of the benzimidazole derivatives of this invention, their pharmaceutically acceptable salts or pharmaceutically acceptable prodrugs in preparing a medicament for modulating uric acid levels and/or treating gout.

The fifth object of the present invention is to provide uses of pharmaceutical compositions, with the benzimidazole derivatives of this invention, their pharmaceutically acceptable salts or pharmaceutically acceptable prodrugs as an active ingredient, in preparing a medicament for modulating uric acid levels and/or treating gout.

The indications corresponding to the pharmaceutical use of the present invention are hyperuricemia, gout, gouty arthritis, inflammatory arthritis, nephropathy, nephrolithiasis, joint inflammatory disorder, deposition of urate crystals in joints, urolithiasis, deposition of urate crystals in the renal parenchyma, gout attack, tophaceous gout, or combinations thereof.

The sixth object of the present invention is to provide uses of the benzimidazole derivatives of this invention or their pharmaceutically acceptable salts in combination with a second antigout drug.

The present invention further provides uses of the benzimidazole derivatives of this invention or their pharmaceutically acceptable salts in combination with a second antigout drug as a pharmaceutical composition.

Uses of the pharmaceutical composition of in preparing a medicament for regulating uric acid level and/or treating gout.

The second drug is a URAT1 inhibitor, xanthine oxidase inhibitor, xanthine dehydrogenase, xanthine oxidoreductase inhibitor, purine nucleoside phosphorylase inhibitor, a uric acid transporter inhibitor, glucose transporter inhibitor, organic anion transporter (OAT) inhibitors, OAT-4 inhibitors or any combination thereof. The second drug is preferably allopurinol, febuxostat, tolperistat or any combination thereof.

In comparison to the existing drugs, the drug of the present invention exhibits better therapeutic effect, stronger drug activity, shorter therapeutic duration, quicker response, and fewer adverse effects in treating gout. Moreover, the drug synthesis process is simple with low cost, making it more suitable for mass production.

DESCRIPTION OF THE DRAWINGS

FIG. 1 shows the therapeutic effect of test compounds on hyperuricemia rat models.

DETAILED DESCRIPTION OF THE INVENTION

In one embodiment, this invention provides a benzimidazole derivative having the structure of Formula (I):

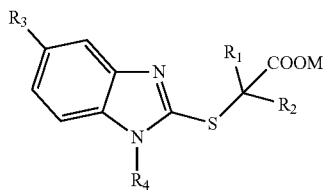

Formula (I)

or a pharmaceutically acceptable salt or prodrug thereof, wherein:
R1 and R2 are selected from the group consisting of hydrogen, alkyl, phenyl and substituted phenyl, wherein the substituent in said substituted phenyl is selected from the group consisting of halogen, cyano, alkyl, alkoxy, ester, N-acyl derivatives, N-acyloxy derivatives and amino acid conjugates;
R3 is selected from the group consisting of hydrogen, halogen, cyano, linear or branched $C_{1-6}$ alkyl and linear or branched $C_{1-6}$ alkoxy;
R4 is selected from the group consisting of alkyl, phenyl, substituted phenyl, naphthyl and substituted naphthyl, wherein the substituent in said substituted phenyl and substituted naphthyl is selected from the group consisting of halogen, cyano, alkyl, alkoxy, ester, N-acyl derivatives, N-acyloxy derivatives and amino acid conjugates; and
M is selected from the group consisting of hydrogen, $C_{1-6}$ alkyl, amino, ester and pharmaceutically acceptable cations.

In one embodiment, said pharmaceutically acceptable salt is selected from the group consisting of Na, K, Li, Ca and Mg salts.

In one embodiment, said pharmaceutically acceptable prodrug is selected from the group consisting of esters, carbonates, thiocarbonates, N-acyl derivatives, N-acyloxy derivatives and amino acid conjugates.

In one embodiment, said benzimidazole derivative is selected from the group consisting of:
2-methyl-2-[[5-methoxy-1-(4-cyanonaphth-1-yl)-1H-benzo [d]imidazol-2-yl]thio]propanoic acid (I1);
2-methyl-2-[[1-(4-cyanonaphth-1-yl)-1H-benzo[d]imidazol-2-yl]thio]propanoic acid (I2);
2-methyl-2-[[5-bromo-1-(4-cyanonaphth-1-yl)-1H-benzo [d]imidazol-2-yl]thio]propanoic acid (I3);
2-methyl-2-[[1-(4-cyanophenyl)-1H-benzo[d]imidazol-2-yl]thio]propanoic acid (I4);
2-methyl-2-[[1-(4-cyclopropylnaphth-1-yl)-1H-benzo[d] imidazol-2-yl]thio]propanoic acid (I5);
2-(4-chlorophenyl)-2-[[1-(4-cyclopropylnaphth-1-yl)-1H-benzo[d]imidazol-2-yl]thio]acetic acid (I6);
2-methyl-2-[[1-(4-nitro-2-fluorophenyl)-1H-benzo[d]imidazol-2-yl]thio]propanoic acid (I7);
2-methyl-2-[(1-phenyl-1H-benzo[d]imidazol-2-yl)thio]propanoic acid (I8);
2-methyl-2-[(1-methyl-1H-benzo[d]imidazol-2-yl)thio]propanoic acid (I9);
2-methyl-2-[[1-(4-acetamino-2-fluorophenyl)-1H-benzo[d] imidazol-2-yl)thio]propanoic acid (I10);
2-methyl-2-[[1-(4-bromo-2-fluorophenyl)-1H-benzo[d]imidazol-2-yl]thio]propanoic acid (I11);
2-methyl-2-[[1-(4-chloro-2-fluorophenyl)-1H-benzo[d]imidazol-2-yl]thio]propanoic acid (I12);
2-methyl-2-[[1-(2-fluorophenyl)-1H-benzo[d]imidazol-2-yl]thio]propanoic acid (I13):
Sodium 2-methyl-2-[[5-methoxy-1-(4-cyclopropylnaphth-1-yl)-1H-benzo[d]imidazol-2-yl]thio]propanoate (I14);
Sodium 2-methyl-2-[[1-(4-acetamino-2-fluorophenyl)-1H-benzo[d]imidazol-2-yl]thio]propanoate (I15);
Sodium 2-methyl-2-[[1-(4-bromo-2-fluorophenyl)-1H-benzo[d]imidazol-2-yl]thio]propanoate (I16);
Sodium 2-methyl-2-[[1-(4-nitro-2-fluorophenyl)-1H-benzo [d]imidazol-2-yl]thio]propanoate (I17);
Sodium 2-methyl-2-[[1-(4-cyanophenyl)-1H-benzo[d]imidazol-2-yl]thio]propanoate (I18);
Sodium 2-methyl-2-[[1-(4-cyanonaphth-1-yl)-1H-benzo[d] imidazol-2-yl]thio]propanoate (I19);
Sodium 2-methyl-2-[[1-(4-cyclopropylnaphth-1-yl)-1H-benzo[d]imidazol-2-yl]thio]propanoate (I20);
Sodium 2-methyl-2-[(1-methyl-1H-benzo[d]imidazol-2-yl) thio]propanoate (I21);
Sodium 2-methyl-2-[[1-(2-fluorophenyl)-1H-benzo[d]imidazol-2-yl]thio]propanoate (I22);
Sodium 2-methyl-2-[[1-(4-chloro-2-fluorophenyl)-1H-benzo[d]imidazol-2-yl]thio]propanoate (I23);
Sodium 2-methyl-2-[[5-bromo-1-(4-cyanonaphth-1-yl)-1H-benzo[d]imidazol-2-yl]thio]propanoate (I24);
Sodium 2-methyl-2-[(1-phenyl-1H-benzo[d]imidazol-2-yl) thio]propanoate (I25);
Sodium 2-(4-chlorophenyl)-2-[[1-(4-cyclopropylnaphth-1-yl)-1H-benzo[d]imidazol-2-yl]thio]acetate (I26);
Potassium 2-methyl-2-[[5-methoxy-1-(4-cyanonaphth-1-yl)-1H-benzo[d]imidazol-2-yl]thio]propanoate (I27);
Potassium 2-methyl-2-[[1-(4-acetamino-2-fluorophenyl)-1H-benzo[d]imidazol-2-yl]thio]propanoate (I28);
Potassium 2-methyl-2-[[1-(4-bromo-2-fluorophenyl)-1H-benzo[d]imidazol-2-yl]thio]propanoate (I29);
Potassium 2-methyl-2-[[1-(4-nitro-2-fluorophenyl)-1H-benzo[d]imidazol-2-yl]thio]propanoate (I30);
Potassium 2-methyl-2-[[1-(4-cyanophenyl)-1H-benzo[d] imidazol-2-yl]thio]propanoate (I31);
Potassium 2-methyl-2-[[1-(4-cyano-1-naphth-1-yl)-1H-benzo[d]imidazol-2-yl]thio]propanoate (I32);
Potassium 2-methyl-2-[[1-(4-cyclopropylnaphth-1-yl)-1H-benzo[d]imidazol-2-yl]thio]propanoate (I33);
Potassium 2-methyl-2-[(1-methyl-1H-benzo[d]imidazol-2-yl)thio]propanoate (I34);
Potassium 2-methyl-2-[[1 I-(2-fluorophenyl)-1H-benzo[d] imidazol-2-yl]thio]propanoate (I35);
Potassium 2-methyl-2-[[1-(4-chloro-2-fluorophenyl)-1H-benzo[d]imidazol-2-yl]thio]propanoate (I36);
Potassium 2-methyl-2-[[5-bromo-1-(4-cyanonaphth-1-yl)-1H-benzo[d]imidazol-2-yl]thio]propanoate (I37);
Potassium 2-methyl-2-[(1-phenyl-1H-benzo[d]imidazol-2-yl)thio]propanoate (I38);
Potassium 2-(4-chlorophenyl)-2-[[1-(4-cyclopropylnaphth-1-yl)-1H-benzo[d]imidazol-2-yl]thio]acetate (I39);
Methyl 2-methyl-2-[[5-methoxy-1-(4-cyanonaphth-1-yl)-1H-benzo[d]imidazol-2-yl]thio]propanoate (I40);

Methyl 2-methyl-2-[[1-(4-acetamino-2-fluorophenyl)-1H-benzo[d]imidazol-2-yl]thio]propanoate (I41);
Methyl 2-methyl-2-[[1-(4-bromo-2-fluorophenyl)-1H-benzo[d]imidazol-2-yl]thio]propanoate (I42);
Methyl 2-methyl-2-[[1-(4-nitro-2-fluorophenyl)-1H-benzo[d]imidazol-2-yl]thio]propanoate (I43);
Methyl 2-methyl-2-[[1-(4-cyanophenyl)-1H-benzo[d]imidazol-2-yl]thio]propanoate (I44);
Methyl 2-methyl-2-[[1-(4-cyanonaphth-1-yl)-1H-benzo[d]imidazol-2-yl]thio]propanoate (I45);
Methyl 2-methyl-2-[[1-(4-cyclopropylnaphth-1-yl)-1H-benzo[d]imidazol-2-yl]thio]propanoate (I46);
Methyl 2-methyl-2-[(1-methyl-1H-benzo[d]imidazol-2-yl)thio]propanoate (I47);
Methyl 2-methyl-2-[[1-(2-fluorophenyl)-1H-benzo[d]imidazol-2-yl]thio]propanoate (I48);
Methyl 2-methyl-2-[[1-(4-chloro-2-fluorophenyl)-1H-benzo[d]imidazol-2-yl]thio]propanoate (I49);
Methyl 2-methyl-2-[[5-bromo-1-(4-cyanonaphth-1-yl)-1H-benzo[d]imidazol-2-yl]thio]propanoate (I50);
Methyl 2-methyl-2-[(1-phenyl-1H-benzo[d]imidazol-2-yl)thio]propanoate (I51);
Methyl 2-(4-chlorophenyl)-2-[[1-(4-cyclopropylnaphth-1-yl)-1H-benzo[d]imidazol-2-yl]thio]acetate (I52);
Ethyl 2-methyl-2-[[5-methoxy-1-(4-cyanonaphth-1-yl)-1H-benzo[d]imidazol-2-yl]thio]propanoate (I53);
Ethyl 2-methyl-2-[[1-(4-acetamino-2-fluorophenyl)-1H-benzo[d]imidazol-2-yl]thio]propanoate (I54);
Ethyl 2-methyl-2-[[1-(4-bromo-2-fluorophenyl)-1H-benzo[d]imidazol-2-yl]thio]propanoate (I55);
Ethyl 2-methyl-2-[[1-(4-nitro-2-fluorophenyl)-1H-benzo[d]imidazol-2-yl]thio]propanoate (I56);
Ethyl 2-methyl-2-[[1-(4-cyanophenyl)-1H-benzo[d]imidazol-2-yl]thio]propanoate (I57);
Ethyl 2-methyl-2-[[1-(4-cyanonaphth-1-yl)-1H-benzo[d]imidazol-2-yl]thio]propanoate (I58);
Ethyl 2-methyl-2-[[1-(4-cyclopropylnaphth-1-yl)-1H-benzo[d]imidazol-2-yl]thio]propanoate (I59);
Ethyl 2-methyl-2-[(1-methyl-1H-benzo[d]imidazol-2-yl)thio]propanoate (I60);
Ethyl 2-methyl-2-[[1-(2-fluorophenyl)-1H-benzo[d]imidazol-2-yl]thio]propanoate (I61);
Ethyl 2-methyl-2-[[1-(4-chloro-2-fluorophenyl)-1H-benzo[d]imidazol-2-yl]thio]propanoate (I62);
Ethyl 2-methyl-2-[[5-bromo-1-(4-cyanonaphth-1-yl)-1H-benzo[d]imidazol-2-yl]thio]propanoate (I63);
Ethyl 2-methyl-2-[(1-phenyl-1H-benzo[d]imidazol-2-yl)thio]propanoate (I64);
Ethyl 2-(4-chlorophenyl)-2-[[1-(4-cyclopropylnaphth-1-yl)-1H-benzo[d]imidazol-2-yl]thio]acetate (I65);
(5-methyl-2-oxo-1,3-dioxol-4-yl)methyl 2-methyl-2-[[5-methoxy-1-(4-cyanonaphth-1-yl)-1H-benzo[d]imidazol-2-yl]thio]propanoate (I66);
(5-methyl-2-oxo-1,3-dioxol-4-yl)methyl 2-methyl-2-[[1-(4-acetamino-2-fluorophenyl)-1H-benzo[d]imidazol-2-yl]thio]propanoate (I67);
(5-methyl-2-oxo-1,3-dioxol-4-yl)methyl 2-methyl-2-[[1-(4-bromo-2-fluorophenyl)-1H-benzo[d]imidazol-2-yl]thio]propanoate (I68);
(5-methyl-2-oxo-1,3-dioxol-4-yl)methyl 2-methyl-2-[[1-(4-nitro-2-fluorophenyl)-1H-benzo[d]imidazol-2-yl]thio]propanoate (I69);
(5-methyl-2-oxo-1,3-dioxol-4-yl)methyl 2-methyl-2-[[1-(4-cyanophenyl)-1H-benzo[d]imidazol-2-yl]thio]propanoate (I70);
(5-methyl-2-oxo-1,3-dioxol-4-yl)methyl 2-methyl-2-[[1-(4-cyanonaphth-1-yl)-1H-benzo[d]imidazol-2-yl]thio]propanoate (I71);
(5-methyl-2-oxo-1,3-dioxol-4-yl)methyl 2-methyl-2-[[1-(4-cyclopropylnaphth-1-yl)-1H-benzo[d]imidazol-2-yl]thio]propanoate (I72);
(5-methyl-2-oxo-1,3-dioxol-4-yl)methyl 2-methyl-2-[(1-methyl-1H-benzo[d]imidazol-2-yl)thio]propanoate (I73);
(5-methyl-2-oxo-1,3-dioxol-4-yl)methyl 2-methyl-2-[[1-(2-fluorophenyl)-1H-benzo[d]imidazol-2-yl]thio]propanoate (I74);
(5-methyl-2-oxo-1,3-dioxol-4-yl)methyl 2-methyl-2-[[1-(4-chloro-2-fluorophenyl)-1H-benzo[d]imidazol-2-yl]thio]propanoate (I75);
(5-methyl-2-oxo-1,3-dioxol-4-yl)methyl 2-methyl-2-[[5-bromo-1-(4-cyanonaphth-1-yl)-1H-benzo[d]imidazol-2-yl]thio]propanoate (I76);
(5-methyl-2-oxo-1,3-dioxol-4-yl)methyl 2-methyl-2-[(1-phenyl-1H-benzo[d]imidazol-2-yl)thio]propanoate (I77); and
(5-methyl-2-oxo-1,3-dioxol-4-yl)methyl 2-(4-chlorophenyl)-2-[[1-(4-cyclopropylnaphth-1-yl)-1H-benzo[d]imidazol-2-yl]thio]acetate (I78).

In one embodiment, this invention provides a method of preparing the benzimidazole derivative of this invention, said method comprising the steps of:

(1) Reacting a compound of Formula (II) with a compound of Formula (III) in the presence of a base to form a compound of Formula (IV);

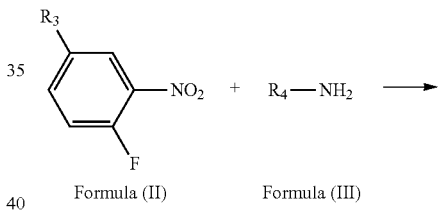

Formula (II)    Formula (III)

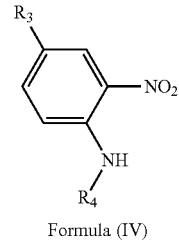

Formula (IV)

(2) Reacting said compound of Formula (IV) with a reducing agent to form a compound of Formula (V);

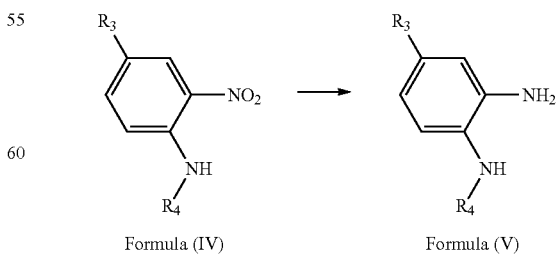

Formula (IV)    Formula (V)

(3) Reacting said compound of Formula compound (V) with thiophosgene to form a compound of Formula (VI);

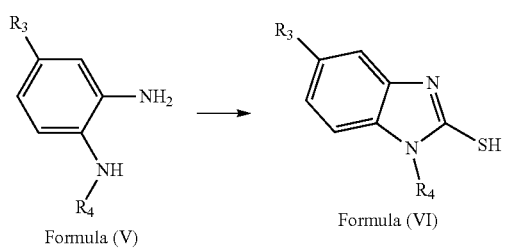

Formula (V) → Formula (VI)

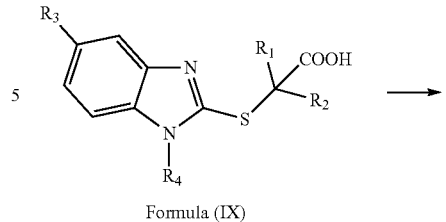

Formula (IX)

(4) Reacting said compound of Formula (VI) with a compound of Formula (VII) under basic condition to form a compound of Formula (VIII);

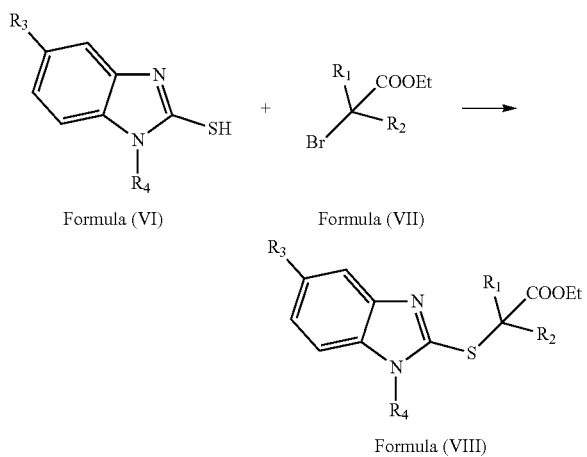

Formula (VI) + Formula (VII) → Formula (VIII)

(5) Hydrolyzing said compound of Formula (VIII) under basic condition to form a compound of Formula (IX);

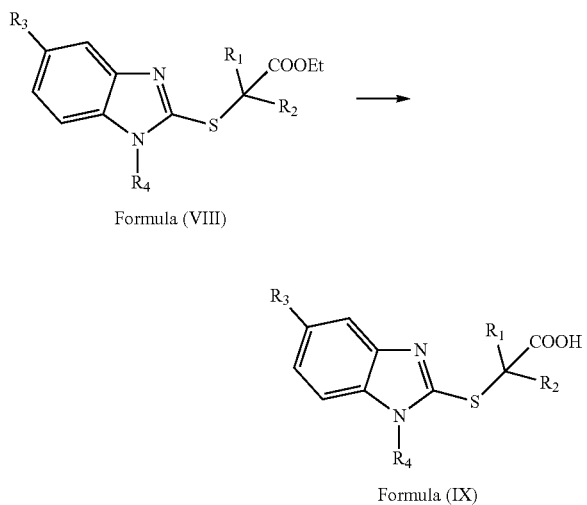

Formula (VIII) → Formula (IX)

(6) Reacting said compound of Formula (IX) with a base to form a compound of Formula (I), wherein M is a pharmaceutically acceptable cation; or reacting said compound of Formula (IX) with a chlorinating reagent, followed by an alcohol or amine to form a compound of Formula (I), wherein M is $C_{1-6}$ alkyl, amino or ester, Formula (I)

In one embodiment, said chlorinating reagent is selected from the group consisting of oxalyl chloride, thionyl chloride, phosphorus trichloride, phosphorus pentachloride and triphosgene.

In one embodiment, this invention provides a pharmaceutical composition comprising the benzimidazole derivatives of this invention.

In one embodiment, this invention provides a method for modulating uric acid levels and/or treating gout in a subject in need thereof, comprising the step of administering an effective amount of the pharmaceutical composition of this invention to said subject.

In one embodiment, this invention provides a method for modulating uric acid levels and/or treating gout in a subject in need thereof, comprising the step of administering an effective amount of the benzimidazole derivative of this invention to said subject.

In one embodiment, said subject suffers from hyperuricemia, gout, gouty arthritis, inflammatory arthritis, nephropathy, nephrolithiasis, joint inflammation, deposition of urate crystals within joints, urolithiasis, deposition of urate crystals in renal parenchyma, gout attack, tophaceous gout or any combinations thereof.

In one embodiment, this invention provides a method for modulating uric acid levels and/or treating gout in a subject in need thereof, comprising the step of administering to said subject the benzimidazole derivative of this invention in combination with a second drug.

In one embodiment, said second drug is selected from the group consisting of URAT1 inhibitor, xanthine oxidase inhibitor, xanthine dehydrogenase, xanthine oxidoreductase inhibitor, purine nucleoside phosphorylase inhibitor, uric acid transporter inhibitor, glucose transporter inhibitor, organic anion transporter (OAT) inhibitor, OAT-4 inhibitor and any combinations thereof.

The present invention will be further illustrated through specific examples below. These examples are mere illustrations of the present invention and do not limit the scope of protection.

Example 1. 2-methyl-2-[[5-methoxy-1-(4-cyanonaphth-1-yl)-1H-benzo[d]imidazol-2-yl]thio]propanoic acid (I1)

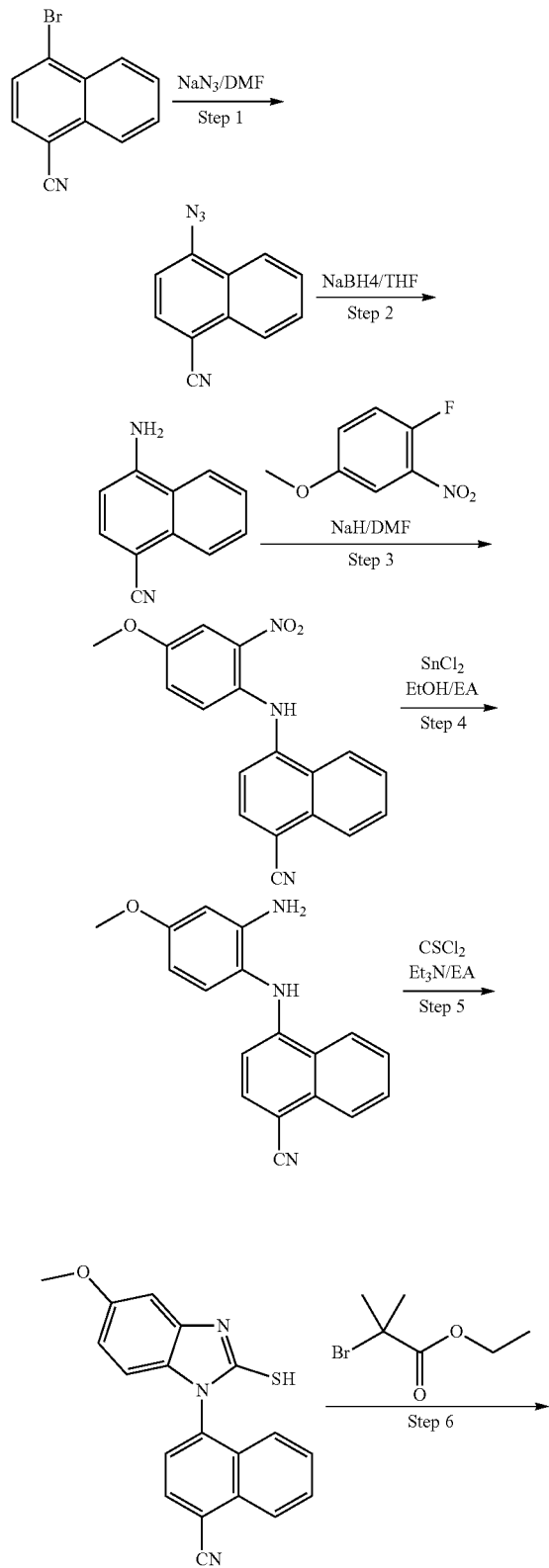

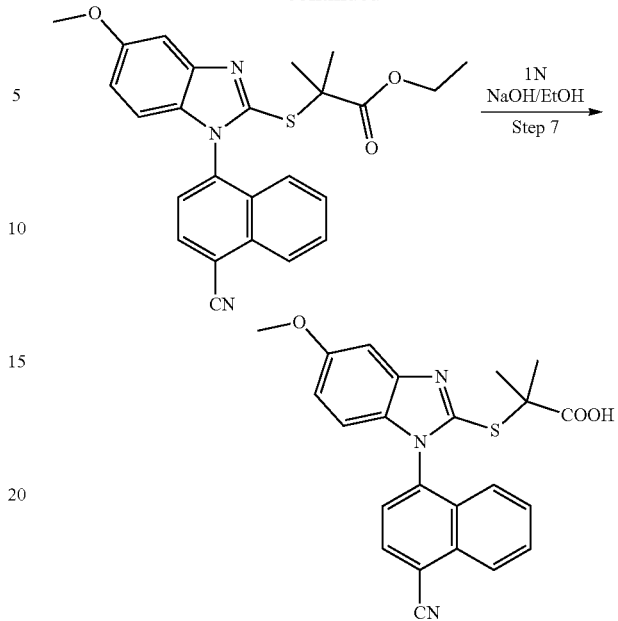

Step 1: 4-azido-1-naphthonitrile

4-Bromo-1-naphthonitrile (10 g, 43.1 mmol) was dissolved in 100 mL of DMSO. Then sodium azide (5 g, 76.9 mmol) was added, and the mixture was stirred at a temperature of 105° C. overnight. The resultant solution was extracted and separated by water (500 mL) and ethyl acetate (500 mL). The ethyl acetate phase was washed with water (500 mL×2) and saturated NaCl solution (500 mL×2), followed by concentration and column separation. 7 g of pale-yellow solid was obtained. The yield was 83%.

Step 2: 4-amino-1-naphthonitrile 4-azido-1-naphthonitrile (6 g, 30.9 mmol) was dissolved in 100 mL of tetrahydrofuran and cooled to 0° C. Sodium borohydride (2.34 g, 61.8 mmol) was added in portions, and allowed to warm to room temperature. The reaction mixture was stirred for 6 hours and quenched by addition of water. The resultant solution was extracted and separated by ethyl acetate (200 mL) and water (400 mL). The ethyl acetate phase was washed with saturated NaCl solution (200 mL×2), followed by concentration. 5 g of red solid was obtained and the yield was 96%.

Step 3: 4-[4-methoxy-2-nitrophenyl]amino]naphthonitrile 4-amino-1-naphthonitrile (4 g, 23.8 mmol) was dissolved in 120 mL DMF and was cooled to below 0° C. NaH (1.2 g, 30.5 mmol) was added. The reaction mixture was stirred at room temperature for 30 min, re-cooled to a temperature below 0° C., and then 4-methoxy-1-fluoro-2 nitrobenzene (3.3 g, 19.0 mmol) was added. The reaction mixture was stirred for 1.5 h at room temperature and quenched by the addition of saturated ammonium chloride solution (20 mL). Saturated NaCl solution (150 mL) was added to cause precipitation and 8.5 g of yellow solid was obtained after filtration. The solid was refined by stirring for 20 min in ethanol (50 mL) at 60° C., followed by filtration. 5.6 g of product was obtained after air-dried. The yield was 92%.

Step 4: 4-[4-methoxy-2-aminophenyl]amino]naphthonitrile

4-[(4-methoxy-2-nitrophenyl)amino]naphthonitrile (3.2 g, 10 mmol) was dissolved in tetrahydrofuran (100 mL) and stannous chloride dihydrate (9.0 g, 40 mmol) was added, followed by reacting for 1 hr at 70-75° C. After TLC (PE:EA=2:1) test showed full conversion of raw materials, saturated sodium carbonate solution was added to adjust the pH to 8-9. A large amount of insoluble substances appeared and was filtered. The filtrate was concentrated and mixed with ethyl acetate (100 mL). The organic phase was washed with water (100 mL×3), salt solution (50 mL×2), dried over anhydrous sodium sulfate, and concentrated. 1.7 g of light yellow powder was obtained and the yield was 60%.

Step 5: 4-(5-methoxy-2-mercapto-1H-benzo[d]imidazol-1-yl)naphthonitrile

4-[(4-methoxy-2-aminophenyl)amino]naphthonitrile (1.38 g, 4.78 mmol) was dissolved in ethyl acetate (30 mL) and triethylamine (1.45 g, 14.34 mmol) was added. Thiophosgene (1.1 g, 9.56 mmol) was added dropwise and reacted for 1 hour at room temperature. After TLC (PE:EA=2:1) test showed full conversion of raw materials, ethyl acetate (100 mL) was added to the system. The organic phase was washed with water (100 mL×3), salt solution (50 mL×2), dried over anhydrous sodium sulfate, and concentrated. 0.71 g of yellow powder was obtained and the yield was 45%.

Step 6: Ethyl 2-methyl-2-[5-methoxy-1-(4-cyanonaphth-1-yl)-1H-benzo[d]imidazol-2-yl]thio]propanoate 4-(5-Methoxy-2-thio-1H-benzo[d]imidazol-1-yl)naphthonitrile (0.66 g, 2.0 mmol) was dissolved in DMF (30 mL) and potassium carbonate (0.55 g, 4.0 mmol) was added. Ethyl 2-bromoisobutyrate (0.39 g, 2.0 mmol) was added and reacted for 2 hours at 45-50° C. After TLC (PE:EA=2:1) test showed full conversion of raw materials, ethyl acetate (100 mL) was added for extraction. The organic phase was washed with water (100 mL×3), saturated NaCl solution (50 mL*2), dried over anhydrous sodium sulfate, and concentrated. Residues were purified using silica gel column (eluent, petroleum ether:ethyl acetate=5:1, v:v). 0.48 g of white crystals was obtained and the yield was 54%.

Step 7: 2-methyl-2-[[5-methoxy-1-(4-cyanonaphth-1-yl)-1H-benzo[d]imidazol-2-yl]thio]propanoic Acid (I1)

Ethyl 2-methyl-2-[[5-methoxy-1-(4-cyanonaphth-1-yl)-1H-benzo[d]imidazol-2-yl]thio]propanoate (0.45 g (1.0 mmol) was dissolved in 5 mL of THF, and 5 mL of a 1N aqueous solution of sodium hydroxide was added, followed by stirring at room temperature for 2 hours. After TLC test showed full conversion of raw materials, 2N hydrochloric acid was added to adjust the pH to 4-5, and ethyl acetate was added for extraction, followed by concentration. The residues were separated and purified using silica gel column (eluent, petroleum ether:ethyl acetate=2:1, v:v). 355 mg of white solid was obtained. The yield was 85%. LC-MS: m/z 418.1 [M+H]$^+$.

$^1$H NMR (400 MHz, DMSO-d$_6$): δ=1.59 (s, 3H), 1.61 (s, 3H), 3.83 (s, 3H), 6.76-6.82 (m, 2H), 7.16 (d, J=8.4 Hz, 1H), 7.31 (d, J=2.0 Hz, 1H), 7.69-7.73 (m, 1H), 7.85-7.94 (m, 2H), 8.31 (d, J=8.0 Hz, 1H), 8.42 (d, J=7.6 Hz, 1H), 12.95 (s, 1H).

Example 2. 2-Methyl-2-[[1-(4-cyanonaphth-1-yl)-1H-benzo[d]imidazol-2-yl]thio]propanoic Acid (I2)

The compound (I2) was prepared according to the preparation method described in Example 1, except that o-fluoronitrobenzene was used in place of 4-methoxy-1-fluoro-2-nitrobenzene as a raw material. LC-MS: m/z 388.1 [M+H]$^+$.

$^1$H NMR (400 MHz, DMSO-d$_6$): δ=1.61 (s, 3H), 1.62 (s, 3H), 6.87 (d, J=8.4 Hz, 1H), 7.15-7.20 (m, 2H), 7.28-7.32 (m, 1H), 7.69-7.77 (m, 2H), 7.89-7.95 (m, 2H), 8.32 (d, J=8.4 Hz, 1H), 8.44 (d, J=7.6 Hz, 1H), 12.92 (s, 1H).

Example 3. 2-methyl-2-[[5-bromo-1-(4-cyanonaphth-1-yl)-1H-benzo[d]imidazol-2-yl]thio]propanoic Acid (I3)

The compound (I3) was prepared according to the preparation method described in Example 1, except that 4-bromo-1-fluoro-2-nitrobenzene was used in place of 4-methoxy-1-fluoro-2-nitrobenzene as a raw material. LC-MS: m/z 466.0 [M+H]$^+$.

$^1$H NMR (400 MHz, DMSO-d$_6$): δ=1.63 (s, 3H), 1.64 (s, 3H), 6.86 (d, J=8.8 Hz, 1H), 7.17 (d, J=8.4 Hz, 1H), 7.31 (dd, J=1.6 Hz, 8.4 Hz, 1H), 7.70-7.74 (m, 1H), 7.91-7.97 (m, 3H), 8.32 (d, J=8.0 Hz, 1H), 8.43 (d, J=7.6 Hz, 1H), 12.99 (s, 1H).

Example 4. 2-methyl-2-[[1-(4-benzonitrile)-1H-benzo[d]imidazol-2-yl]thio]propanoic Acid (I4)

The compound (I4) was prepared according to the preparation method described in Example 2, except that p-cyanoaniline was used as a raw material. LC-MS: m/z 338.1 [M+H]$^+$.

$^1$H NMR (400 MHz, DMSO-d$_6$): δ=1.62 (s, 6H), 7.21 (d, J=7.2 Hz, 1H), 7.24-7.32 (m, 2H), 7.70 (d, J=8.0 Hz, 1H), 7.76 (d, J=8.4 Hz, 2H), 8.12 (d, J=8.4 Hz, 2H), 12.86 (s, 1H)

Example 5. 2-methyl-2-[[1-(4-cyclopropylnaphth-1-yl)-1H-benzo[d]imidazol-2-yl]thio]propanoic Acid (I5)

The compound (I5) was prepared according to the preparation method described in Example 2, except that 1-bromo-4-cyclopropylnaphthalene was used in place of 4-bromo-1-naphthonitrile as a raw material. LC-MS: m/z 403.1 [M+H]$^+$.

$^1$H NMR (400 MHz, DMSO-d$_6$): δ=0.84-0.87 (m, 2H), 1.13-1.17 (m, 2H), 2.53-2.60 (m, 1H), 6.76 (d, J=8.4 Hz, 1H), 6.96 (d, J=8.4 Hz, 1H), 7.10-7.14 (m, 1H), 7.23-7.27 (m, 1H), 7.45 (d, J=7.6 Hz, 1H), 7.49-7.57 (m, 2H), 7.67-7.73 (m, 2H), 8.58 (d, J=8.4 Hz, 1H), 12.89 (s, 1H).

Example 6. 2-(4-Chlorophenyl)-2-[[1-(4-cyclopropylnaphth-1-yl)-1H-benzo[d]imidazol-2-yl]thio]acetic Acid (I6)

The compound (I6) was prepared according to the preparation method described in Example 5, except that ethyl 2-bromo-2-(4-chlorophenyl)acetate was used in place of ethyl 2-bromoisobutyrate as a raw material. LC-MS: m/z 485.1 [M+H]+.

¹H NMR (400 MHz, DMSO-d₆): δ=0.87-0.88 (m, 2H), 1.15-1.17 (m, 2H), 2.54-2.58 (m, 1H), 5.80 (s, 1H), 6.74-6.78 (m, 1H), 7.05-7.13 (m, 1H), 7.24-7.27 (m, 1H), 7.34-7.42 (m, 4H), 7.46-7.50 (m, 2H), 7.54-7.55 (m, 1H), 7.61-7.72 (m, 3H), 8.55-8.61 (m, 1H), 11.91 (s, 1H).

Example 7. 2-Methyl-2-[[1-(4-nitro-2-fluorophenyl)-1H-benzo[d]imidazol-2-yl]thio]propanoic Acid (I7)

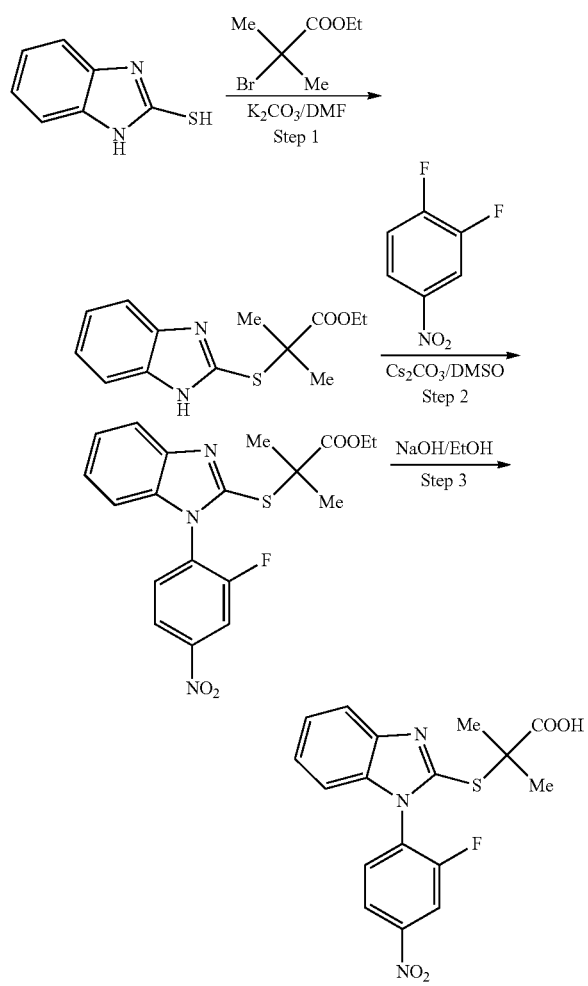

Step 1: Ethyl 2-methyl-2-[(1H-benzo[d]imidazol-2-yl)thio]propanoate 2-mercaptobenzimidazole (20 g, 133 mmol) was dissolved in 90 mL of DMF. Potassium carbonate (36.8 g, 266 mmol) and ethyl 2-bromoisobutyrate (25.97 g, 133 mmol) were added, and allowed to react at room temperature for 5 h. The reaction solution was filtered after addition of water. 23.8 g of white solid was obtained. The yield was 67%.

Step 2: Ethyl 2-methyl-2-[[1-(4-nitro-2-fluorophenyl)-1H-benzo[d]imidazol-2-yl]thio]propanoate Ethyl 2-methyl-2-[(1H-benzo[d]imidazol-2-yl)thio]propanoate (15.9 g, 60 mmol) was dissolved in 100 mL DMSO. 1,2-Difluoro-4-nitrobenzene (9.55 g, 60 mmol) and cesium carbonate (42.34 g, 120 mmol) was added, and the reaction was carried out at 60° C. under argon protection for 1 h. The reaction solution was extracted with water (400 mL) and ethyl acetate (400 mL) after cooling to room temperature. The organic layer was washed with water (400 mL×2) and saturated NaCl solution (200 mL×2), dried over anhydrous sodium sulfate, filtered, and concentrated. 23.2 g of yellow oil-like substance of was obtained. The yield was 96%.

Step 3: 2-Methyl-2-[[1-(4-nitro-2-fluorophenyl)-1H-benzo[d]imidazol-2-yl]thio]propanoic Acid (I7)

The compound was prepared according to the method described in Step 7 of Example 1, except that ethyl 2-methyl-2-[[5-methoxy-1-(4-cyanonaphth-1-yl)-1H-benzo[d]]imidazol-2-yl]thio]propanoate was replaced with ethyl 2-methyl-2-[[1-(4-nitro-2-fluorophenyl)-1H-benzo[d]imidazol-2-yl]thio]propanoate. The yield was 70%. LC-MS: m/z 376.1 [M+H]+.

¹H NMR (400 MHz, DMSO-d₆): δ=1.58 (s, 3H), 1.63 (s, 3H), 7.08 (d, J=8.0 Hz, 1H), 7.19-7.29 (m, 2H), 7.71 (d, J=7.6 Hz, 1H), 7.94-7.99 (m, 1H), 8.31 (d, J=8.4 Hz, 1H), 8.50 (d, J=2.4 Hz, 1H). 12.10 (s, 1H).

Example 8. 2-methyl-2-[(1-phenyl-1H-benzo[d]imidazol-2-yl)thio]propanoic Acid (I8)

The compound (I8) was prepared according to the preparation method described in Example 7, except that fluorobenzene was used in place of 1,2-difluoro-4-nitrobenzene as a raw material. LC-MS: m/z 313.1 [M+H]+.

¹H NMR (400 MHz, DMSO-d₆): δ=1.61 (s, 6H), 7.20 (d, J=7.2 Hz, 1H), 7.22-7.30 (m, 2H), 7.50-7.55 (m, 1H), 7.70 (d, J=8.0 Hz, 1H), 7.76-7.81 (m, 2H), 8.10 (d, J=8.4 Hz, 2H), 12.70 (s, 1H).

Example 9. 2-methyl-2-[(1-methyl-1H-benzo[d]imidazol-2-yl)thio]propanoic Acid (I9)

The compound (I9) was prepared according to the preparation method described in Example 7, except that iodomethane was used as a raw material in place of 1,2-difluoro-4-nitrobenzene. LC-MS: m/z 251.1 [M+H]+.

¹H NMR (400 MHz, DMSO-d₆): δ=1.61 (s, 6H), 3.79 (s, 3H), 7.22-7.32 (m, 2H), 7.57 (d, J=8.0 Hz, 1H), 7.64 (d, J=8.0 Hz, 1H), 12.91 (s, 1H).

Example 10. 2-Methyl-2-[[1-(4-acetamino-2-fluorophenyl)-1H-benzo[d]imidazol-2-yl]thio]propanoic Acid (I10)

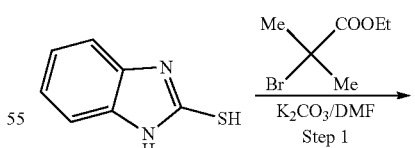

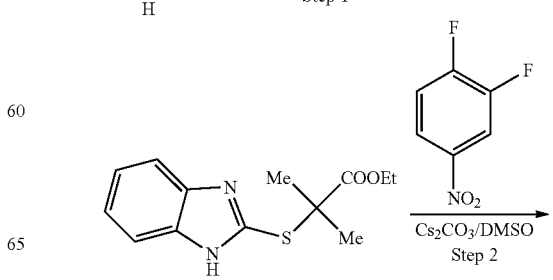

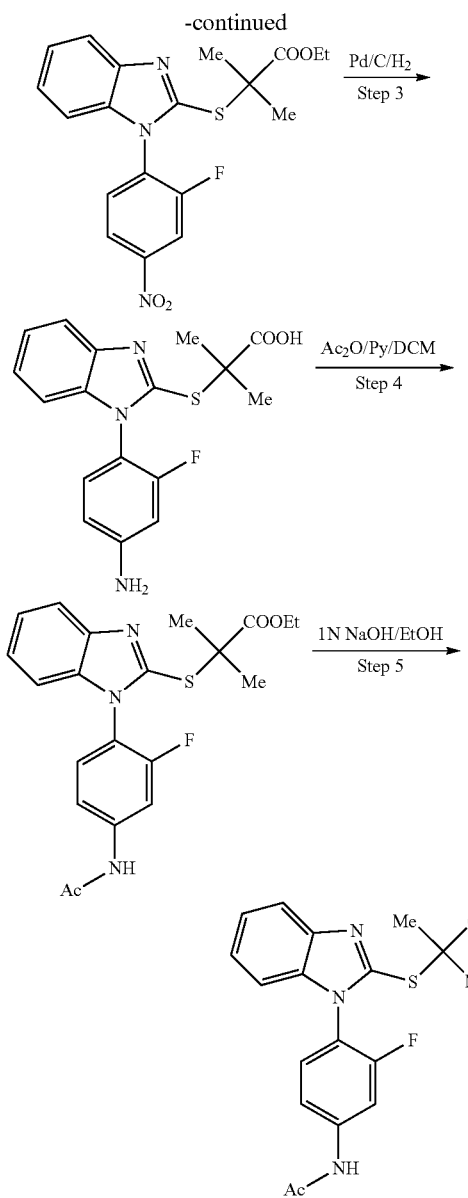

Steps 1 and 2 are the same as steps 1 and 2 of Example 7.

Step 3: Ethyl 2-methyl-2-[[1-(4-amino-2-fluorophenyl)-1H-benzo[d]imidazol-2-yl]thio]propanoate Ethyl 2-methyl-2-[[1-(4-nitro-2-fluorophenyl)-1H-benzo[d]imidazol-2-yl]thio]propanoate (10 g, 24.74 mmol) was dissolved in 100 mL of ethanol, and 1 g of palladium-carbon catalyst was added. The reaction was lasted for 10 hours at 50° C. The reaction solution was cooled to room temperature, filtered, and concentrated. 9.2 g of yellow oil-like substance was obtained. The yield was 98%.

Step 4: Ethyl 2-methyl-2-[[1-(4-acetamino-2-fluorophenyl)-1H-benzo[d]imidazol-2-yl]thio]propanoate Ethyl 2-methyl-2-[[1-(4-amino-2-fluorophenyl)-1H-benzo[d]imidazol-2-yl]thio]propanoate (2.14 g, 5.73 mmol) was dissolved in 20 mL DMF. Acetic anhydride (0.7 g, 6.88 mmol) and pyridine (1.36 g, 17.19 mmol) were added, and the reaction was lasted for 5 hours at 70° C. The reaction solution was extracted and separated with water (80 mL) and ethyl acetate (80 mL) after cooling to room temperature. and subsequently washed by water (40 mL×2) and saturated NaCl solution (40 mL×2). The organic layer was dried over anhydrous sodium sulfate, filtered, and concentrated. 2.3 g of yellow oil-like substance was obtained. The yield was 96%.

Step 5: 2-methyl-2-[[1-(4-acetamino-2-fluorophenyl)-1H-benzo[d]imidazol-2-yl]thio]propanoic Acid (I10)

The compound was prepared according to the method as described in Step 7 of Example 1, except that ethyl 2-methyl-2-[[5-methoxy-1-(4-cyanonaphth-1-yl)-1H-benzo[d]imidazol-2-yl]thio]propanoate was replaced with 2-methyl-2-[[1-(4-acetamido-2-fluorophenyl)-1H-benzo[d]imidazol-2-yl]thio]propanoate. The yield was 73%. LC-MS: m/z 388.1 [M+H]$^+$.

$^1$H NMR (400 MHz, DMSO-d$_6$): δ=1.60 (s, 3H), 1.63 (s, 3H), 7.07 (d, J=7.6 Hz, 1H), 7.21-7.29 (m, 2H), 7.47-7.54 (m, 2H), 7.67 (d, J=7.2 Hz, 1H), 7.89 (d, J=13.6 Hz, 1H), 10.44 (s, 1H), 12.90 (s, 1H).

Example 11. 2-methyl-2-[[1-(4-bromo-2-fluorophenyl)-1H-benzo[d]imidazol-2-yl]thio]propanoic Acid (I11)

Steps 1 to 3 are the same as steps 1 to 3 of Example 10.

Step 4: Ethyl 2-methyl-2-[[1-(4-bromo-2-fluorophenyl)-1H-benzo[d]imidazol-2-yl]thio]propanoate Ethyl 2-methyl-2-[[1-(4-amino-2-fluorophenyl)-1H-benzo[d]imidazol-2-yl]thio]propanoate (0.85 g, 2.28 mmol) was dissolved in 2 mL of hydrobromic acid. An aqueous solution (2 mL) of NaNO$_2$ (0.31 g, 4.55 mmol) was added at 0° C. After stirring for 0.5 hour, e cuprous bromide (0.65, 4.55 mmol) was added, and the reaction was lasted overnight at room temperature. The reaction solution was extracted and separated by water and ethyl acetate and subsequently washed with water (20 mL×2) and saturated NaCl solution (20 mL×2). The organic layer was dried over anhydrous sodium sulfate, filtered, and concentrated. 0.8 g of yellow oil-like substance was obtained. The yield was 80%.

Step 5: 2-methyl-2-[[1-(4-bromo-2-fluorophenyl)-1H-benzo[d]imidazol-2-yl]thio]propanoic Acid (I11)

The compound was prepared according to the method described in Step 7 of Example 1, except that ethyl 2-methyl-2-[[5-methoxy-1-(4-cyanonaphth-1-yl)-1H-benzo[d]imidazol-2-yl]thio]propanoate was replaced with ethyl 2-methyl-2-[[1-(4-bromo-2-fluorophenyl)-1H-benzo[d]imidazol-2-yl]thio]propanoate. The yield was 66%. LC-MS: m/z 409.0 [M+H]$^+$.

$^1$H NMR (400 MHz, DMSO-d6): δ=1.59 (s, 3H), 1.62 (s, 3H), 7.12 (d, J=7.6 Hz, 1H), 7.23-7.31 (m, 2H), 7.58-7.63 (m, 1H), 7.70 (d, J=8.0 Hz, 2H), 7.97 (d, J=9.6 Hz, 1H), 12.88 (s, 1H).

Example 12. 2-methyl-2-[[1-(4-chloro-2-fluorophenyl)-1H-benzo[d]imidazol-2-yl]thio]propanoic Acid (I12)

In accordance with the preparation method described in Example 11, compound (I12) was prepared using cuprous chloride in place of cuprous bromide. LC-MS: m/z 365.0 [M+H]$^+$.

$^1$H NMR (400 MHz, DMSO-d6): δ=1.59 (s, 3H), 1.62 (s, 3H), 7.12 (d, J=7.2 Hz, 1H), 7.24-7.31 (m, 2H), 7.57 (d, J=8.8 Hz, 1H), 6.66-7.71 (m, 2H), 7.84-7.87 (m, 1H), 12.81 (s, 1H).

Example 13. 2-methyl-2-[[1-(2-fluorophenyl)-1H-benzo[d]imidazol-2-yl]thio]propanoic Acid (I13)

Steps 1 to 3 are the same as Steps 1 to 3 of Example 10.

Step 4: 2-Methyl-2-[[1-(2-fluorophenyl)-1H-benzo[d]imidazol-2-yl]thio]propanoic Acid (I13)

Ethyl 2-methyl-2-[[1-(4-amino-2-fluorophenyl)-1H-benzo[d]imidazol-2-yl]thio]propanoate (1 g, 2.68 mmol) was dissolved in 2 mL of 50% sulfuric acid, and an aqueous solution (2 mL) of NaNO$_2$ (0.36 g, 5.36 mmol) was added at a temperature of 0° C. After stirring for 0.5 h, an aqueous solution of sodium hypophosphite (0.47, 5.36 mmol) was added, and the mixture was allowed to react at room temperature overnight. The reaction solution was extracted and separated by water (20 mL) and ethyl acetate (20 mL), and subsequently washed with water (20 mL×2) and saturated NaCl solution (20 mL×2). The organic layer was dried over anhydrous sodium sulfate, filtered, and concentrated. 0.88 g of yellow oil-like substance was obtained. The yield was 92% yield. After separation and purification on a silica gel column (eluent, petroleum ether:ethyl acetate=1:1, v:v), 100 mg of purified product was obtained. LC-MS: m/z 331.1 [M+H]$^+$.
$^1$H NMR (400 MHz, DMSO-d$_6$): δ=1.60 (s, 3H), 1.63 (s, 3H), 7.06 (d, J=7.6 Hz, 1H), 7.23-7.30 (m, 2H), 7.45-7.49 (m, 1H), 7.55-7.66 (m, 2H), 7.79 (d, J=8.0 Hz, 2H), 12.92 (s, 1H).

Example 14. Sodium 2-methyl-2-[[5-methoxy-1-(4-cyanonaphth-1-yl)-1H-benzo[d]imidazol-2-yl]thio]propanoate (I14)

2-methyl-2-[[5-methoxy-1-(4-cyanonaphth-1-yl)-1H-benzo[d]imidazol-2-yl]thio]propanoic acid (100 mg, (0.240 mmol) was dissolved in 5 mL of methanol, and sodium hydroxide solution (1 M, 0.240 mL) was added. The mixture was stirred at room temperature for 30 min, and was concentrated under reduced pressure to dryness. 105 mg of white solid was obtained. The yield was 100%. LC-MS: m/z 418.1 [M+H]$^+$.

Example 15 to Example 26

In accordance with the preparation method described in Example 14, the compounds in the following table can be prepared.

| Example | Structure |
|---|---|
| 15 | 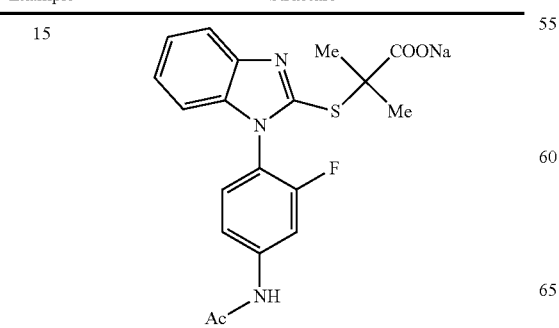 |
| 16 | 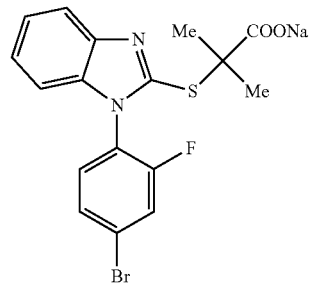 |
| 17 | 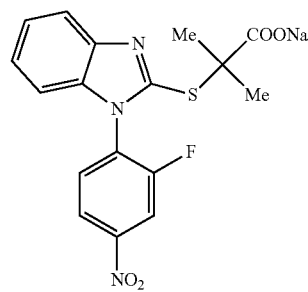 |
| 18 | 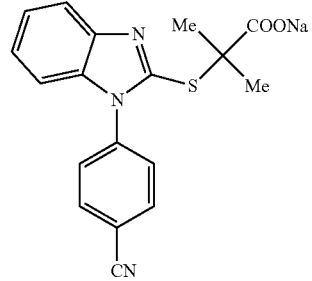 |
| 19 | 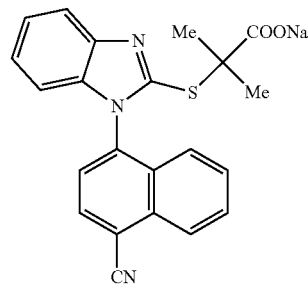 |
| 20 | 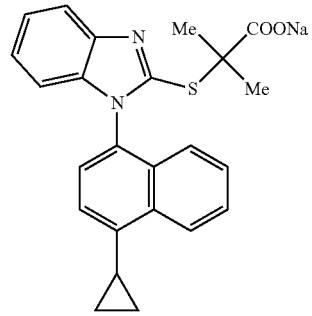 |

| Example | Structure |
|---|---|
| 21 | (1-methyl-benzimidazol-2-yl)thio-C(Me)₂-COONa |
| 22 | 1-(2-fluorophenyl)-benzimidazol-2-yl thio-C(Me)₂-COONa |
| 23 | 1-(2-fluoro-4-chlorophenyl)-benzimidazol-2-yl thio-C(Me)₂-COONa |
| 24 | 5-bromo-1-(4-cyanonaphth-1-yl)-benzimidazol-2-yl thio-C(Me)₂-COONa |
| 25 | 1-phenyl-benzimidazol-2-yl thio-C(Me)₂-COONa |
| 26 | 1-(4-cyclopropylnaphth-1-yl)-benzimidazol-2-yl thio-CH(4-chlorophenyl)-COONa |

Example 15. Sodium 2-methyl-2-[[1-(4-acetamino-2-fluorophenyl)-1H-benzo[d]imidazol-2-yl]thio]propanoate (I15)

The compound was prepared according to the preparation method described in Example 14, except that the raw material 2-methyl-2-[[5-methoxy-1-(4-cyanonaphth-1-yl)-1H-benzo[d]imidazol-2-yl]thio]propanoic acid was replaced with 2-methyl-2-[[1-(4-acetamino-2-fluorophenyl)-1H-benzo[d]imidazol-2-yl]thio]propanoic acid. The yield was 100% yield. LC-MS: m/z 388.1 [M+H]⁺.

Example 16. Sodium 2-methyl-2-[[1-(4-bromo-2-fluorophenyl)-1H-benzo[d]imidazol-2-yl]thio]propanoate (I16)

The compound was prepared according to the preparation method described in Example 14, except that the raw material 2-methyl-2-[[5-methoxy-1-(4-cyanonaphth-1-yl)-1H-benzo[d]imidazol-2-yl]thio]propanoic acid was replaced with 2-methyl-2-[[1-(4-bromo-2-fluorophenyl)-1H-benzo[d]imidazol-2-yl]thio]propanoic acid. The yield was 100%. LC-MS: m/z 409.0 [M+H]⁺.

Example 17. Sodium 2-methyl-2-[[1-(4-nitro-2-fluorophenyl)-1H-benzo[d]imidazol-2-yl]thio]propanoate (I17)

The compound was prepared according to the preparation method described in Example 14, except that the raw material 2-methyl-2-[[5-methoxy-1-(4-cyanonaphth-1-yl)-1H-benzo[d]imidazol-2-yl]thio]propanoic acid was replaced with 2-methyl-2-[[1-(4-nitro-2-fluorophenyl)-1H-benzo[d]imidazol-2-yl]thio]propanoic acid. The yield was 100% yield. LC-MS: m/z 376.1 [M+H]⁺.

Example 18. Sodium 2-methyl-2-[[1-(4-benzonitrile)-1H-benzo[d]imidazol-2-yl]thio]propanoate (I18)

The compound was prepared according to the preparation method described in Example 14, except that the raw material 2-methyl-2-[[5-methoxy-1-(4-cyanonaphth-1-yl)-1H-benzo[d]imidazol-2-yl]thio]propanoic acid was replaced with 2-methyl-2-[[1-(4-benzonitrileyl)-1H-benzo[d]imidazol-2-yl]thio]propanoic acid. The yield was 100% yield. LC-MS: m/z 338.1 [M+H]$^+$.

Example 19. Sodium 2-methyl-2-[[1-(4-cyanonaphth-1-yl)-1H-benzo[d]imidazol-2-yl]thio]propanoate (I19)

The compound was prepared according to the preparation method described in Example 14, except that the raw material 2-methyl-2-[[5-methoxy-1-(4-cyanonaphth-1-yl)-1H-benzo[d]imidazol-2-yl]thio]propanoic acid was replaced with 2-methyl-2-[[1-(4-cyanonaphth-1-yl)-1H-benzo[d]imidazol-2-yl]thio]propanoic acid. The yield was 100%. LC-MS: m/z 388.1 [M+H]$^+$.

Example 20. Sodium 2-methyl-2-[[1-(4-cyclopropylnaphth-1-yl)-1H-benzo[d]imidazol-2-yl]thio]propanoate (I20)

The compound was prepared according to the preparation method described in Example 14, except that the raw material 2-methyl-2-[[5-methoxy-1-(4-cyanonaphth-1-yl)-1H-benzo[d]imidazol-2-yl]thio]propanoic acid was replaced with 2-methyl-2-[[1-(4-cyclopropylnaphth-1-yl)-1H-benzo[d]imidazol-2-yl]thio]propanoic acid The yield was 100%. LC-MS: m/z 403.1 [M+H]$^+$.

Example 21. Sodium 2-methyl-2-[(1-methyl-1H-benzo[d]imidazol-2-yl)thio]propanoate (I21)

The compound was prepared according to the preparation method described in Example 14, except that the raw material 2-methyl-2-[[5-methoxy-1-(4-cyanonaphth-1-yl)-1H-benzo[d]imidazol-2-yl]thio]propanoic acid was replaced with using 2-methyl-2-[(1-methyl-1H-benzo[d]imidazol-2-yl)thio]propanoic acid. The yield was 100%. LC-MS: m/z 251.1 [M+H]$^+$.

Example 22. Sodium 2-methyl-2-[[1-(2-fluorophenyl)-1H-benzo[d]imidazol-2-yl]thio]propanoate (I22)

The compound was prepared according to the preparation method described in Example 14, except that the raw material 2-methyl-2-[[5-methoxy-1-(4-cyanonaphth-1-yl)-1H-benzo[d]imidazol-2-yl]thio]propanoic acid was replaced with 2-methyl-2-[[1-(2-fluorophenyl)-1H-benzo[d]imidazol-2-yl]thio]propanoic acid. The yield was 100%. LC-MS: m/z 331.1 [M+H]$^+$.

Example 23. Sodium 2-methyl-2-[[1-(4-chloro-2-fluorophenyl)-1H-benzo[d]imidazol-2-yl]thio]propanoate (I23)

The compound was prepared according to the preparation method described in Example 14, except that the raw material 2-methyl-2-[[5-methoxy-1-(4-cyanonaphth-1-yl)-1H-benzo[d]imidazol-2-yl]thio]propanoic acid was replaced with 2-methyl-2-[[1-(4-chloro-2-fluorophenyl)-1H-benzo[d]imidazol-2-yl]thio]propanoic acid. The yield was 100%. LC-MS: m/z 365.0 [M+H]$^+$.

Example 24. Sodium 2-methyl-2-[[5-bromo-1-(4-cyanonaphth-1-yl)-1H-benzo[d]imidazol-2-yl]thio]propanoate (I24)

The compound was prepared according to the preparation method described in Example 14, except that the raw material 2-methyl-2-[[5-methoxy-1-(4-cyanonaphth-1-yl)-1H-benzo[d]imidazol-2-yl]thio]propanoic acid was replaced with 2-methyl-2-[[1-(4-chloro-2-fluorophenyl)-1H-benzo[d]imidazol-2-yl]thio]propanoic acid. The yield was 100%. LC-MS: m/z 466.0 [M+H]$^+$.

Example 25. Sodium 2-methyl-2-[(1-phenyl-1H-benzo[d]imidazol-2-yl)thio]propanoate (I25)

The compound was prepared according to the preparation method described in Example 14, except that the raw material 2-methyl-2-[[5-methoxy-1-(4-cyanonaphth-1-yl)-1H-benzo[d]imidazol-2-yl]thio]propanoic acid was replaced with 2-methyl-2-[(1-phenyl-1H-benzo[d]imidazol-2-yl)thio]propanoic acid. The yield was 100%. LC-MS: m/z 313.1 [M+H]$^+$.

Example 26. Sodium 2-(4-chlorophenyl)-2-[[1-(4-cyclopropylnaphth-1-yl)-1H-benzo[d]imidazol-2-yl]thio]acetate (I26)

The compound was prepared according to the preparation method described in Example 14, except that the raw material 2-methyl-2-[[5-methoxy-1-(4-cyanonaphth-1-yl)-1H-benzo[d]imidazol-2-yl]thio]propanoic acid was replaced with 2-(4-chlorophenyl)-2-[[1-(4-cyclopropylnaphth-1-yl)-1H-benzo[d]imidazol-2-yl]thio]acetic acid. The yield was 100%. LC-MS: m/z 485.1 [M+H]$^+$.

Example 27. Potassium 2-methyl-2-[[5-methoxy-1-(4-cyanonaphth-1-yl)-1H-benzo[d]imidazol-2-yl]thio]propanoate (I27)

2-methyl-2-[[5-methoxy-1-(4-cyanonaphth-1-yl)-1H-benzo[d]imidazol-2-yl]thio]propanoic acid (100 mg, 0.240 mmol) was dissolved in 5 mL of methanol. Potassium hydroxide solution (1 M, 0.240 mL) was added. The mixture was stirred at room temperature for 30 minutes, and concentrated under reduced pressure to dryness. 109 mg of white solid was obtained. The yield was 100%. LC-MS: m/z 418.1 [M+H]$^+$.

Example 28 to Example 39

In accordance with the preparation method described in Example 27, the following compounds can be prepared.

| Example | Structure |
| --- | --- |
| 28 | 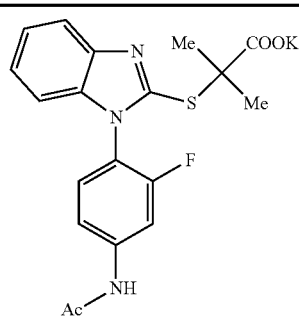 |

| Example | Structure |
|---------|-----------|
| 29 | 1-(4-bromo-2-fluorophenyl)-benzimidazole-2-yl-S-C(Me)₂-COOK |
| 30 | 1-(2-fluoro-4-nitrophenyl)-benzimidazole-2-yl-S-C(Me)₂-COOK |
| 31 | 1-(4-cyanophenyl)-benzimidazole-2-yl-S-C(Me)₂-COOK |
| 32 | 1-(4-cyanonaphthalen-1-yl)-benzimidazole-2-yl-S-C(Me)₂-COOK |
| 33 | 1-(4-cyclopropylnaphthalen-1-yl)-benzimidazole-2-yl-S-C(Me)₂-COOK |

| Example | Structure |
|---------|-----------|
| 34 | 1-methyl-benzimidazole-2-yl-S-C(Me)₂-COOK |
| 35 | 1-(2-fluorophenyl)-benzimidazole-2-yl-S-C(Me)₂-COOK |
| 36 | 1-(4-chloro-2-fluorophenyl)-benzimidazole-2-yl-S-C(Me)₂-COOK |
| 37 | 5-bromo-1-(4-cyanonaphthalen-1-yl)-benzimidazole-2-yl-S-C(Me)₂-COOK |
| 38 | 1-phenyl-benzimidazole-2-yl-S-C(Me)₂-COOK |

-continued

| Example | Structure |
|---|---|
| 39 | (structure: benzimidazole with S-CH(COOK) linked to 4-chlorophenyl, N-substituted with 4-cyclopropylnaphthalen-1-yl) |

Example 28. Potassium 2-methyl-2-[[1-(4-acetamino-2-fluorophenyl)-1H-benzo[d]imidazol-2-yl]thio]propanoate (I28)

The compound was prepared according to the preparation method described in Example 27, except that the raw material 2-methyl-2-[[5-methoxy-1-(4-cyanonaphth-1-yl)-1H-benzo[d]imidazol-2-yl]thio]propanoic acid was replaced with 2-methyl-2-[[1-(4-acetamino-2-fluorophenyl)-1H-benzo[d]imidazol-2-yl]thio]propanoic acid. The yield was 100%. LC-MS: m/z 388.1 $[M+H]^+$.

Example 29. Potassium 2-methyl-2-[[1-(4-bromo-2-fluorophenyl)-1H-benzo[d]imidazol-2-yl]thio]propanoate (I29)

The compound was prepared according to the preparation method described in Example 27, except that the raw material 2-methyl-2-[[5-methoxy-1-(4-cyanonaphth-1-yl)-1H-benzo[d]imidazol-2-yl]thio]propanoic acid was replaced with 2-methyl-2-[[1-(4-bromo-2-fluorophenyl)-1H-benzo[d]imidazol-2-yl]thio]propanoic acid. The yield was 100%. LC-MS: m/z 409.0 $[M+H]^+$.

Example 30. Potassium 2-methyl-2-[[1-(4-nitro-2-fluorophenyl)-1H-benzo[d]imidazol-2-yl]thio]propanoate (I30)

The compound was prepared according to the preparation method described in Example 27, except that the raw material 2-methyl-2-[[5-methoxy-1-(4-cyanonaphth-1-yl)-1H-benzo[d]imidazol-2-yl]thio]propanoic acid was replaced with 2-methyl-2-[[1-(4-nitro-2-fluorophenyl)-1H-benzo[d]imidazol-2-yl]thio]propanoic acid. The yield was 100%. LC-MS: m/z 376.1 $[M+H]^+$.

Example 31. Potassium 2-methyl-2-[[1-(4-benzonitrile)-1H-benzo[d]imidazol-2-yl]thio]propanoate (I31)

The compound was prepared according to the preparation method described in Example 27, except that the raw material 2-methyl-2-[[5-methoxy-1-(4-cyanonaphth-1-yl)-1H-benzo[d]imidazol-2-yl]thio]propanoic acid was replaced with 2-methyl-2-[[1-(4-cyanophenyl)-1H-benzo[d]imidazol-2-yl]thio]propanoic acid. The yield was 100%. LC-MS: m/z 338.1 $[M+H]^+$.

Example 32. Potassium 2-methyl-2-[[1-(4-cyanonaphth-1-yl)-1H-benzo[d]imidazol-2-yl]thio]propanoate (I32)

The compound was prepared according to the preparation method described in Example 27, except that the raw material 2-methyl-2-[[5-methoxy-1-(4-cyanonaphth-1-yl)-1H-benzo[d]imidazol-2-yl]thio]propanoic acid was replaced with 2-methyl-2-[[1-(4-cyanonaphth-1-yl)-1H-benzo[d]imidazol-2-yl]thio]propanoic acid. The yield was 100%. LC-MS: m/z 388.1 $[M+H]^+$.

Example 33. Potassium 2-methyl-2-[[1-(4-cyclopropylnaphth-1-yl)-1H-benzo[d]imidazol-2-yl]thio]propanoate (I33)

The compound was prepared according to the preparation method described in Example 27, except that the raw material 2-methyl-2-[[5-methoxy-1-(4-cyanonaphth-1-yl)-1H-benzo[d]imidazol-2-yl]thio]propanoic acid was replaced with 2-methyl-2-[[1-(4-cyclopropylnaphth-1-yl)-1H-benzo[d]imidazol-2-yl]thio]propanoic acid. The yield was 100%. LC-MS: m/z 403.1 $[M+H]^+$.

Example 34. Potassium 2-methyl-2-[(1-methyl-1H-benzo[d]imidazol-2-yl)thio]propanoate (I34)

The compound was prepared according to the preparation method described in Example 27, except that the raw material 2-methyl-2-[[5-methoxy-1-(4-cyanonaphth-1-yl)-1H-benzo[d]imidazol-2-yl]thio]propanoic acid was replaced with 2-methyl-2-[(1-methyl-1H-benzo[d]imidazol-2-yl)thio]propanoic acid. The yield was 100%. LC-MS: m/z 251.1 $[M+H]^+$.

Example 35. Potassium 2-methyl-2-[[1-(2-fluorophenyl)-1H-benzo[d]imidazol-2-yl]thio]propanoate (I35)

The compound was prepared according to the preparation method described in Example 27, except that the raw material 2-methyl-2-[[5-methoxy-1-(4-cyanonaphth-1-yl)-1H-benzo[d]imidazol-2-yl]thio]propanoic acid was replaced with 2-methyl-2-[[1-(2-fluorophenyl)-1H-benzo[d]imidazol-2-yl]thio]propanoic acid. The yield was 100%. LC-MS: m/z 331.1 $[M+H]^+$.

Example 36. Potassium 2-methyl-2-[[1-(4-chloro-2-fluorophenyl)-1H-benzo[d]imidazol-2-yl]thio]propanoate (I36)

The compound was prepared according to the preparation method described in Example 27, except that the raw material 2-methyl-2-[[5-methoxy-1-(4-cyanonaphth-1-yl)-1H-benzo[d]imidazol-2-yl]thio]propanoic acid was replaced with 2-methyl-2-[[1-(4-chloro-2-fluorophenyl)-1H-benzo[d]imidazol-2-yl]thio]propanoic acid. The yield was 100%. LC-MS: m/z 365.0 $[M+H]^+$.

Example 37. Potassium 2-methyl-2-[[5-bromo-1-(4-cyanonaphth-1-yl)-1H-benzo[d]imidazol-2-yl]thio]propanoate (I37)

The compound was prepared according to the preparation method described in Example 27, except that the raw material 2-methyl-2-[[5-methoxy-1-(4-cyanonaphth-1-yl)-1H-benzo[d]imidazol-2-yl]thio]propanoic acid was replaced with 2-methyl-2-[[1-(4-chloro-2-fluorophenyl)-1H-benzo[d]imidazol-2-yl]thio]propanoic acid. The yield was 100%. LC-MS: m/z 466.0 [M+H]$^+$.

Example 38. Potassium 2-methyl-2-[(1-phenyl-1H-benzo[d]imidazol-2-yl)thio]propanoate (I38)

The compound was prepared according to the preparation method described in Example 27, except that the raw material 2-methyl-2-[[5-methoxy-1-(4-cyanonaphth-1-yl)-1H-benzo[d]imidazol-2-yl]thio]propanoic acid was replaced with 2-methyl-2-[(1-phenyl-1H-benzo[d]imidazol-2-yl)thio]propanoic acid. The yield was 100%. LC-MS: m/z 313.1 [M+H]$^+$.

Example 39. Potassium 2-(4-chlorophenyl)-2-[[1-(4-cyclopropylnaphth-1-yl)-1H-benzo[d]imidazol-2-yl]thio]acetate (I39)

The compound was prepared according to the preparation method described in Example 27, except that the raw material 2-methyl-2-[[5-methoxy-1-(4-cyanonaphth-1-yl)-1H-benzo[d]imidazol-2-yl]thio]propanoic acid was replaced with 2-(4-chlorophenyl)-2-[[1-(4-cyclopropylnaphth-1-yl)-1H-benzo[d]imidazol-2-yl]thio]acetic acid. The yield was 100%. LC-MS: m/z 485.1 [M+H]$^+$.

Example 40. 2-methyl-2-[[5-methoxy-1-(4-cyanonaphth-1-yl)-1H-benzo[d]imidazol-2-yl]thio]propanoic acid ester (I40)

2-Methyl-2-[[5-methoxy-1-(4-cyanonaphth-1-yl)-1H-benzo[d]imidazol-2-yl]thio]propanoic acid (200 mg, 0.479 mmol) was dissolved in 10 mL of dry methylene chloride, and oxalyl chloride (122 mg, 0.960 mmol) was added. The reaction was catalyzed by 1 drop of DMF, and stirred at room temperature for 1 h. When TLC test showed no remaining raw material, the reaction solution was concentrated under reduced pressure to dryness. Anhydrous methanol 5 mL was added, and the mixture was stirred at room temperature for 30 minutes and concentrated under reduced pressure to dryness. 207 mg of white solid of was obtained. The yield was 100%. LC-MS: m/z 432.1 [M+H]$^+$.

$^1$H NMR (400 MHz, DMSO-d6): δ=1.60 (s, 3H), 1.62 (s, 3H), 3.66 (s, 3H), 3.84 (s, 3H), 6.75-6.82 (m, 2H), 7.17 (d, J=8.0 Hz, 1H), 7.30 (d, J=2.0 Hz, 1H), 7.68-7.72 (m, 1H), 7.86-7.94 (m, 2H), 8.31 (d, J=8.4 Hz, 1H), 8.44 (d, J=7.6 Hz, 1H).

Example 41-Example 52

In accordance with the preparation method described in Example 40, the following compounds can be prepared.

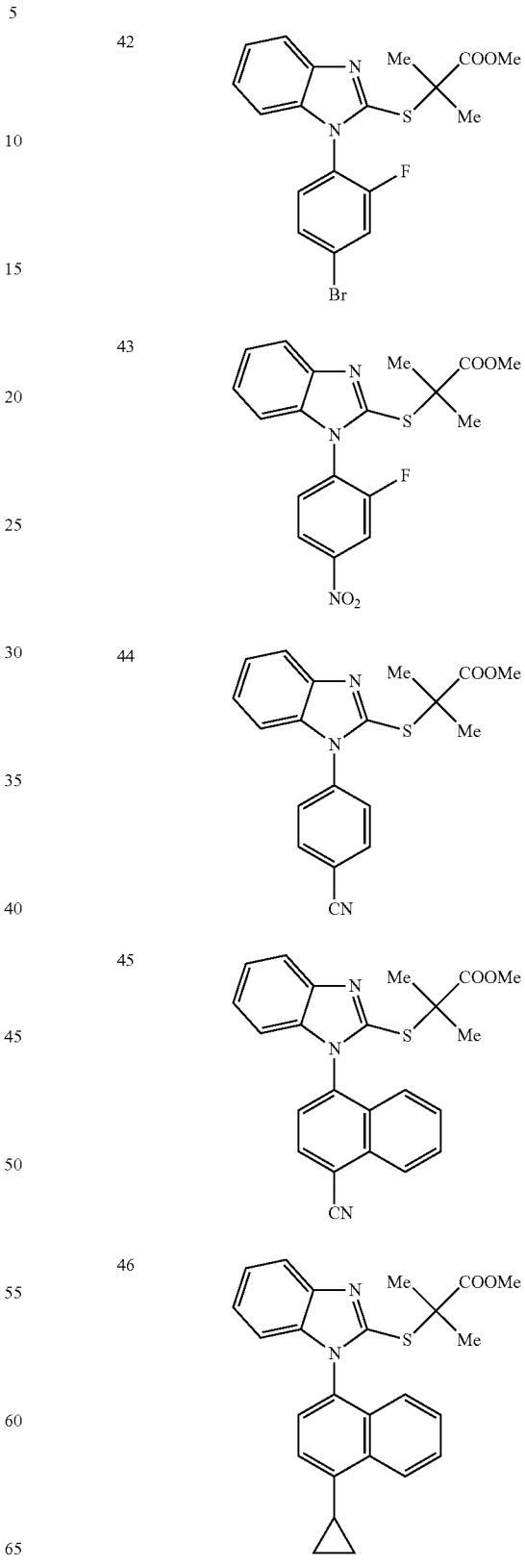

| Example | Structure |
|---------|-----------|
| 47 | 2-(methylthio)-1-methyl-1H-benzimidazole with -S-C(Me)(Me)-COOMe |
| 48 | 1-(2-fluorophenyl)-1H-benzimidazol-2-yl with -S-C(Me)(Me)-COOMe |
| 49 | 1-(2-fluoro-4-chlorophenyl)-1H-benzimidazol-2-yl with -S-C(Me)(Me)-COOMe |
| 50 | 5-bromo-1-(4-cyanonaphth-1-yl)-1H-benzimidazol-2-yl with -S-C(Me)(Me)-COOMe |
| 51 | 1-phenyl-1H-benzimidazol-2-yl with -S-C(Me)(Me)-COOMe |
| 52 | 1-(4-cyclopropylnaphth-1-yl)-1H-benzimidazol-2-yl with -S-CH(4-chlorophenyl)-COOMe |

Example 41. Methyl 2-methyl-2-[[1-(4-acetamino-2-fluorophenyl)-1H-benzo[d]imidazol-2-yl]thio]propanoate (I41)

The compound was prepared according to the preparation method described in Example 40, except that the starting material 2-methyl-2-[[5-methoxy-1-(4-cyanonaphth-1-yl)-1H-benzo[d]imidazol-2-yl]thio]propanoic acid was replaced with 2-methyl-2-[[1-(4-acetamino-2-fluorophenyl)-1H-benzo[d]imidazol-2-yl]thio]propanoic acid. The yield was 100%. LC-MS: m/z 402.1 [M+H]$^+$.

Example 42. Methyl 2-methyl-2-[[1-(4-bromo-2-fluorophenyl)-1H-benzo[d]imidazol-2-yl]thio]propanoate (I42)

The compound was prepared according to the preparation method described in Example 40, except that the starting material 2-methyl-2-[[5-methoxy-1-(4-cyanonaphth-1-yl)-1H-benzo[d]imidazol-2-yl]thio]propanoic acid was replaced with 2-methyl-2-[[1-(4-bromo-2-fluorophenyl)-1H-benzo[d]imidazol-2-yl]thio]propanoic acid. The yield was 100%. LC-MS: m/z 423.0 [M+H]$^+$.

Example 43. Methyl 2-methyl-2-[[1-(4-nitro-2-fluorophenyl)-1H-benzo[d]imidazol-2-yl]thio]propanoate (I43)

The compound was prepared according to the preparation method described in Example 40, except that the starting material 2-methyl-2-[[5-methoxy-1-(4-cyanonaphth-1-yl)-1H-benzo[d]imidazol-2-yl]thio]propanoic acid was replaced with 2-methyl-2-[[1-(4-nitro-2-fluorophenyl)-1H-benzo[d]imidazol-2-yl]thio]propanoic acid. The yield was 100%. LC-MS: m/z 390.1 [M+H]$^+$.

Example 44. Methyl 2-methyl-2-[[1-(4-benzonitrile)-1H-benzo[d]imidazol-2-yl]thio]propanoate (I44)

The compound was prepared according to the preparation method described in Example 40, except that the starting material 2-methyl-2-[[5-methoxy-1-(4-cyanonaphth-1-yl)-1H-benzo[d]imidazol-2-yl]thio]propanoic acid was replaced with 2-methyl-2-[[1-(4-benzonitrileyl)-1H-benzo[d]imidazol-2-yl]thio]propanoic acid. The yield was 100%. LC-MS: m/z 352.1 [M+H]$^+$.

Example 45. Methyl 2-methyl-2-[[1-(4-cyanonaphth-1-yl)-1H-benzo[d]imidazol-2-yl]thio]propanoate (I45)

The compound was prepared according to the preparation method described in Example 40, except that the starting material 2-methyl-2-[[5-methoxy-1-(4-cyanonaphth-1-yl)-1H-benzo[d]imidazol-2-yl]thio]propanoic acid was replaced with 2-methyl-2-[[1-(4-cyanonaphth-1-yl)-1H-benzo[d]imidazol-2-yl]thio]propanoic acid. The yield was 100%. LC-MS: m/z 402.1 [M+H]$^+$.

Example 46. Methyl 2-methyl-2-[[1-(4-cyclopropylnaphth-1-yl)-1H-benzo[d]imidazol-2-yl]thio]propanoate (I46)

The compound was prepared according to the preparation method described in Example 40, except that the starting material 2-methyl-2-[[5-methoxy-1-(4-cyanonaphth-1-yl)-1H-benzo[d]imidazol-2-yl]thio]propanoic acid was replaced with 2-methyl-2-[[1-(4-cyclopropylnaphth-1-yl)-1H-benzo[d]imidazol-2-yl]thio]propanoic acid. The yield was 100%. LC-MS: m/z 417.2 [M+H]$^+$.

Example 47. Methyl 2-methyl-2-[(1-methyl-1H-benzo[d]imidazol-2-yl)thio]propanoate (I47)

The compound was prepared according to the preparation method described in Example 40, except that the starting material 2-methyl-2-[[5-methoxy-1-(4-cyanonaphth-1-yl)-1H-benzo[d]imidazol-2-yl]thio]propanoic acid was replaced with 2-methyl-2-[(1-methyl-1H-benzo[d]imidazol-2-yl)thio]propanoic acid. The yield was 100%. LC-MS: m/z 265.1 [M+H]$^+$.

Example 48. Methyl 2-methyl-2-[[1-(2-fluorophenyl)-1H-benzo[d]imidazol-2-yl]thio]propanoate (I48)

The compound was prepared according to the preparation method described in Example 40, except that the starting material 2-methyl-2-[[5-methoxy-1-(4-cyanonaphth-1-yl)-1H-benzo[d]imidazol-2-yl]thio]propanoic acid was replaced with 2-methyl-2-[[1-(2-fluorophenyl)-1H-benzo[d]imidazol-2-yl]thio]propanoic acid. The yield was 100%. LC-MS: m/z 345.1 [M+H]$^+$.

Example 49. Methyl 2-methyl-2-[[1-(4-chloro-2-fluorophenyl)-1H-benzo[d]imidazol-2-yl]thio]propanoate (I49)

The compound was prepared according to the preparation method described in Example 40, except that the starting material 2-methyl-2-[[5-methoxy-1-(4-cyanonaphth-1-yl)-1H-benzo[d]imidazol-2-yl]thio]propanoic acid was replaced with 2-methyl-2-[[1-(4-chloro-2-fluorophenyl)-1H-benzo[d]imidazol-2-yl]thio]propanoic acid. The yield was 100%. LC-MS: m/z 379.1 [M+H]$^+$.

Example 50. Methyl 2-methyl-2-[[5-bromo-1-(4-cyanonaphth-1-yl)-1H-benzo[d]imidazol-2-yl]thio]propanoate (I50)

The compound was prepared according to the preparation method described in Example 40, except that the starting material 2-methyl-2-[[5-methoxy-1-(4-cyanonaphth-1-yl)-1H-benzo[d]imidazol-2-yl]thio]propanoic acid was replaced with 2-methyl-2-[[5-bromo-1-(4-cyanonaphth-1-yl)-1H-benzo[d]imidazol-2-yl]thio]propanoic acid. The yield was 100%. LC-MS: m/z 480.0 [M+H]$^+$.

Example 51. Methyl 2-methyl-2-[(1-phenyl-1H-benzo[d]imidazol-2-yl)thio]propanoate (I51)

The compound was prepared according to the preparation method described in Example 40, except that the starting material 2-methyl-2-[[5-methoxy-1-(4-cyanonaphth-1-yl)-1H-benzo[d]imidazol-2-yl]thio]propanoic acid was replaced with 2-methyl-2-[(1-phenyl-1H-benzo[d]imidazol-2-yl)thio]propanoic acid. The yield was 100%. LC-MS: m/z 327.1 [M+H]$^+$.

Example 52. Methyl 2-(4-chlorophenyl)-2-[[1-(4-cyclopropylnaphth-1-yl)-1H-benzo[d]imidazol-2-yl]thio]acetate (I52)

The compound was prepared according to the preparation method described in Example 40, except that the starting material 2-methyl-2-[[5-methoxy-1-(4-cyanonaphth-1-yl)-1H-benzo[d]imidazol-2-yl]thio]propanoic acid was replaced with 2-(4-chlorophenyl)-2-[[1-(4-cyclopropylnaphth-1-yl)-1H-benzo[d]imidazol-2-yl]thio]acetic acid. The yield was 100%. LC-MS: m/z 499.1 [M+H]$^+$.

Example 53. Ethyl 2-methyl-2-[[5-methoxy-1-(4-cyanonaphth-1-yl)-1H-benzo[d]imidazol-2-yl]thio]propanoate (I53)

2-Methyl-2-[[5-methoxy-1-(4-cyanonaphth-1-yl)-1H-benzo[d]imidazol-2-yl]thio]propanoic acid (200 mg, 0.479 mmol) was dissolved in 10 mL of dry dichloromethane, and oxalyl chloride (122 mg, 0.960 mmol) was added. The reaction was catalyzed by 1 drop of DMF and stirred at room temperature for 1 h. When TLC test showed no residual raw material, the reaction solution was concentrated under reduced pressure to dryness. After addition of 5 mL of absolute ethanol, the mixture was stirred at room temperature for 30 minutes, and concentrated under reduced pressure to dryness. 213 mg of white solid was obtained. The yield was 100%. LC-MS: m/z 446.1 [M+H]$^+$.

$^1$H NMR (400 MHz, DMSO-d6): δ=1.31 (t, J=8.0 Hz, 3H), 1.60 (s, 3H), 1.62 (s, 3H), 3.82 (s, 3H), 4.10-4.15 (m, 2H), 6.71-6.80 (m, 2H), 7.16 (d, J=8.0 Hz, 1H), 7.29 (d, J=2.4 Hz, 1H), 7.66-7.71 (m, 1H), 7.85-7.94 (m, 2H), 8.32 (d, J=8.0 Hz, 1H), 8.47 (d, J=7.2 Hz, 1H).

Example 54 to Example 65

In accordance with the preparation method described in Example 53, the following compounds can be prepared.

| Example | Structure |
| --- | --- |
| 54 | ![structure] |

| Example | Structure |
|---|---|
| 55 | benzimidazole-S-C(Me)₂-COOEt, N1-(2-fluoro-4-bromophenyl) |
| 56 | benzimidazole-S-C(Me)₂-COOEt, N1-(2-fluoro-4-nitrophenyl) |
| 57 | benzimidazole-S-C(Me)₂-COOEt, N1-(4-cyanophenyl) |
| 58 | benzimidazole-S-C(Me)₂-COOEt, N1-(4-cyanonaphth-1-yl) |
| 59 | benzimidazole-S-C(Me)₂-COOEt, N1-(4-cyclopropylnaphth-1-yl) |
| 60 | benzimidazole-S-C(Me)₂-COOEt, N1-methyl |
| 61 | benzimidazole-S-C(Me)₂-COOEt, N1-(2-fluorophenyl) |
| 62 | benzimidazole-S-C(Me)₂-COOEt, N1-(2-fluoro-4-chlorophenyl) |
| 63 | 5-bromo-benzimidazole-S-C(Me)₂-COOEt, N1-(4-cyanonaphth-1-yl) |
| 64 | benzimidazole-S-C(Me)₂-COOEt, N1-phenyl |

| Example | Structure |
|---|---|
| 65 | (structure: ethyl 2-((1-(4-cyclopropylnaphthalen-1-yl)-1H-benzo[d]imidazol-2-yl)thio)-2-(4-chlorophenyl)acetate) |

Example 54. Ethyl 2-methyl-2-[[1-(4-acetamino-2-fluorophenyl)-1H-benzo[d]imidazol-2-yl]thio]propanoate (I54)

The compound was prepared according to the preparation method described in Example 53, except that the starting material 2-methyl-2-[[5-methoxy-1-(4-cyanonaphth-1-yl)-1H-benzo[d]imidazol-2-yl]thio]propanoic acid was replaced with 2-methyl-2-[[1-(4-acetamino-2-fluorophenyl)-1H-benzo[d]imidazol-2-yl]thio]propanoic acid. The yield was 100%. LC-MS: m/z 416.1 [M+H]$^+$.

Example 55. Ethyl 2-methyl-2-[[1-(4-bromo-2-fluorophenyl)-1H-benzo[d]imidazol-2-yl]thio]propanoate (I55)

The compound was prepared according to the preparation method described in Example 53, except that the starting material 2-methyl-2-[[5-methoxy-1-(4-cyanonaphth-1-yl)-1H-benzo[d]imidazol-2-yl]thio]propanoic acid was replaced with 2-methyl-2-[[1-(4-bromo-2-fluorophenyl)-1H-benzo[d]imidazol-2-yl]thio]propanoic acid. The yield was 100%. LC-MS: m/z 437.0 [M+H]$^+$.

Example 56. Ethyl 2-methyl-2-[[1-(4-nitro-2-fluorophenyl)-1H-benzo[d]imidazol-2-yl]thio]propanoate (I56)

The compound was prepared according to the preparation method described in Example 53, except that the starting material 2-methyl-2-[[5-methoxy-1-(4-cyanonaphth-1-yl)-1H-benzo[d]imidazol-2-yl]thio]propanoic acid was replaced with 2-methyl-2-[[1-(4-nitro-2-fluorophenyl)-1H-benzo[d]imidazol-2-yl]thio]propanoic acid. The yield was 100%. LC-MS: m/z 404.1 [M+H]$^+$.

Example 57. Ethyl 2-methyl-2-[[1-(4-cyanophenyl)-1H-benzo[d]imidazol-2-yl]thio]propanoate (I57)

The compound was prepared according to the preparation method described in Example 53, except that the starting material 2-methyl-2-[[5-methoxy-1-(4-cyanonaphth-1-yl)-1H-benzo[d]imidazol-2-yl]thio]propanoic acid was replaced with 2-methyl-2-[[1-(4-cyanophenyl)-1H-benzo[d]imidazol-2-yl]thio]propanoic acid. The yield was 100%. LC-MS: m/z 366.1 [M+H]$^+$.

Example 58. Ethyl 2-methyl-2-[[1-(4-cyanonaphth-1-yl)-1H-benzo[d]imidazol-2-yl]thio]propanoate (I58)

The compound was prepared according to the preparation method described in Example 53, except that the starting material 2-methyl-2-[[5-methoxy-1-(4-cyanonaphth-1-yl)-1H-benzo[d]imidazol-2-yl]thio]propanoic acid was replaced with 2-methyl-2-[[1-(4-cyanonaphth-1-yl)-1H-benzo[d]imidazol-2-yl]thio]propanoic acid. The yield was. LC-MS: m/z 416.1 [M+H]$^+$.

Example 59. Ethyl-2-methyl-2-[[1-(4-cyclopropylnaphth-1-yl)-1H-benzo[d]imidazol-2-yl]thio]propanoate (I59)

The compound was prepared according to the preparation method described in Example 53, except that the starting material 2-methyl-2-[[5-methoxy-1-(4-cyanonaphth-1-yl)-1H-benzo[d]imidazol-2-yl]thio]propanoic acid was replaced with 2-methyl-2-[[1-(4-cyclopropylnaphth-1-yl)-1H-benzo[d]imidazol-2-yl]thio]propanoic acid. The yield was 100%. LC-MS: m/z 431.2 [M+H]$^+$.

Example 60. Ethyl 2-methyl-2-[(1-methyl-1H-benzo[d]imidazol-2-yl)thio]propanoate (I60)

The compound was prepared according to the preparation method described in Example 53, except that the starting material 2-methyl-2-[[5-methoxy-1-(4-cyanonaphth-1-yl)-1H-benzo[d]imidazol-2-yl]thio]propanoic acid was replaced with 2-methyl-2-[(1-methyl-1H-benzo[d]imidazol-2-yl)thio]propanoic acid. The yield was 100%. LC-MS: m/z 279.1 [M+H]$^+$.

Example 61. Ethyl 2-methyl-2-[[1-(2-fluorophenyl)-1H-benzo[d]imidazol-2-yl]thio]propanoate (I61)

The compound was prepared according to the preparation method described in Example 53, except that the starting material 2-methyl-2-[[5-methoxy-1-(4-cyanonaphth-1-yl)-1H-benzo[d]imidazol-2-yl]thio]propanoic acid was replaced with 2-methyl-2-[[1-(2-fluorophenyl)-1H-benzo[d]imidazol-2-yl]thio]propanoic acid. The yield was 100%. LC-MS: m/z 359.1 [M+H]$^+$.

Example 62. Ethyl 2-methyl-2-[[1-(4-chloro-2-fluorophenyl)-1H-benzo[d]imidazol-2-yl]thio]propanoate (I62)

The compound was prepared according to the preparation method described in Example 53, except that the starting material 2-methyl-2-[[5-methoxy-1-(4-cyanonaphth-1-yl)-1H-benzo[d]imidazol-2-yl]thio]propanoic acid was replaced with 2-methyl-2-[[1-(4-chloro-2-fluorophenyl)-1H-benzo[d]imidazol-2-yl]thio]propanoic acid. The yield was 100%. LC-MS: m/z 393.1 [M+H]$^+$.

Example 63. Ethyl 2-methyl-2-[[5-bromo-1-(4-cyanonaphth-1-yl)-1H-benzo[d]imidazol-2-yl]thio]propanoate (I63)

The compound was prepared according to the preparation method described in Example 53, except that the starting material 2-methyl-2-[[5-methoxy-1-(4-cyanonaphth-1-yl)-1H-benzo[d]imidazol-2-yl]thio]propanoic acid was replaced with 2-methyl-2-[[5-bromo-1-(4-cyanonaphth-1-yl)-1H-benzo[d]imidazol-2-yl]thio]propanoic acid. The yield was 100%. LC-MS: m/z 494.0 [M+H]$^+$.

Example 64. Ethyl 2-methyl-2-[(1-phenyl-1H-benzo[d]imidazol-2-yl)thio]propanoate (I64)

The compound was prepared according to the preparation method described in Example 53, except that the starting material 2-methyl-2-[[5-methoxy-1-(4-cyanonaphth-1-yl)-1H-benzo[d]imidazol-2-yl]thio]propanoic acid was replaced with 2-methyl-2-[(1-phenyl-1H-benzo[d]imidazol-2-yl)thio]propanoic acid. The yield was 100%. LC-MS: m/z 341.1 [M+H]$^+$.

Example 65. Ethyl 2-(4-chlorophenyl)-2-[[1-(4-cyclopropylnaphth-1-yl)-1H-benzo[d]imidazol-2-yl]thio]acetate (I65)

The compound was prepared according to the preparation method described in Example 53, except that the starting material 2-methyl-2-[[5-methoxy-1-(4-cyanonaphth-1-yl)-1H-benzo[d]imidazol-2-yl]thio]propanoic acid was replaced with 2-(4-chlorophenyl)-2-[[1-(4-cyclopropylnaphth-1-yl)-1H-benzo[d]imidazol-2-yl]thio]acetic acid. The yield was 100%. LC-MS: m/z 513.1 [M+H]$^+$.

Example 66. (5-methyl-2-oxo-1,3-dioxol-4-yl)methyl 2-methyl-2-[[5-methoxy-1-(4-cyanonaphth-1-yl)-1H-benzo[d]imidazol-2-yl]thio]propanoate (I66)

(5-methyl-2-oxo-1,3-dioxol-4-yl)methyl 2-methyl-2-[[5-methoxy-1-(4-cyanophenyl-1-yl)-1H-benzo[d]imidazol-2-yl]thio]propanoic acid (100 mg, 0.240 mmol) was dissolved in 5 mL of dry methylene chloride and oxalyl chloride (61 mg, 0.480 mmol) was added. The reaction was catalyzed by 1 drop of DMF, followed by stirring at room temperature for 1 h. When TLC test showed no residual raw material, the reaction solution was concentrated under reduced pressure to dryness. The residues were dissolved in 5 mL of dry dichloromethane. 4-(hydroxymethyl)-5-methyl-[1,3]-dioxolane-2-one (62 mg, 0.480 mmol) and triethylamine (71 mg, 0.702 mmol) were added. The reaction was lasted for 3 hours at 40° C. under nitrogen protection. The reaction system was concentrated under reduced pressure, and the residues were separated and purified on a silica gel column (eluent petroleum ether:ethyl acetate=10:1, v:v). 83 mg of white solid was obtained. The yield was 65%. LC-MS: m/z 530.1 [M+H]$^+$.

$^1$H NMR (400 MHz, DMSO-d6): δ=1.58 (s, 3H), 1.61 (s, 3H), 2.60 (s, 3H), 3.83 (s, 3H), 4.70 (s, 2H), 6.74-6.81 (m, 2H), 7.15 (d, J=7.6 Hz, 1H), 7.32 (d, J=2.0 Hz, 1H), 7.68-7.72 (m, 1H), 7.84-7.94 (m, 2H), 8.29 (d, J=8.0 Hz, 1H), 8.41 (d, J=8.4 Hz, 1H).

Example 67 to Example 78

In accordance with the preparation method described in Example 66, the following compounds can be prepared.

| Example | Structure |
|---|---|
| 67 | (structure) |
| 68 | (structure) |
| 69 | (structure) |
| 70 | (structure) |

| Example | Structure |
|---|---|
| 71 | 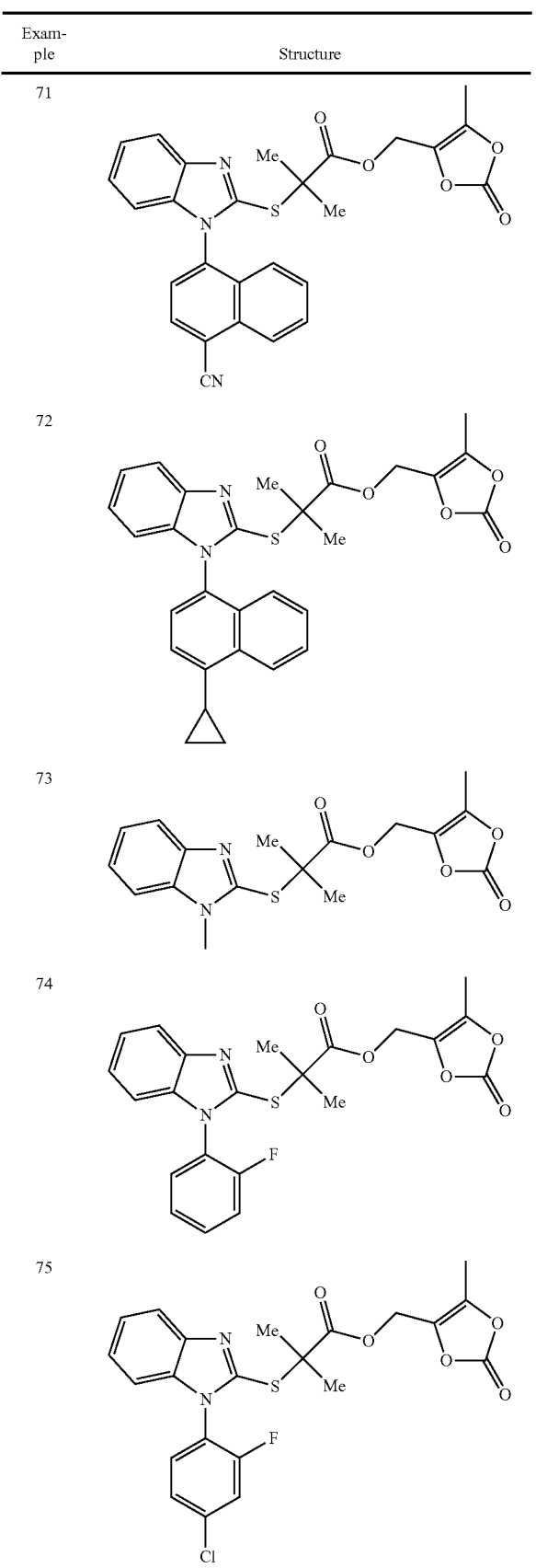 |
| 72 | 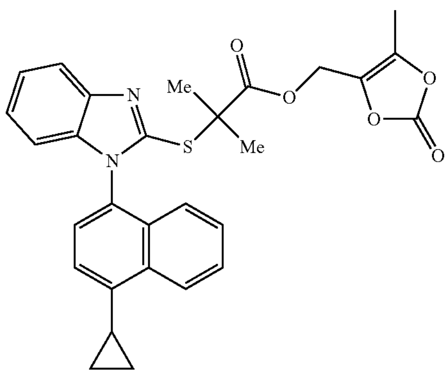 [SMILES: Cc1oc(=O)oc1COC(=O)C(C)(C)Sc1nc2ccccc2n1-c1ccc(C2CC2)c2ccccc12] |
| 73 | 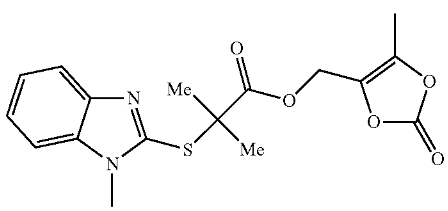 [SMILES: Cc1oc(=O)oc1COC(=O)C(C)(C)Sc1nc2ccccc2n1C] |
| 74 | 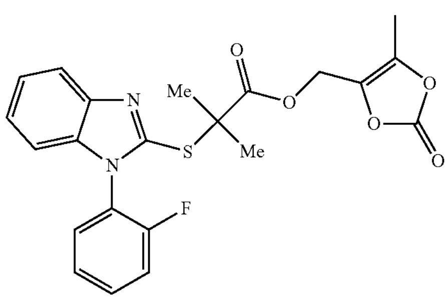 [SMILES: Cc1oc(=O)oc1COC(=O)C(C)(C)Sc1nc2ccccc2n1-c1ccccc1F] |
| 75 | 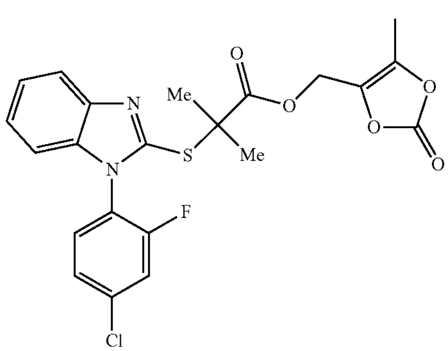 [SMILES: Cc1oc(=O)oc1COC(=O)C(C)(C)Sc1nc2ccccc2n1-c1ccc(Cl)cc1F] |

| Example | Structure |
|---|---|
| 76 | 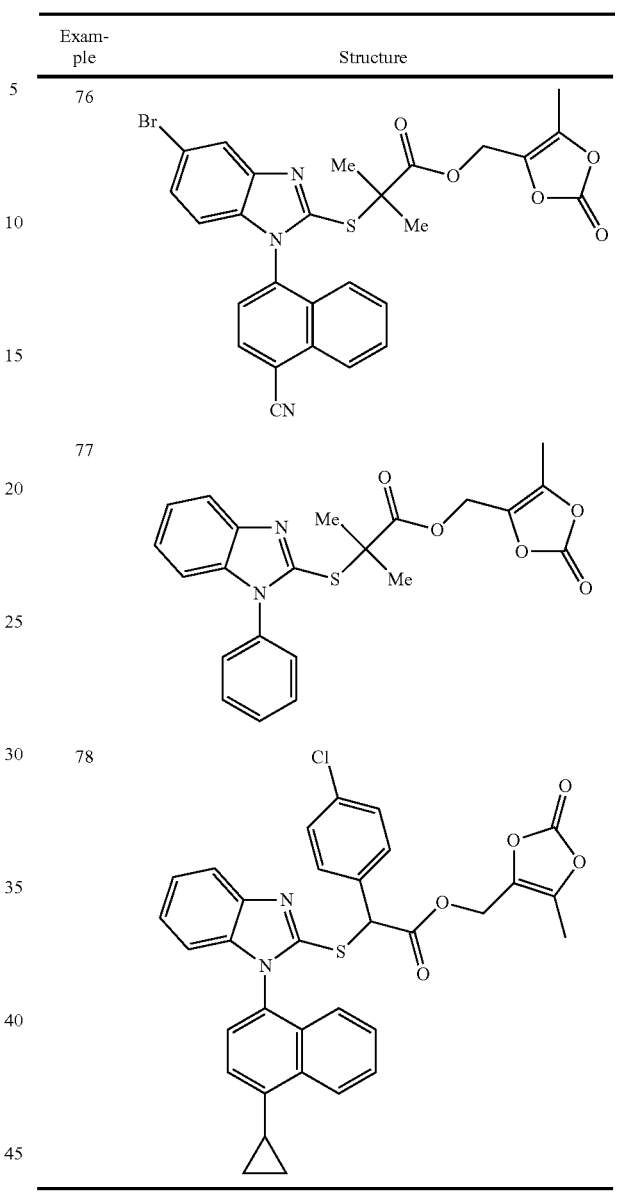 |
| 77 | 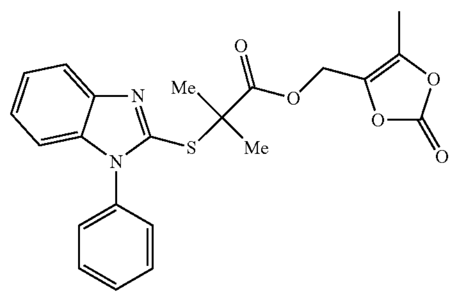 [SMILES: Cc1oc(=O)oc1COC(=O)C(C)(C)Sc1nc2ccccc2n1-c1ccccc1] |
| 78 | 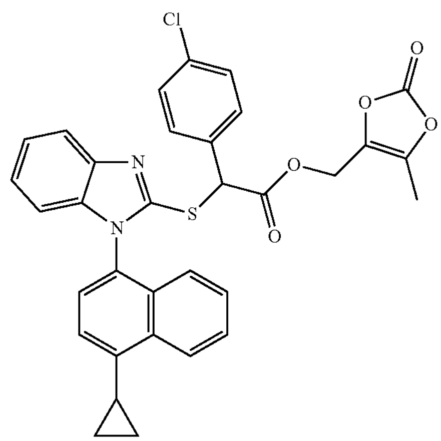 [SMILES: Cc1oc(=O)oc1COC(=O)C(Sc1nc2ccccc2n1-c1ccc(C2CC2)c2ccccc12)c1ccc(Cl)cc1] |

Example 67. (5-Methyl-2-oxo-1,3-dioxol-4-yl) methyl 2-methyl-2-[[1-(4-acetamino-2-fluorophenyl)-1H-benzo[d]imidazol-2-yl]thio]propanoate (I67)

The compound was prepared according to the preparation method described in Example 66, except that the raw material 2-methyl-2-[[5-methoxy-1-(4-cyanonaphth-1-yl)-1H-benzo[d]imidazol-2-yl]thio]propanoic acid was replaced with 2-methyl-2-[[1-(4-acetamino-2-fluorophenyl)-1H-benzo[d]imidazol-2-yl]thio]propanoic acid. The yield was 100%. LC-MS: m/z 500.1 [M+H]$^+$.

Example 68. (5-methyl-2-oxo-1,3-dioxol-4-yl) methyl 2-methyl-2-[[1-(4-bromo-2-fluorophenyl)-1H-benzo[d]imidazol-2-yl]thio]propanoate (I68)

The compound was prepared according to the preparation method described in Example 66, except that the raw material 2-methyl-2-[[5-methoxy-1-(4-cyanonaphth-1-yl)-1H-benzo[d]imidazol-2-yl]thio]propanoic acid was replaced with 2-methyl-2-[[1-(4-bromo-2-fluorophenyl)-1H-benzo[d]imidazol-2-yl]thio]propanoic acid. The yield was 100%. LC-MS: m/z 521.0 [M+H]$^+$.

Example 69. (5-methyl-2-oxo-1,3-dioxol-4-yl) methyl 2-methyl-2-[[1-(4-nitro-2-fluorophenyl)-1H-benzo[d]imidazol-2-yl]thio]propanoate (I69)

The compound was prepared according to the preparation method described in Example 66, except that the raw material 2-methyl-2-[[5-methoxy-1-(4-cyanonaphth-1-yl)-1H-benzo[d]imidazol-2-yl]thio]propanoic acid was replaced with 2-methyl-2-[[1-(4-nitro-2-fluorophenyl)-1H-benzo[d]imidazol-2-yl]thio]propanoic acid. The yield was 100%. LC-MS: m/z 488.1 [M+H]$^+$.

Example 70. (5-methyl-2-oxo-1,3-dioxol-4-yl) methyl 2-methyl-2-[[1-(4-cyanophenyl)-1H-benzo[d]imidazol-2-yl]thio]propanoate (I70)

The compound was prepared according to the preparation method described in Example 66, except that the raw material 2-methyl-2-[[5-methoxy-1-(4-cyanonaphth-1-yl)-1H-benzo[d]imidazol-2-yl]thio]propanoic acid was replaced with 2-methyl-2-[[1-(4-cyanophenyl)-1H-benzo[d]imidazol-2-yl]thio]propanoic acid. The yield was 100%. LC-MS: m/z 450.1 [M+H]$^+$.

Example 71. (5-methyl-2-oxo-1,3-dioxol-4-yl) methyl 2-methyl-2-[[1-(4-cyanonaphth-1-yl)-1H-benzo[d]imidazol-2-yl]thio]propanoate (I71)

The compound was prepared according to the preparation method described in Example 66, except that the raw material 2-methyl-2-[[5-methoxy-1-(4-cyanonaphth-1-yl)-1H-benzo[d]imidazol-2-yl]thio]propanoic acid was replaced with 2-methyl-2-[[1-(4-cyanonaphth-1-yl)-1H-benzo[d]imidazol-2-yl]thio]propanoic acid. The yield was 100%. LC-MS: m/z 500.1 [M+H]$^+$.

Example 72. (5-methyl-2-oxo-1,3-dioxol-4-yl) methyl 2-methyl-2-[[1-(4-cyclopropylnaphth-1-yl)-1H-benzo[d]imidazol-2-yl]thio]propanoate (I72)

The compound was prepared according to the preparation method described in Example 66, except that the raw material 2-methyl-2-[[5-methoxy-1-(4-cyanonaphth-1-yl)-1H-benzo[d]imidazol-2-yl]thio]propanoic acid replaced with 2-methyl-2-[[1-(4-cyclopropylnaphth-1-yl)-1H-benzo[d]imidazol-2-yl]thio]propanoic acid. The yield was 100%. LC-MS: m/z 515.2 [M+H]$^+$.

Example 73. (5-methyl-2-oxo-1,3-dioxol-4-yl) methyl 2-methyl-2-[(1-methyl-1H-benzo[d]imidazol-2-yl)thio]propanoate (I73)

The compound was prepared according to the preparation method described in Example 66, except that the raw material 2-methyl-2-[[5-methoxy-1-(4-cyanonaphth-1-yl)-1H-benzo[d]imidazol-2-yl]thio]propanoic acid was replaced with 2-methyl-2-[(1-methyl-1H-benzo[d]imidazol-2-yl)thio]propanoic acid. The yield was 100%. LC-MS: m/z 363.1 [M+H]$^+$.

Example 74. (5-methyl-2-oxo-1,3-dioxol-4-yl) methyl 2-methyl-2-[[1-(2-fluorophenyl)-1H-benzo[d]imidazol-2-yl]thio]propanoate (I74)

The compound was prepared according to the preparation method described in Example 66, except that the raw material 2-methyl-2-[[5-methoxy-1-(4-cyanonaphth-1-yl)-1H-benzo[d]imidazol-2-yl]thio]propanoic acid was replaced with 2-methyl-2-[[1 I-(2-fluorophenyl)-1H-benzo[d]imidazol-2-yl]thio]propanoic acid. The yield was 100%. LC-MS: m/z 443.1 [M+H]$^+$.

Example 75. (5-methyl-2-oxo-1,3-dioxol-4-yl) methyl 2-methyl-2-[[1-(4-chloro-2-fluorophenyl)-1H-benzo[d]imidazol-2-yl]thio]propanoate (I75)

The compound was prepared according to the preparation method described in Example 66, except that the raw material 2-methyl-2-[[5-methoxy-1-(4-cyanonaphth-1-yl)-1H-benzo[d]imidazol-2-yl]thio]propanoic acid was replaced with 2-methyl-2-[[1-(4-chloro-2-fluorophenyl)-1H-benzo[d]imidazol-2-yl]thio]propanoic acid. The yield was 100%. LC-MS: m/z 477.1 [M+H]$^+$.

Example 76. (5-methyl-2-oxo-1,3-dioxol-4-yl) methyl 2-methyl-2-[[5-bromo-1-(4-cyanonaphth-1-yl)-1H-benzo[d]imidazol-2-yl]thio]propanoate (I76)

The compound was prepared according to the preparation method described in Example 66, except that the raw material 2-methyl-2-[[5-methoxy-1-(4-cyanonaphth-1-yl)-1H-benzo[d]imidazol-2-yl]thio]propanoic acid was replaced with 2-methyl-2-[[5-bromo-1-(4-cyanonaphth-1-yl)-1H-benzo[d]imidazol-2-yl]thio]propanoic acid. The yield was 100%. LC-MS: m/z 578.0 [M+H]$^+$.

Example 77. (5-methyl-2-oxo-1,3-dioxol-4-yl) methyl 2-methyl-2-[(1-phenyl-1H-benzo[d]imidazol-2-yl)thio]propanoate (I77)

The compound was prepared according to the preparation method described in Example 66, except that the raw material 2-methyl-2-[[5-methoxy-1-(4-cyanonaphth-1-yl)-1H-benzo[d]imidazol-2-yl]thio]propanoic acid was replaced with 2-methyl-2-[(1-phenyl-1H-benzo[d]imidazol-2-yl)thio]propanoic acid. The yield was 100%. LC-MS: m/z 425.1 [M+H]$^+$.

Example 78. (5-methyl-2-oxo-1,3-dioxol-4-yl) methyl 2-(4-chlorophenyl)-2-[[1-(4-cyclopropylnaphth-1-yl)-1H-benzo[d]imidazol-2-yl]thio]acetate (I78)

The compound was prepared according to the preparation method described in Example 66, except that the raw material 2-methyl-2-[[5-methoxy-1-(4-cyanonaphth-1-yl)-1H-benzo[d]imidazol-2-yl]thio]propanoic acid was replaced with 2-(4-chlorophenyl)-2-[[1-(4-cyclopropylnaphth-1-yl)-1H-benzo[d]imidazol-2-yl]thio]acetic acid. The yield was 100%. LC-MS: m/z 597.1 [M+H]$^+$.

Example 79. Evaluation of In Vitro Efficacy of the Present Invention

A plasmid (EX-T4563-M03, GeneCopoeia) containing the full-length human URAT1 gene (SLC22A12) was transfected into Flp-InT-REx-293 cells to construct URAT1 highexpression cell 293/hURAT1. The transfected cells were assayed for ability to uptake uric acid labelled with radio-isotope. The test compounds were then evaluated for their activity by determining of their ability to block uric acid uptake by the transfected cells.

293/h URAT1 cells were plated at a density of 40000 cells/well in poly D-lysine-coated 96-well plates (BD, 356461) and incubated overnight. The medium was removed and a pre-warmed reaction buffer was added (125 mM sodium gluconate, 4.8 mM potassium gluconate, 1.3 mM calcium gluconate, 1.2 mM potassium dihydrogen phosphate, 1.2 mM magnesium sulfate, 5.6 mM glucose, 25 mM HEPES, pH 7.4) before incubating at 37° C. for 10 minutes. The buffer was removed and another reaction buffer containing 50 µM $^{14}$C-uric acid (American Radiolabeled Chemicals, ARC0513) and the test compounds or solvent control was added before incubating at 37° C. for 5 minutes. The buffer was removed, and the plates were washed 3 times with the buffer. Cells were lysed by adding 100 mM NaOH for 20 minutes. Cell lysates were transferred to Isoplate-96 well plates (PerkinElmer, 6005040), mixed with liquid scintillators and were counted in a MicroBeta$^2$ (PerkinElmer) counter.

The test compounds were all dissolved in DMSO, and DMSO of the same concentration without the test compounds was used as a solvent control. The amount of uric acid uptake by the cells in the DMSO solvent control was taken as 100%, and the inhibition of uric acid uptake by cells in the test wells for each compound was calculated as a percentage. The IC50 of each compound was calculated using the percentage of inhibition at different concentrations.

The prototype compounds described in the present invention was tested according to the above scheme, and the results are shown in the following table (for prototypes of prodrugs and salts, results from said prototype compounds were used as a reference, and in vitro tests thereof were not needed), wherein:
A indicates IC50 in the 30 µM-100 µM range;
B indicates IC50 in the 15 µM-30 µM range;
C indicates IC50 in the 1 µM-15 µM range.

| Example | URAT1 IC50 activity classification |
|---|---|
| Lesinurad | A |
| I1 | C |
| I2 | C |
| I3 | C |
| I4 | C |
| I5 | B |
| I6 | B |
| I7 | A |
| I8 | A |
| I9 | — |
| I10 | — |
| I11 | B |
| I12 | B |
| I13 | B |

Example 80. Evaluation of In Vivo Efficacy of the Present Invention (1) Experimental Materials Experimental animals: SD rats (SPF level), Laboratory Animal Center, Chinese Academy of Military Medical Sciences.

Experimental compounds: Compounds I2, I3 and I4 of this invention, and Lesinurad (positive drug)

Instruments: Centrifuge, Thermo Fisher Scientific, Model: ThermoSorvall ST 40; Hitachi 7600 automatic biochemical analyzer equipped with the corresponding reagents; Electronic balance, Sartorius, Model: BSA3202S-CW; Electronic balance, Mettler-Toledo, Model: LE204.

(2) Experimental Procedure

Rats weighing 200±20 g were fasted for 12 hours after a 1-week adaptive feeding period and were intraperitoneally injected with potassium oxonate (250 mg/kg/d) once daily for 7 consecutive days for modeling. The rats were closely observed after injection. 1 hour after the daily intraperitoneal injection of potassium oxonate, 40 mg/kg/d and 20 mg/kg/d of the test compound was intragastrically administered once daily for 7 consecutive days.

Blood samples were collected from the retro-orbital venous plexus before the preparation of the rat models and after administering the test compounds for 7 days. Serum was separated from the blood samples. Urine was collected using a metabolic cage for 24 hours and the supernatant was collected after centrifuge. Blood uric acid levels were measured using an automatic biochemical analyzer. The average increment in blood uric acid concentration was calculated for each group of animals.

The increment of blood uric acid concentration =

$$\left(\frac{\text{blood uric acid concentration after 7-day drug administration}}{\text{blood uric acid concentration before drug administration}} - 1\right) \times 100\%.$$

SPSS 13.0 statistical software package was used to analyze the data. The data in each group were expressed as mean plus or minus standard deviation (x±s). The data were compared using a comparative t-test between groups, where p<0.05 was considered as statistically significant.

Experimental Results

Changes in blood uric acid levels in hyperuricemia rat models

TABLE 1

Therapeutic effect of test compounds on hyperuricemia rat models

| Group | No. of animals | Blood uric acid concentration (µmol/L) before drug administration | Blood uric acid concentration (µmol/L) 7 days after drug administration | Blood uric acid increase (%) |
|---|---|---|---|---|
| Blank control | 8 | 160.80 ± 18.41 | 162.88 ± 8.98 | 1.29 |
| Model control | 8 | 153.98 ± 18.33 | 182.15 ± 8.5$^{\#\#}$ | 18.29 |
| Lesinurad 80 mg/kg/d | 8 | 161.20 ± 22.07 | 166.85 ± 12.76* | 3.50 |
| Lesinurad 40 mg/kg/d | 8 | 156.02 ± 8.69 | 172.57 ± 25.43 | 10.61 |
| I1 80 mg/kg/d | 8 | 175.83 ± 16.39 | 175.95 ± 15.43** | 0.07 |
| I1 40 mg/kg/d | 8 | 169.61 ± 19.57 | 175.79 ± 16.54* | 3.64 |
| I2 80 mg/kg/d | 8 | 150.86 ± 20.46 | 161.81 ± 8.38 | 7.26 |
| I2 40 mg/kg/d | 8 | 156.38 ± 12.62 | 172.86 ± 9.37* | 10.54 |
| I3 80 mg/kg/d | 8 | 181.25 ± 24.86 | 159.40 ± 13.99** | -12.06 |
| I3 40 mg/kg/d | 8 | 169.21 ± 14.24 | 180.38 ± 14.36 | 6.60 |

TABLE 1-continued

Therapeutic effect of test compounds on hyperuricemia rat models

| Group | No. of animals | Blood uric acid concentration (μmol/L) before drug administration | Blood uric acid concentration (μmol/L) 7 days after drug administration | Blood uric acid increase (%) |
|---|---|---|---|---|
| I4 80 mg/kg/d | 8 | 158.38 ± 13.67 | 177.24 ± 5.77 | 11.90 |
| I4 40 mg/kg/d | 8 | 142.57 ± 6.43 | 173.05 ± 17.24* | 21.38 |

Note:
Compared with the blank control group,
$p < 0.01$.
Compared with the model control group,
*$p < 0.05$,
**$p < 0.01$.

As shown in Table 1, comparing with the blank group, the blood uric acid levels in the model group were significantly higher ($p<0.01$) after 7 days of modeling. Comparing with the model group, Lesinurad (80 mg/kg/day and 40 mg/kg/day) could reduce the increment of blood uric acid levels in animals, which was significantly different from the model control group ($p<0.05$). The compounds I1, I2, I3 (80 mg/kg/day and 40 mg/kg/day) in the present invention could significantly reduce the increment of blood uric acid levels caused by potassium oxonate, which was significantly different from that of the model control group, demonstrating certain effect of lowering uric acid levels.

What is claimed is:

1. A benzimidazole derivative having the structure of Formula (I):

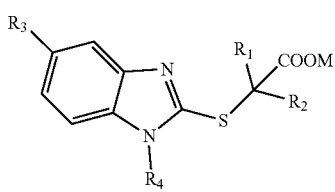

Formula (I)

or a pharmaceutically acceptable salt or prodrug thereof, wherein:
$R_1$ and $R_2$ are selected from the group consisting of alkyl;
$R_3$ is selected from the group consisting of hydrogen, halogen, cyano, linear or branched $C_{1-6}$ alkyl and linear or branched $C_{1-6}$ alkoxy;
$R_4$ is selected from the group consisting of phenyl, substituted phenyl, naphthyl and substituted naphthyl, wherein the substituent in said substituted phenyl and substituted naphthyl is selected from the group consisting of halogen, cyano, alkyl, alkoxy, ester, N-acyl derivatives, N-acyloxy derivatives and amino acid conjugates; and
M is selected from the group consisting of hydrogen, alkyl, and pharmaceutically acceptable cations.

2. The benzimidazole derivative of claim 1, wherein said pharmaceutically acceptable salt is selected from the group consisting of Na, K, Li, Ca and Mg salts.

3. The benzimidazole derivative of claim 1, wherein said pharmaceutically acceptable prodrug is selected from the group consisting of esters, carbonates, thiocarbonates, N-acyl derivatives, N-acyloxy derivatives and amino acid conjugates.

4. The benzimidazole derivative of claim 1, wherein said benzimidazole derivative is selected from the group consisting of:
2-methyl-2-[[5-methoxy-1-(4-cyanonaphth-1-yl)-1H-benzo[d]imidazol-2-yl]thio]propanoic acid (I1);
2-methyl-2-[[1-(4-cyanonaphth-1-yl)-1H-benzo[d]imidazol-2-yl]thio]propanoic acid (I2);
2-methyl-2-[[5-bromo-1-(4-cyanonaphth-1-yl)-1H-benzo[d]imidazol-2-yl]thio]propanoic acid (I3);
2-methyl-2-[[1-(4-cyanophenyl)-1H-benzo[d]imidazol-2-yl]thio]propanoic acid (I4);
2-methyl-2-[[1-(4-cyclopropylnaphth-1-yl)-1H-benzo[d]imidazol-2-yl]thio]propanoic acid (I5);
2-methyl-2-[[1-(4-nitro-2-fluorophenyl)-1H-benzo[d]imidazol-2-yl]thio]propanoic acid (I7);
2-methyl-2-[(1-phenyl-1H-benzo[d]imidazol-2-yl)thio]propanoic acid (I8);
2-methyl-2-[[1-(4-acetamino-2-fluorophenyl)-1H-benzo[d]imidazol-2-yl)thio]propanoic acid (I10);
2-methyl-2-[[1-(4-bromo-2-fluorophenyl)-1H-benzo[d]imidazol-2-yl]thio]propanoic acid (I11);
2-methyl-2-[[1-(4-chloro-2-fluorophenyl)-1H-benzo[d]imidazol-2-yl]thio]propanoic acid (I12);
2-methyl-2-[[1-(2-fluorophenyl)-1H-benzo[d]imidazol-2-yl]thio]propanoic acid (I13);
Sodium 2-methyl-2-[[5-methoxy-1-(4-cyclopropylnaphth-1-yl)-1H-benzo[d]imidazol-2-yl]thio]propanoate (I14);
Sodium 2-methyl-2-[[1-(4-acetamino-2-fluorophenyl)-1H-benzo[d]imidazol-2-yl]thio]propanoate (I15);
Sodium 2-methyl-2-[[1-(4-bromo-2-fluorophenyl)-1H-benzo[d]imidazol-2-yl]thio]propanoate (I16);
Sodium 2-methyl-2-[[1-(4-nitro-2-fluorophenyl)-1H-benzo[d]imidazol-2-yl]thio]propanoate (I17);
Sodium 2-methyl-2-[[1-(4-cyanophenyl)-1H-benzo[d]imidazol-2-yl]thio]propanoate (I18);
Sodium 2-methyl-2-[[1-(4-cyanonaphth-1-yl)-1H-benzo[d]imidazol-2-yl]thio]propanoate (I19);
Sodium 2-methyl-2-[[1-(4-cyclopropylnaphth-1-yl)-1H-benzo[d]imidazol-2-yl]thio]propanoate (I20);
Sodium 2-methyl-2-[[1-(2-fluorophenyl)-1H-benzo[d]imidazol-2-yl]thio]propanoate (I22);
Sodium 2-methyl-2-[[1-(4-chloro-2-fluorophenyl)-1H-benzo[d]imidazol-2-yl]thio]propanoate (I23);
Sodium 2-methyl-2-[[5-bromo-1-(4-cyanonaphth-1-yl)-1H-benzo[d]imidazol-2-yl]thio]propanoate (I24);
Sodium 2-methyl-2-[(1-phenyl-1H-benzo[d]imidazol-2-yl)thio]propanoate (I25);
Potassium 2-methyl-2-[[5-methoxy-1-(4-cyanonaphth-1-yl)-1H-benzo[d]imidazol-2-yl]thio]propanoate (I27);
Potassium 2-methyl-2-[[1-(4-acetamino-2-fluorophenyl)-1H-benzo[d]imidazol-2-yl]thio]propanoate (I28);
Potassium 2-methyl-2-[[1-(4-bromo-2-fluorophenyl)-1H-benzo[d]imidazol-2-yl]thio]propanoate (I29);
Potassium 2-methyl-2-[[1-(4-nitro-2-fluorophenyl)-1H-benzo[d]imidazol-2-yl]thio]propanoate (I30);
Potassium 2-methyl-2-[[1-(4-cyanophenyl)-1H-benzo[d]imidazol-2-yl]thio]propanoate (I31);
Potassium 2-methyl-2-[[1-(4-cyano-1-naphth-1)-1H-benzo[d]imidazol-2-yl]thio]propanoate (I32);
Potassium 2-methyl-2-[[1-(4-cyclopropylnaphth-1-yl)-1H-benzo[d]imidazol-2-yl]thio]propanoate (I33);
Potassium 2-methyl-2-[[1-(2-fluorophenyl)-1H-benzo[d]imidazol-2-yl]thio]propanoate (I35);
Potassium 2-methyl-2-[[1-(4-chloro-2-fluorophenyl)-1H-benzo[d]imidazol-2-yl]thio]propanoate (I36);

Potassium 2-methyl-2-[[5-bromo-1-(4-cyanonaphth-1-yl)-1H-benzo[d]imidazol-2-yl]thio]propanoate (I37);
Potassium 2-methyl-2-(1-phenyl-1H-benzo[d]imidazol-2-yl)thio]propanoate (I38);
Methyl 2-methyl-2-[[5-methoxy-1-(4-cyanonaphth-1-yl)-1H-benzo[d]imidazol-2-yl]thio]propanoate (I40);
Methyl 2-methyl-2-[[1-(4-acetamino-2-fluorophenyl)-1H-benzo[d]imidazol-2-yl]thio]propanoate (I41);
Methyl 2-methyl-2-[[1-(4-bromo-2-fluorophenyl)-1H-benzo[d]imidazol-2-yl]thio]propanoate (I42);
Methyl 2-methyl-2-[[1-(4-nitro-2-fluorophenyl)-1H-benzo[d]imidazol-2-yl]thio]propanoate (I43);
Methyl 2-methyl-2-[[1-(4-cyanophenyl)-1H-benzo[d]imidazol-2-yl]thio]propanoate (I44);
Methyl 2-methyl-2-[[1-(4-cyanonaphth-1-yl)-1H-benzo[d]imidazol-2-yl]thio]propanoate (I45);
Methyl 2-methyl-2-[[1-(4-cyclopropylnaphth-1-yl)-1H-benzo[d]imidazol-2-yl]thio]propanoate (I46);
Methyl 2-methyl-2-[[1-(2-fluorophenyl)-1H-benzo[d]imidazol-2-yl]thio]propanoate (I48);
Methyl 2-methyl-2-[[1-(4-chloro-2-fluorophenyl)-1H-benzo[d]imidazol-2-yl]thio]propanoate (I49);
Methyl 2-methyl-2-[(4-cyanonaphth-1-yl)-1H-benzo[d]imidazol-2-yl]thio]propanoate (I50);
Methyl 2-methyl-2-[(1-phenyl-1H-benzo[d]imidazol-2-yl)thio]propanoate (I51);
Methyl 2-(4-chlorophenyl)-2-[[1-4-cyclopropylnaphth-1-yl)-1H-benzo[d]imidazol-2-yl]thio]acetate (I52);
Ethyl 2-methyl-2-[[5-methoxy-1-(4-cyanonaphth-1-yl)-1H-benzo[d]imidazol-2-yl]thio]propanoate (I53);
Ethyl 2-methyl-2-[[1-(4-acetamino-2-fluorophenyl)-1H-benzo[d]imidazol-2-yl]thio]propanoate (I5);
Ethyl 2-methyl-2-[[1-(4-bromo-2-fluorophenyl)-1H-benzo[d]imidazol-2-yl]thio]propanoate (I55);
Ethyl 2-methyl-2-[[1-(4-nitro-2-fluorophenyl)-1H-benzo[d]imidazol-2-yl]thio]propanoate (I56);
Ethyl 2-methyl-2-[[1-(4-cyanophenyl)-1H-benzo[d]imidazol-2-yl]thio]propanoate (I57);
Ethyl 2-methyl-2-[[1-(4-cyanonaphth-1-yl)-1H-benzo[d]imidazol-2-yl]thio]propanoate (I58);
Ethyl 2-methyl-2-[[1-(4-cyclopropylnaphth-1-yl)-1H-benzo[d]imidazol-2-yl]thio]propanoate (I59);
Ethyl 2-methyl-2-[[1-(2-fluorophenyl)-1H-benzo[d]imidazol-2-yl]thio]propanoate (I61);
Ethyl 2-methyl-2-[[1-(4-chloro-2-fluorophenyl)-1H-benzo[d]imidazol-2-yl]thio]propanoate (I62);
Ethyl 2-methyl-2-[[5-bromo-1-(4-cyanonaphth-1-yl)-1H-benzo[d]imidazol-2-yl]thio]propanoate (I63); and
Ethyl 2-methyl-2-[(1-phenyl-1H-benzo[d]imidazol-2-yl)thio]propanoate (I64).

5. A method of preparing the benzimidazole derivative of claim 1, said method comprising the steps of:
(1) Reacting a compound of Formula (II) with a compound of Formula (I in the presence of a base to form a compound of Formula (IV);

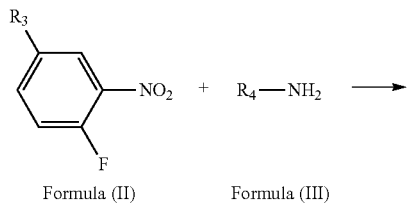

Formula (II)   Formula (III)

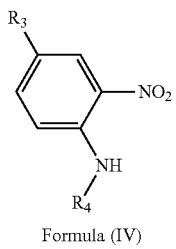

Formula (IV)

(2) Reacting said compound of Formula (IV) with a reducing agent to form a compound of Formula (V);

Formula (IV) → Formula (V)

(3) Reacting said compound of Formula compound (V) with thiophosgene to form a compound of Formula (VI);

Formula (V) → Formula (VI)

(4) Reacting said compound of Formula (VI) with a compound of Formula (VII) under basic condition to form a compound of Formula (VIII);

Formula (VI) + Formula (VII) → Formula (VIII)

(5) Hydrolyzing said compound of Formula (VIII) under basic condition to form a compound of Formula (IX);

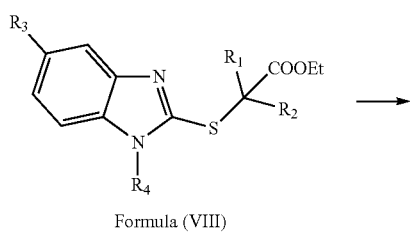

Formula (VIII)

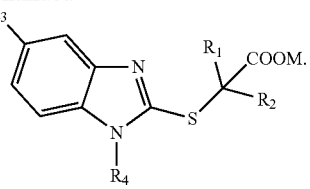

Formula (I)

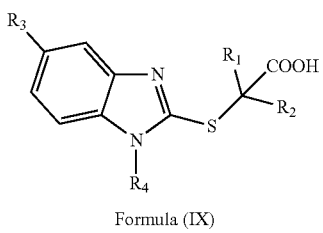

Formula (IX)

(6) Reacting said compound of Formula (IX) with a base to form a compound of Formula (I), wherein M is a pharmaceutically acceptable cation; or reacting said compound of Formula (IX) with a chlorinating reagent, followed by an alcohol to form a compound of Formula (I), wherein M is $C_{1-6}$ alkyl.

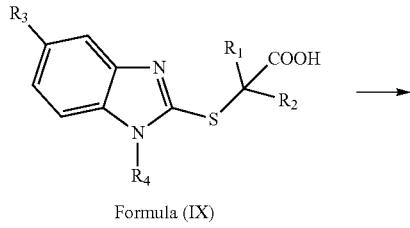

Formula (IX)

6. The method of claim 5, whereon said chlorinating reagent is selected from the group consisting of oxalyl chloride, thionyl chloride, phosphorus trichloride, phosphorus pentachloride and triphosgene.

7. A pharmaceutical composition comprising the benzimidazole derivative of claim 1.

8. A method for modulating uric acid levels and/or treating gout in a subject in need thereof, comprising the step of administering an effective amount of the pharmaceutical composition of claim 7 to said subject.

9. A method for modulating uric acid levels and/or treating gout in a subject in need thereof, comprising the step of administering an effective amount of the benzimidazole derivative of claim 1 to said subject.

10. The method of claim 9, wherein said subject suffers from hyperuricemia, gout, gouty arthritis, inflammatory arthritis, nephropathy, nephrolithiasis, joint inflammation, deposition of urate crystals within joints, urolithiasis, deposition of urate crystals in renal parenchyma, gout attack, tophaceous gout or any combinations thereof.

11. A method for modulating uric acid levels and/or treating gout in a subject in need thereof, comprising the step of administering to said subject the benzimidazole derivative of claim 1 in combination with a drug.

12. The method of claim 11, wherein said drug is selected from the group consisting of URAT1 inhibitor, xanthine oxidase inhibitor, xanthine dehydrogenase, xanthine oxidoreductase inhibitor, purine nucleoside phosphorylase inhibitor, uric acid transporter inhibitor, glucose transporter inhibitor, organic anion transporter (OAT) inhibitor, OAT-4 inhibitor and any combinations thereof.

* * * * *